United States Patent
Wang et al.

(10) Patent No.: US 9,512,108 B2
(45) Date of Patent: Dec. 6, 2016

(54) 9,9,10,10-TETRAFLUORO-9,10-DIHYDROPHENANTHRENE HEPATITIS C VIRUS INHIBITOR AND APPLICATION THEREOF

(71) Applicant: NANJING SANHOME PHARMACEUTICAL CO., LTD., Nanjing, Jiangsu (CN)

(72) Inventors: Yong Wang, Nanjing (CN); Liwen Zhao, Nanjing (CN); Dezhong Wang, Nanjing (CN); Haiping Zhou, Nanjing (CN); Xian Zhang, Nanjing (CN); Hongyan Chen, Nanjing (CN); Di Zhang, Nanjing (CN); Cang Zhang, Nanjing (CN)

(73) Assignee: NANJING SANHOME PHARMACEUTICAL CO., LTD., Nanjing (CN)

( * ) Notice: Subject to any disclaimer, the term of this patent is extended or adjusted under 35 U.S.C. 154(b) by 0 days.

(21) Appl. No.: 15/030,990

(22) PCT Filed: Dec. 26, 2014

(86) PCT No.: PCT/CN2014/095043
§ 371 (c)(1),
(2) Date: Apr. 21, 2016

(87) PCT Pub. No.: WO2015/101215
PCT Pub. Date: Jul. 9, 2015

(65) Prior Publication Data
US 2016/0297804 A1    Oct. 13, 2016

(30) Foreign Application Priority Data

Dec. 31, 2013    (CN) .......................... 2013 1 0754318

(51) Int. Cl.
*A61K 31/4178*    (2006.01)
*C07D 403/14*    (2006.01)
*C07C 25/22*    (2006.01)
*C07F 5/02*    (2006.01)
*C07D 491/113*    (2006.01)

(52) U.S. Cl.
CPC ............. *C07D 403/14* (2013.01); *C07C 25/22* (2013.01); *C07D 491/113* (2013.01); *C07F 5/025* (2013.01)

(58) Field of Classification Search
CPC .......................... A61K 31/4148; C07D 403/14
USPC ............................ 514/397; 548/311.4, 313.1
See application file for complete search history.

(56) References Cited

U.S. PATENT DOCUMENTS

2014/0249074 A1    9/2014  Bacon et al.

FOREIGN PATENT DOCUMENTS

CN           102596936           7/2012
WO      WO 2012/068234           5/2012

OTHER PUBLICATIONS

English translation of PCT International Search Report issued in International Application No. PCT/CN2014/095043, dated Apr. 1, 2015.

*Primary Examiner* — Charanjit Aulakh
(74) *Attorney, Agent, or Firm* — Parker Highlander PLLC

(57) ABSTRACT

The present invention belongs to the field of chemical pharmaceuticals, and specifically relates to compounds represented by formula I having a 9,9,10,10-tetrafluoro-9,10-dihydrophenanthrene structure and being able to inhibit hepatitis C virus activity, or a pharmaceutically acceptable salt, isomer, solvate, crystal or prodrug of said compounds, a pharmaceutical composition containing said compounds, and an application of said compounds or composition in the preparation of a drug. The compounds of the present invention have a good HCV inhibitory effect.

19 Claims, No Drawings

9,9,10,10-TETRAFLUORO-9,10-DIHYDROPHENANTHRENE HEPATITIS C VIRUS INHIBITOR AND APPLICATION THEREOF

This application is a national phase application under 35 U.S.C. §371 of International Application No. PCT/CN2014/095043, filed Dec. 26, 2014, which claims the benefit of priority to Chinese Patent Application No. 201310754318.4, filed Dec. 31, 2013, the entirety of each of which is incorporated herein by reference.

FIELD OF THE INVENTION

The present invention belongs to the field of chemical pharmaceuticals, and specifically relates to a compound having a 9,9,10,10-tetrafluoro-9,10-dihydro phenanthrene structure and being able to inhibit hepatitis C virus activity, or a pharmaceutically acceptable salt, isomer, solvate, crystal or prodrug of said compound, a pharmaceutical composition containing said compound, and an application of said compound or composition in the preparation of a drug.

BACKGROUND OF THE INVENTION

Viral hepatitis C is an infectious disease of liver acute or chronic inflammation caused by Hepatitis C virus (HCV). The infection of HCV is susceptible to develop into chronic liver diseases, such as chronic hepatitis, liver cirrhosis and liver cancer, and thus seriously affecting people's physical health.

HCV belongs to the Flaviviridae family, and currently can be divided into six genotypes and various subtypes. According to the internationally accepted method, the genotype of HCV is represented by Arabic numerals, and the gene subtype is represented by English lowercase letters, wherein genotype 1 presents a global distribution, and accounts for 70% or more of all the HCV infections, in which the main infection type of Chinese population is HCV 1b subtype. Studies have found that both the 5'- and 3'-ends of the positive strand RNA of HCV contain non-coding region (UTR), and a large multi-protein open reading frame (ORF) is located between UTRs. The ORF encodes a polyprotein precursor of about 3,000 amino acids, which is cleaved into a variety of HCV mature proteins under the combined actions of the signal peptidases encoded by the host and the proteases encoded by HCV. The HCV mature protein comprises four structural proteins and six non-structural proteins, of which the six non-structural proteins are named as NS2, NS3, NS4A, NS4B, NS5A, NS5B, respectively. Studies suggest that the six non-structural proteins play very important roles in the replication of HCV, for example, NS3, in which NS3 serine protease activity can be regulated, and NS5A, which is a phosphorylated protein, contains a interferon sensitivity determining region and has important roles in interferon therapy forecast, viral replication, antiviral resistance, hepatocellular carcinogenesis and other aspects, and has become a research focus for HCV non-structural proteins.

Currently, the treatment method for HCV infection is generally recombinant interferon α alone or a combined therapy of recombinant interferon α with nucleoside analogue ribavirin. However, for either interferon or ribavirin, there are a plurality of contraindications, and the clinical benefit are limited. Therefore, there remains a great demand for drugs which can effectively treat HCV infection.

SUMMARY OF THE INVENTION

An object of the present invention is to provide a compound of general formula I having a 9,9,10,10-tetrafluoro-9,10-dihydrophenanthrene structure and being able to inhibit HCV, or a pharmaceutically acceptable salt, isomer, solvate, crystal or prodrug thereof,

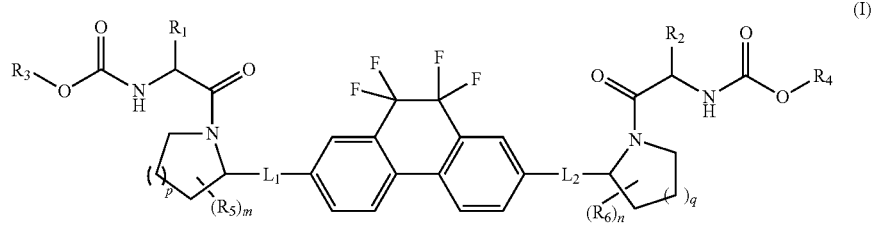

(I)

wherein:

each of $L_1$ and $L_2$ is independently selected from the group consisting of aryl, heteroaryl, -aryl-aryl-, -aryl-heteroaryl-, and -heteroaryl-heteroaryl-, wherein the aryl or heteroaryl can be substituted with one or more of halogen, hydroxyl, amino, carboxyl, cyano, nitro, alkyl, cycloalkyl, heterocycloalkyl, alkoxy, haloalkyl, hydroxyalkyl, aminoalkyl, carboxyalkyl, cyanoalkyl, nitroalkyl, cycloalkylalkyl, heterocycloalkylalkyl, alkoxyalkyl, monoalkylamino, monoalkylaminoalkyl, dialkylamino, dialkylaminoalkyl, alkylacyl, alkylacylalkyl, alkoxyacyl, alkoxyacylalkyl, alkylacyloxy, alkylacyloxyalkyl, aminoacyl, aminoacylalkyl, mono alkylaminoacyl, monoalkylaminoacylalkyl, dialkylaminoacyl, dialkylaminoacylalkyl, alkylacylamino and alkylacylaminoalkyl;

each of p and q is independently selected from the group consisting of 1, 2 and 3;

each of $R_1$ and $R_2$ is independently selected from the group consisting of hydrogen, alkyl, cycloalkyl, heterocycloalkyl, aryl or heteroaryl, wherein the alkyl, cycloalkyl, heterocycloalkyl, aryl or heteroaryl can be substituted with one or more of halogen, hydroxyl, amino, carboxyl, cyano, nitro, alkyl, cycloalkyl, heterocycloalkyl, alkoxy, haloalkyl, hydroxyalkyl, carboxyalkyl, monoalkylamino, dialkylamino, alkylacyl, alkoxyacyl, alkylacyloxy, aminoacyl, monoalkylaminoacyl, dialkylaminoacyl and alkylacylamino;

each of $R_3$ and $R_4$ is independently selected from the group consisting of hydrogen, alkyl, cycloalkyl or heterocycloalkyl, wherein the alkyl, cycloalkyl or heterocycloalkyl can be substituted with one or more of halogen, hydroxyl, amino, carboxyl, cyano, nitro, alkyl, cycloalkyl, heterocycloalkyl, alkoxy, aryl and heteroaryl; and each of $R_5$ and $R_6$ is independently selected from the group consisting of hydrogen, halogen, hydroxyl, amino, carboxyl, cyano, nitro, alkyl, cycloalkyl, heterocycloalkyl, alkoxy, alkoxyalkyl, aryl and heteroaryl, wherein each of m and n is independently selected from the group consisting of 1, 2 and 3, and when m or n is 2, each $R_5$ or $R_6$ together with the C atom to which they are attached can form a cycloalkyl or heterocycloalkyl; wherein the hydroxyl, amino, carboxyl, alkyl, cycloalkyl, heterocycloalkyl, alkoxy, alkoxyalkyl, aryl and heteroaryl can be substituted with one or more of halogen, hydroxyl, amino, carboxyl, cyano, nitro, alkyl, cycloalkyl, heterocycloalkyl, alkoxy, hydroxyalkyl, carboxyalkyl, monoalkylamino, dialkylamino, alkylacyl, alkoxyacyl, alkylacyloxy, aminoacyl, monoalkylaminoacyl, dialkylaminoacyl and alkylacylamino.

Another object of the present invention is to provide a method for preparing the compound of general formula I of the present invention or a pharmaceutically acceptable salt, isomer, solvate, crystal or prodrug thereof.

A further object of the present invention is to provide a composition comprising the compound of general formula I of the present invention or a pharmaceutically acceptable salt, isomer, solvate, crystal or prodrug thereof and a pharmaceutically acceptable carrier, as well as a composition comprising the compound of general formula I of the present invention or a pharmaceutically acceptable salt, isomer, solvate, crystal or prodrug thereof and one or more additional HCV inhibitors.

A further object of the present invention is to provide a method for treating and/or preventing a disease caused by hepatitis C virus such as a liver disease with the compound of general formula I of the present invention or a pharmaceutically acceptable salt, isomer, solvate, crystal or prodrug thereof, and use of the compound of general formula I of the present invention or a pharmaceutically acceptable salt, isomer, solvate, crystal or prodrug thereof in the manufacture of a medicament for treating and/or preventing HCV infection.

For the above objects, the present invention provides the following technical solutions:

In the first aspect, the present invention provides a compound of general formula I or a pharmaceutically acceptable salt, isomer, solvate, crystal or prodrug thereof, lacyloxy, alkylacyloxyalkyl, aminoacyl, aminoacylalkyl, mono alkylaminoacyl, monoalkylaminoacylalkyl, dialkylaminoacyl, dialkylaminoacylalkyl, alkylacylamino and alkylacylaminoalkyl;

each of p and q is independently selected from the group consisting of 1, 2 and 3;

each of $R_1$ and $R_2$ is independently selected from the group consisting of hydrogen, alkyl, cycloalkyl, heterocycloalkyl, aryl or heteroaryl, wherein the alkyl, cycloalkyl, heterocycloalkyl, aryl or heteroaryl can be substituted with one or more of halogen, hydroxyl, amino, carboxyl, cyano, nitro, alkyl, cycloalkyl, heterocycloalkyl, alkoxy, haloalkyl, hydroxyalkyl, carboxyalkyl, monoalkylamino, dialkylamino, alkylacyl, alkoxyacyl, alkylacyloxy, aminoacyl, monoalkylaminoacyl, dialkylaminoacyl and alkylacylamino;

each of $R_3$ and $R_4$ is independently selected from the group consisting of hydrogen, alkyl, cycloalkyl and heterocycloalkyl, wherein the alkyl, cycloalkyl or heterocycloalkyl can be substituted with one or more of halogen, hydroxyl, amino, carboxyl, cyano, nitro, alkyl, cycloalkyl, heterocycloalkyl, alkoxy, aryl and heteroaryl; and each of $R_5$ and $R_6$ is independently selected from the group consisting of hydrogen, halogen, hydroxyl, amino, carboxyl, cyano, nitro, alkyl, cycloalkyl, heterocycloalkyl, alkoxy, alkoxyalkyl, aryl and heteroaryl, wherein each of m and n is independently selected from the group consisting of 1, 2 and 3, and when m or n is 2, each $R_5$ or $R_6$ together with the C atom to which they are attached can form a cycloalkyl or heterocycloalkyl; wherein the hydroxyl, amino, carboxyl, alkyl, cycloalkyl, heterocycloalkyl, alkoxy, alkoxyalkyl, aryl and heteroaryl can be substituted with one or more of halogen, hydroxyl, amino, carboxyl, cyano, nitro, alkyl, cycloalkyl, heterocycloalkyl, alkoxy, hydroxyalkyl, carboxyalkyl, monoalkylamino, dialkylamino, alkylacyl, alkoxyacyl, alkylacyloxy, aminoacyl, monoalkylaminoacyl, dialkylaminoacyl and alkylacylamino.

In some preferred embodiments, the compound of the present invention is the compound of general formula I and a pharmaceutically acceptable salt, isomer, solvate, crystal or prodrug thereof, wherein:

each of $L_1$ and $L_2$ is independently selected from the group consisting of phenyl, naphthyl, imidazolyl, benzimi-

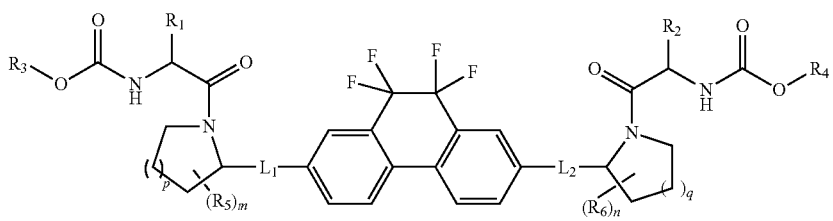

(I)

wherein:

each of $L_1$ and $L_2$ is independently selected from the group consisting of aryl, heteroaryl, -aryl-aryl-, -aryl-heteroaryl-, or -heteroaryl-heteroaryl-, wherein the aryl or heteroaryl can be substituted with one or more of halogen, hydroxyl, amino, carboxyl, cyano, nitro, alkyl, cycloalkyl, heterocycloalkyl, alkoxy, haloalkyl, hydroxyalkyl, aminoalkyl, carboxyalkyl, cyanoalkyl, nitroalkyl, cycloalkylalkyl, heterocycloalkylalkyl, alkoxyalkyl, monoalkylamino, monoalkylaminoalkyl, dialkylamino, dialkylaminoalkyl, alkylacyl, alkylacylalkyl, alkoxyacyl, alkoxyacylalkyl, alkydazolyl, -phenyl-imidazolyl-, imidazopyridyl, quinazolinonyl, pyrrolyl, imidazolonyl, furanyl, thienyl, pyrazolyl, oxazolyl, thiazolyl, isoxazolyl, isothiazolyl, oxadiazolyl and triazolyl, wherein the phenyl, naphthyl, imidazolyl, benzimidazolyl, -phenyl-imidazolyl-, imidazopyridyl, quinazolinonyl, pyrrolyl, imidazolonyl, furanyl, thienyl, pyrazolyl, oxazolyl, thiazolyl, isoxazolyl, isothiazolyl, oxadiazolyl and triazolyl can be substituted with one or more of halogen, hydroxyl, amino, carboxyl, cyano, nitro, $C_{1-10}$ alkyl, $C_{3-10}$ cycloalkyl, $C_{3-10}$ heterocycloalkyl, $C_{1-10}$ alkoxy, $C_{1-10}$ haloalkyl, hydroxy-$C_{1-10}$ alkyl, amino-$C_{1-10}$ alkyl, carboxy- $C_{1-10}$ alkyl, cyano-$C_{1-10}$ alkyl, nitro-$C_{1-10}$ alkyl, $C_{3-10}$ cycloalkyl-$C_{1-6}$ alkyl, $C_{3-10}$ heterocycloalkyl-$C_{1-6}$ alkyl, $C_{1-10}$ alkoxy-$C_{1-6}$ alkyl, mono$C_{1-10}$ alkylamino, mono$C_{1-10}$ alkylamino-$C_{1-6}$ alkyl, di$C_{1-10}$ alkylamino, di$C_{1-10}$ alkylamino-$C_{1-6}$ alkyl, $C_{1-10}$ alkylacyl, $C_{1-10}$ alkylacyl-$C_{1-6}$ alkyl, $C_{1-10}$ alkoxyacyl, $C_{1-10}$ alkoxyacyl-$C_{1-6}$ alkyl, $C_{1-10}$ alkylacyloxy, $C_{1-10}$ alkylacyloxy-$C_{1-6}$ alkyl, aminoacyl, aminoacyl-$C_{1-6}$ alkyl, mono$C_{1-10}$ alkylaminoacyl, mono$C_{1-10}$ alkylaminoacyl-$C_{1-6}$ alkyl, di$C_{1-10}$ alkylaminoacyl, di$C_{1-10}$ alkylaminoacyl-$C_{1-6}$ alkyl, $C_{1-10}$ alkylacylamino and $C_{1-10}$ alkylacylamino-$C_{1-6}$ alkyl;

preferably, each of $L_1$ and $L_2$ is independently selected from the group consisting of phenyl, naphthyl, imidazolyl, 1H-benzo[d]imidazolyl, 5-phenyl-1H-imidazolyl, 1H-imidazo[4,5-b]pyridyl, quinazolin-4(3H)-onyl, pyrrolyl, imidazolonyl, furyl, thienyl, pyrazolyl, oxazolyl, thiazolyl, isoxazolyl, isothiazolyl, oxadiazolyl and triazolyl, wherein the phenyl, naphthyl, imidazolyl, 1H-benzo[d]imidazolyl, 5-phenyl-1H-imidazolyl, 1H-imidazo[4,5-b]pyridyl, quinazolin-4(3H)-onyl, pyrrolyl, imidazolonyl, furyl, thienyl, pyrazolyl, oxazolyl, thiazolyl, isoxazolyl, isothiazolyl, oxadiazolyl and triazolyl can be substituted with one or more of halogen, hydroxyl, amino, carboxyl, cyano, nitro, $C_{1-6}$ alkyl, $C_{3-8}$ cycloalkyl, $C_{3-8}$ heterocycloalkyl, $C_{1-6}$ alkoxy, $C_{1-6}$ haloalkyl, hydroxy-$C_{1-6}$ alkyl, amino-$C_{1-6}$ alkyl, carboxy-$C_{1-6}$ alkyl, cyano-$C_{1-6}$ alkyl, nitro$C_{1-6}$ alkyl, $C_{3-8}$ cycloalkyl-$C_{1-6}$ alkyl, $C_{3-8}$ heterocycloalkyl-$C_{1-6}$ alkyl, $C_{1-6}$ alkoxy-$C_{1-6}$ alkyl, mono$C_{1-6}$ alkylamino, mono$C_{1-6}$ alkylamino-$C_{1-6}$ alkyl, di$C_{1-6}$ alkylamino, di$C_{1-6}$ alkylamino-$C_{1-6}$ alkyl, $C_{1-6}$ alkylacyl, $C_{1-6}$ alkylacyl-$C_{1-6}$ alkyl, $C_{1-6}$ alkoxyacyl, $C_{1-6}$ alkoxyacyl-$C_{1-6}$ alkyl, $C_{1-6}$ alkylacyloxy, $C_{1-6}$ alkylacyloxy-$C_{1-6}$ alkyl, aminoacyl, aminoacyl-$C_{1-6}$ alkyl, mono$C_{1-6}$ alkylaminoacyl, mono$C_{1-6}$ alkylaminoacyl-$C_{1-6}$ alkyl, di$C_{1-6}$ alkylaminoacyl, di$C_{1-6}$ alkylaminoacyl-$C_{1-6}$ alkyl, $C_{1-6}$ alkylacylamino and $C_{1-6}$ alkylacylamino-$C_{1-6}$ alkyl;

further preferably, each of $L_1$ and $L_2$ is independently selected from the group consisting of the following groups:

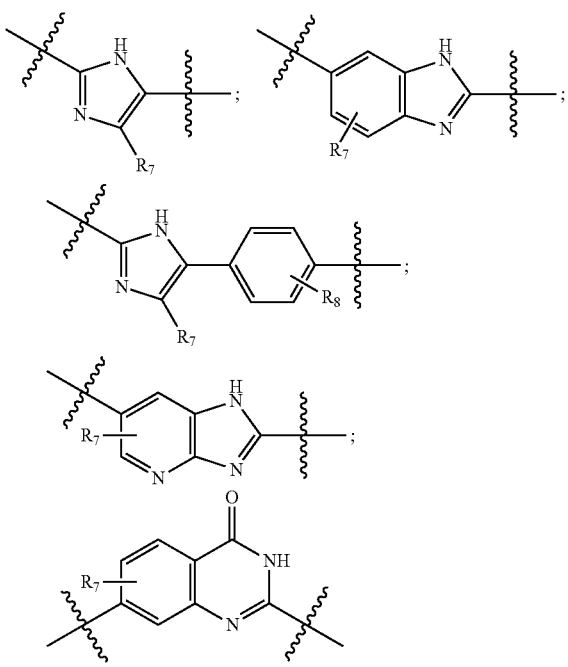

wherein each of $R_7$ and $R_8$ is independently selected from the group consisting of hydrogen, halogen, hydroxyl, amino, carboxyl, cyano, nitro, alkyl, cycloalkyl, heterocycloalkyl, alkoxy, haloalkyl, hydroxyalkyl, aminoalkyl, carboxyalkyl, cyanoalkyl, nitroalkyl, cycloalkylalkyl, heterocycloalkylalkyl, alkoxyalkyl, monoalkylamino, monoalkylaminoalkyl, dialkylamino, dialkylaminoalkyl, alkylacyl, alkylacylalkyl, alkoxyacyl, alkoxyacylalkyl, alkylacyloxy, alkylacyloxyalkyl, aminoacyl, aminoacylalkyl, monoalkylaminoacyl, monoalkylaminoacylalkyl, dialkylaminoacyl, dialkylaminoacylalkyl, alkylacylamino and alkylacylaminoalkyl; preferably, each of $R_7$ and $R_8$ is independently selected from the group consisting of hydrogen, halogen, hydroxyl, amino, carboxyl, cyano, nitro, $C_{1-6}$ alkyl, $C_{3-8}$ cycloalkyl, $C_{3-8}$ heterocycloalkyl, $C_{1-6}$ alkoxy, $C_{1-6}$ haloalkyl, hydroxy-$C_{1-6}$ alkyl, amino-$C_{1-6}$ alkyl, carboxy-$C_{1-6}$ alkyl, cyano-$C_{1-6}$ alkyl, nitro-$C_{1-6}$ alkyl, $C_{3-8}$ cycloalkyl-$C_{1-6}$ alkyl, $C_{3-8}$ heterocycloalkyl-$C_{1-6}$ alkyl, $C_{1-6}$ alkoxy-$C_{1-6}$ alkyl, mono$C_{1-6}$ alkylamino, mono$C_{1-6}$ alkylamino-$C_{1-6}$ alkyl, di$C_{1-6}$ alkylamino, di$C_{1-6}$ alkylamino-$C_{1-6}$ alkyl, $C_{1-6}$ alkylacyl, $C_{1-6}$ alkylacyl-$C_{1-6}$ alkyl, $C_{1-6}$ alkoxyacyl, $C_{1-6}$ alkoxyacyl-$C_{1-6}$ alkyl, $C_{1-6}$ alkylacyloxy, $C_{1-6}$ alkylacyloxy-$C_{1-6}$ alkyl, aminoacyl, aminoacyl-$C_{1-6}$ alkyl, mono$C_{1-6}$ alkylaminoacyl, mono$C_{1-6}$ alkylaminoacyl-$C_{1-6}$ alkyl, di$C_{1-6}$ alkylaminoacyl, di$C_{1-6}$ alkylaminoacyl-$C_{1-6}$ alkyl, $C_{1-6}$ alkylacylamino and $C_{1-6}$ alkylacylamino-$C_{1-6}$ alkyl.

In some preferred embodiments, the compound of the present invention is the compound of general formula I and a pharmaceutically acceptable salt, isomer, solvate, crystal or prodrug thereof, wherein:

each of $R_1$ and $R_2$ is independently selected from the group consisting of hydrogen, $C_{1-10}$ alkyl, $C_{3-8}$ cycloalkyl, $C_{3-8}$ heterocycloalkyl, aryl or heteroaryl, wherein the $C_{1-10}$ alkyl, $C_{3-8}$ cycloalkyl, $C_{3-8}$ heterocycloalkyl, aryl or heteroaryl can be substituted with one or more of halogen, hydroxyl, amino, carboxyl, cyano, nitro, alkyl, cycloalkyl, heterocycloalkyl, alkoxy, hydroxyalkyl, carboxyalkyl, monoalkylamino, dialkylamino, alkylacyl, alkoxyacyl, alkylacyloxy, aminoacyl, monoalkylaminoacyl, dialkylaminoacyl and alkylacylamino group;

preferably, each of $R_1$ and $R_2$ is independently selected from the group consisting of hydrogen, $C_{1-6}$ alkyl, $C_{3-6}$ cycloalkyl, $C_{3-6}$ heterocycloalkyl, aryl or heteroaryl, wherein the $C_{1-6}$ alkyl, $C_{3-6}$ cycloalkyl, $C_{3-6}$ heterocycloalkyl, aryl or heteroaryl can be substituted with one or more of halogen, hydroxyl, amino, carboxyl, cyano, nitro, $C_{1-6}$ alkyl, $C_{1-6}$ cycloalkyl, $C_{1-6}$ heterocycloalkyl, $C_{1-6}$ alkoxy, for example, methoxy, ethoxy and propoxy, hydroxy-$C_{1-6}$ alkyl, carboxy-$C_{1-6}$ alkyl, mono$C_{1-6}$ alkylamino, di$C_{1-6}$ alkylamino, $C_{1-6}$ alkylacyl, $C_{1-6}$ alkoxyacyl, $C_{1-6}$ alkylacyloxy, aminoacyl, mono$C_{1-6}$ alkylaminoacyl, di$C_{1-6}$ alkylaminoacyl and $C_{1-6}$ alkylacylamino;

further preferably, each of $R_1$ and $R_2$ is independently selected from the group consisting of hydrogen, methyl, ethyl, propyl, isopropyl, n-butyl, sec-butyl, isobutyl, tert-butyl, cyclopropyl, cyclobutyl, cyclopentyl, cyclohexyl, tetrahydropyrrolyl, tetrahydrofuranyl, tetrahydrothienyl, tetrahydrothiazolyl, tetrahydrooxazolyl, piperidinyl, piperazinyl, N-alkylpiperazinyl, phenyl, naphthyl, pyrrolyl, thienyl, thiazolyl, oxazolyl and pyridyl, wherein the methyl, ethyl, propyl, isopropyl, n-butyl, sec-butyl, isobutyl, tert-butyl, cyclopropyl, cyclobutyl, cyclopentyl, cyclohexyl, cycloheptyl, tetrahydropyrrolyl, tetrahydrofuranyl, tetrahydrothienyl, tetrahydrothiazolyl, tetrahydrooxazolyl, piperidinyl, piperazinyl, N-alkylpiperazinyl, phenyl, naphthyl, pyrrolyl, thienyl, thiazolyl, oxazolyl and pyridyl can be substituted with one or more of halogen, hydroxyl, amino, carboxyl, cyano, nitro, $C_{1-6}$ alkyl, $C_{1-6}$ alkoxy, for example, methoxy, ethoxy, propoxy, hydroxy-$C_{1-6}$ alkyl, carboxy-$C_{1-6}$ alkyl, mono$C_{1-6}$ alkylamino and di$C_{1-6}$ alkylamino.

In some preferred embodiments, the compound of the present invention is the compound of general formula I and a pharmaceutically acceptable salt, isomer, solvate, crystal or prodrug thereof, wherein:

each of $R_3$ and $R_4$ is independently selected from the group consisting of hydrogen, $C_{1-10}$ alkyl, $C_{3-8}$ cycloalkyl and $C_{3-8}$ heterocycloalkyl, wherein the $C_{1-10}$ alkyl, $C_{3-8}$ cycloalkyl or $C_{3-8}$ heterocycloalkyl can be substituted with one or more of halogen, hydroxyl, amino, carboxyl, cyano, nitro, alkyl, cycloalkyl, heterocycloalkyl, alkoxy, aryl and heteroaryl;

further preferably, each of $R_3$ and $R_4$ is independently selected from the group consisting of hydrogen, $C_{1-6}$ alkyl, $C_{3-7}$ cycloalkyl and $C_{3-7}$ heterocycloalkyl, wherein the $C_{1-6}$ alkyl, $C_{3-7}$ cycloalkyl or $C_{3-7}$ heterocycloalkyl can be substituted with one or more of halogen, hydroxyl, amino, carboxyl, cyano, nitro, $C_{1-6}$ alkyl, $C_{3-7}$ cycloalkyl, $C_{3-7}$ heterocycloalkyl, $C_{1-6}$ alkoxy, aryl and heteroaryl;

further preferably, each of $R_3$ and $R_4$ is independently selected from the group consisting of hydrogen, methyl, ethyl, propyl, isopropyl, n-butyl, sec-butyl, isobutyl, tert-butyl, cyclopropyl, cyclobutyl, cyclopentyl, cyclohexyl, tetrahydropyrrolyl, tetrahydrofuranyl, tetrahydrothienyl, tetrahydrothiazolyl, tetrahydrooxazolyl, piperidinyl and piperazinyl, wherein the methyl, ethyl, propyl, isopropyl, n-butyl, sec-butyl, isobutyl, tert-butyl, cyclopropyl, cyclobutyl, cyclopentyl, cyclohexyl, tetrahydropyrrolyl, tetrahydrofuranyl, tetrahydrothienyl, tetrahydrothiazolyl, tetrahydrooxazolyl, piperidinyl and piperazinyl can be substituted with one or more of halogen, hydroxyl, amino, carboxyl, cyano, nitro, $C_{1-6}$ alkyl, cyclopropyl, cyclobutyl, cyclopentyl, cyclohexyl, tetrahydropyrrolyl, tetrahydrofuranyl, tetrahydrothienyl, tetrahydrothiazolyl, tetrahydrooxazolyl, piperidinyl, piperazinyl, N-alkylpiperazinyl, $C_{1-6}$ alkyl, phenyl and heteroaryl.

In some preferred embodiments, the compound of the present invention is the compound of general formula I and a pharmaceutically acceptable salt, isomer, solvate, crystal or prodrug thereof, wherein:

each of $R_5$ and $R_6$ is independently selected from the group consisting of hydrogen, cyano, hydroxyl, amino, $C_{1-10}$ alkyl, $C_{3-8}$ cycloalkyl, $C_{3-8}$ heterocycloalkyl, halogen, $C_{1-6}$ alkoxy-$C_{1-6}$ alkyl, aryl and heteroaryl, wherein each of m and n is independently selected from the group consisting of 1, 2 and 3, and when m or n is 2, each $R_5$ or $R_6$ together with the C atom to which they are attached can form a $C_{3-8}$ cycloalkyl or $C_{3-8}$ heterocycloalkyl; wherein the hydroxyl, amino, $C_{1-10}$ alkyl, $C_{3-8}$ cycloalkyl, $C_{3-8}$ heterocycloalkyl, halogen, $C_{1-6}$ alkoxy-$C_{1-6}$ alkyl group, aryl and heteroaryl can be substituted with one or more of halogen, hydroxyl, amino, carboxyl, cyano, nitro, alkyl, cycloalkyl, heterocycloalkyl, alkoxy, hydroxyalkyl, carboxyalkyl, monoalkylamino, dialkylamino, alkylacyl, alkoxyacyl, alkylacyloxy, aminoacyl, monoalkylaminoacyl, dialkylaminoacyl and alkylacylamino group;

preferably, each of $R_5$ and $R_6$ is independently selected from the group consisting of hydrogen, cyano, hydroxyl, amino, $C_{1-6}$ alkyl, $C_{3-7}$ cycloalkyl, $C_{3-7}$ heterocycloalkyl, halogen, $C_{1-6}$ alkoxy-$C_{1-6}$ alkyl, aryl, heteroaryl, wherein each of m and n is independently selected from the group consisting of 1, 2 and 3, and when m or n is 2, each $R_5$ or $R_6$ together with the C atom to which they are attached can form a $C_{3-6}$ cycloalkyl or $C_{3-6}$ heterocycloalkyl; wherein the hydroxyl, amino, $C_{1-6}$ alkyl, $C_{3-7}$ cycloalkyl, $C_{3-7}$ heterocycloalkyl, halogen, $C_{1-6}$ alkoxy-$C_{1-6}$ alkyl group, aryl and heteroaryl can be substituted with one or more of halogen, hydroxyl, amino, carboxyl, cyano, nitro, alkyl, cycloalkyl, heterocycloalkyl, alkoxy, hydroxyalkyl, carboxyalkyl, monoalkylamino, dialkylamino, alkylacyl, alkoxyacyl, alkylacyloxy, aminoacyl, monoalkylaminoacyl, dialkylaminoacyl and alkylacylamino group;

further preferably, each of $R_5$ and $R_6$ is independently selected from the group consisting of hydrogen, cyano, hydroxyl, amino, methyl, ethyl, propyl, isopropyl, n-butyl, sec-butyl, isobutyl, tert-butyl, cyclopropyl, cyclobutyl, cyclopentyl, cyclohexyl, tetrahydropyrrolyl, tetrahydrofuranyl, tetrahydrothienyl, tetrahydrothiazolyl, tetrahydrooxazolyl, 1,3-dioxolanyl, piperidinyl, piperazinyl, N-alkylpiperazinyl, 1,3-dioxanyl, fluorine, chlorine, methoxymethyl, methoxyethyl, methoxypropyl, ethoxymethyl, ethoxyethyl, ethoxypropyl, phenyl, naphthyl, pyrrolyl, thienyl, thiazolyl, oxazolyl and pyridinyl, or when m or n is 2,

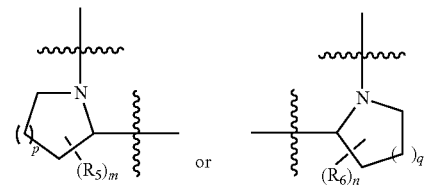

is each independently selected from the group consisting of azaspiroalkyl (e.g., azaspiro[2.4]heptyl, azaspiro[3.4]octyl, azaspiro[4.4]nonyl, azaspiro[2.5]octyl, azaspiro[3.5]nonyl, azaspiro[4.5]decyl, azaspiro[2.6]nonyl and azaspiro[3.6]decyl), oxaazaspiroalkyl (e.g., oxa-azaspiro[2.4]heptyl, oxa-azaspiro[3.4]octyl, oxa-azaspiro[4.4]nonyl, di oxa-azaspiro[4.4]nonyl, oxa-azaspiro[4.5]decyl, dioxa-azaspiro[4.5]decyl and trioxa-azaspiro[4.5]decyl), azabicycloalkyl (e.g., azabicyclo[3.1.0]hexane, azabicyclo[3.2.0]heptyl, octahydrocyclopentapyrrolyl, octahydro-1H-isoindolyl, octahydro-1H-indolyl and azabicyclo[2.2.1]heptyl); wherein the hydroxyl, amino, methyl, ethyl, propyl, isopropyl, n-butyl, sec-butyl, isobutyl, tert-butyl, cyclopropyl, cyclobutyl, cyclopentyl, cyclohexyl, tetrahydropyrrolyl, tetrahydrofuranyl, tetrahydrothienyl, tetrahydrothiazolyl, tetrahydrooxazolyl, 1,3-dioxolanyl, piperidinyl, piperazinyl, N-alkylpiperazinyl, 1,3-dioxanyl, fluorine, chlorine, methoxymethyl, methoxyethyl, methoxypropyl, ethoxymethyl, ethoxyethyl, ethoxypropyl, phenyl, naphthyl, pyrrolyl, thienyl, thiazolyl, oxazolyl and pyridinyl, or when m or n is 2, the azaspiroalkyl (e.g. azaspiro[2.4]heptyl, azaspiro[3.4]octyl, azaspiro[4.4]nonyl, azaspiro[2.5]octyl, azaspiro[3.5]nonyl, azaspiro[4.5]decyl, azaspiro[2.6]nonyl and azaspiro[3.6]decyl), oxaazaspiroalkyl (e.g. oxa-azaspiro[2.4]heptyl, oxa-azaspiro[3.4]octyl, oxa-azaspiro[4.4]nonyl, dioxa-azaspiro[4.4]nonyl, oxa-azaspiro[4.5]decyl, dioxa-azaspiro[4.5]decyl and trioxa-azaspiro[4.5]decyl), azabicycloalkyl (e.g., azabicyclo[3.1.0]hexane, azabicyclo[3.2.0]heptyl, octahydrocyclopentapyrrolyl, octahydro-1H-isoindolyl, octahydro-1H-indolyl and azabicyclo[2.2.1]heptyl) can be substituted with one or more of halogen, hydroxyl, amino, carboxyl, cyano, nitro, alkyl, cycloalkyl, heterocycloalkyl, alkoxy, hydroxyalkyl, carboxyalkyl, monoalkylamino, dialkylamino, alkylacyl, alkoxyacyl, alkylacyloxy, aminoacyl, monoalkylaminoacyl, dialkylaminoacyl and alkylacylamino.

In some specific embodiments, the present invention provides a compound of general formula I or a pharmaceutically acceptable salt, isomer, solvate, crystal or prodrug thereof, wherein

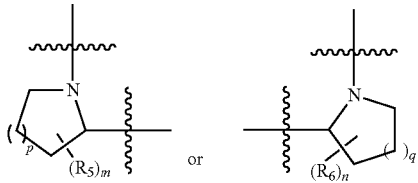

is each independently selected from the group consisting of substituted or unsubstituted

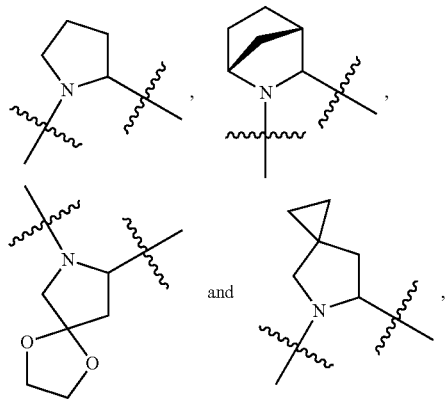

wherein the substituent is selected from the group consisting of halogen, hydroxyl, amino, carboxyl, cyano, nitro, alkyl, cycloalkyl, heterocycloalkyl, alkoxy, hydroxyalkyl, carboxyalkyl, monoalkylamino, dialkylamino, alkylacyl, alkoxyacyl, alkylacyloxy, aminoacyl, monoalkylaminoacyl, dialkylaminoacyl and alkylacylamino.

In some preferred embodiments, the present invention provides a compound of general formula Ia or a pharmaceutically acceptable salt, isomer, solvate, crystal or prodrug thereof, heterocycloalkylalkyl, alkoxyalkyl, monoalkylamino, monoalkylaminoalkyl, dialkylamino, dialkylaminoalkyl, alkylacyl, alkylacylalkyl, alkoxyacyl, alkoxyacylalkyl, alkylacyloxy, alkylacyloxyalkyl, aminoacyl, aminoacylalkyl, mono alkylaminoacyl, monoalkylaminoacylalkyl, dialkylaminoacyl, dialkylaminoacylalkyl, alkylacylamino and alkylacylaminoalkyl;

each of p and q is independently selected from the group consisting of 1, 2 and 3;

each of $R_1$ and $R_2$ is independently selected from the group consisting of hydrogen, alkyl, cycloalkyl, heterocycloalkyl, aryl or heteroaryl, wherein the alkyl, cycloalkyl, heterocycloalkyl, aryl or heteroaryl can be substituted with one or more of halogen, hydroxyl, amino, carboxyl, cyano, nitro, alkyl, cycloalkyl, heterocycloalkyl, alkoxy, haloalkyl, hydroxyalkyl, carboxyalkyl, monoalkylamino, dialkylamino, alkylacyl, alkoxyacyl, alkylacyloxy, aminoacyl, monoalkylaminoacyl, dialkylaminoacyl and alkylacylamino;

each of $R_3$ and $R_4$ is independently selected from the group consisting of hydrogen, alkyl, cycloalkyl and heterocycloalkyl, wherein the alkyl, cycloalkyl or heterocycloalkyl can be substituted with one or more of halogen, hydroxyl, amino, carboxyl, cyano, nitro, alkyl, cycloalkyl, heterocycloalkyl, alkoxy, aryl and heteroaryl; and each of $R_5$ and $R_6$ is independently selected from the group consisting of hydrogen, halogen, hydroxyl, amino, carboxyl, cyano, nitro, alkyl, cycloalkyl, heterocycloalkyl, alkoxy, alkoxyalkyl, aryl and heteroaryl, wherein each of m and n is independently selected from the group consisting of 1, 2 and 3, and when m or n is 2, each $R_5$ or $R_6$ together with the C atom to which they are attached can form a cycloalkyl or heterocycloalkyl; wherein the hydroxyl, amino, carboxyl, alkyl, cycloalkyl, heterocycloalkyl, alkoxy, alkoxyalkyl, aryl and heteroaryl can be substituted with one or more of halogen, hydroxyl, amino, carboxyl, cyano, nitro, alkyl, cycloalkyl, heterocycloalkyl, alkoxy, hydroxyalkyl, carboxyalkyl, monoalkylamino, dialkylamino, alkylacyl, alkoxyacyl, alkylacyloxy, aminoacyl, monoalkylaminoacyl, dialkylaminoacyl and alkylacylamino.

According to the present invention, in some preferred embodiments, the compound of the present invention is the compound of general formula I or general formula Ia, or a pharmaceutically acceptable salt, isomer, solvate, crystal or prodrug thereof, wherein:

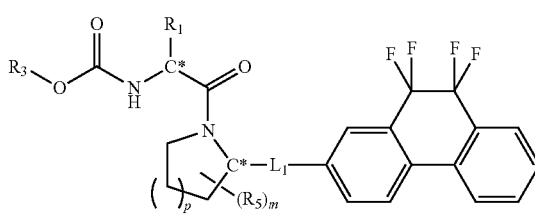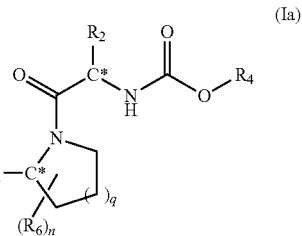

(Ia)

wherein:

C* is in S configuration;

each of $L_1$ and $L_2$ is independently selected from the group consisting of aryl, heteroaryl, -aryl-aryl-, -aryl-heteroaryl- or -heteroaryl-heteroaryl-, wherein the aryl or heteroaryl can be substituted with one or more of halogen, hydroxyl, amino, carboxyl, cyano, nitro, alkyl, cycloalkyl, heterocycloalkyl, alkoxy, haloalkyl, hydroxyalkyl, aminoalkyl, carboxyalkyl, cyanoalkyl, nitroalkyl, cycloalkylalkyl, each of p and q is independently selected from the group consisting of 1, 2 and 3;

each of $L_1$ and $L_2$ is independently selected from the group consisting of phenyl, naphthyl, imidazolyl, benzimidazolyl, -phenyl-imidazolyl-, imidazopyridyl, quinazolinonyl, pyrrolyl, imidazolonyl, furanyl, thienyl, pyrazolyl, oxazolyl, thiazolyl, isoxazolyl, isothiazolyl, oxadiazolyl and triazolyl, wherein the phenyl, naphthyl, imidazolyl, benzimidazolyl, -phenyl-imidazolyl-, imidazopyridyl, quinazolinonyl, pyrrolyl, imidazolonyl, furanyl, thienyl, pyrazolyl, oxazolyl, thiazolyl, isoxazolyl, isothiazolyl, oxadiazolyl and triazolyl can be substituted with one or more of halogen, hydroxyl, amino, carboxyl, cyano, nitro, $C_{1-6}$ alkyl, $C_{3-8}$ cycloalkyl, $C_{3-8}$ heterocycloalkyl, $C_{1-6}$ alkoxy, $C_{1-6}$ haloalkyl, hydroxy-$C_{1-6}$ alkyl, amino-$C_{1-6}$ alkyl, carboxy-$C_{1-6}$ alkyl, cyano-$C_{1-6}$ alkyl, nitro$C_{1-6}$ alkyl, $C_{3-8}$ cycloalkyl-$C_{1-6}$ alkyl, $C_{3-8}$ heterocycloalkyl-$C_{1-6}$ alkyl, $C_{1-6}$ alkoxy-$C_{1-6}$ alkyl, mono$C_{1-6}$ alkylamino, mono$C_{1-6}$ alkylamino-$C_{1-6}$ alkyl, di$C_{1-6}$ alkylamino, di$C_{1-6}$ alkylamino-$C_{1-6}$ alkyl, $C_{1-6}$ alkylacyl, $C_{1-6}$ alkylacyl-$C_{1-6}$ alkyl, $C_{1-6}$ alkoxyacyl, $C_{1-6}$ alkoxyacyl-$C_{1-6}$ alkyl, $C_{1-6}$ alkylacyloxy, $C_{1-6}$ alkylacyloxy-$C_{1-6}$ alkyl, aminoacyl, aminoacyl-$C_{1-6}$ alkyl, mono$C_{1-6}$ alkylaminoacyl, mono$C_{1-6}$ alkylaminoacyl-$C_{1-6}$ alkyl, di$C_{1-6}$ alkylaminoacyl, di$C_{1-6}$ alkylaminoacyl-$C_{1-6}$ alkyl, $C_{1-6}$ alkylacylamino and $C_{1-6}$ alkylacylamino-$C_{1-6}$ alkyl;

each of $R_1$ and $R_2$ is independently selected from the group consisting of hydrogen, $C_{1-6}$ alkyl, $C_{3-8}$ cycloalkyl, $C_{3-8}$ heterocycloalkyl, aryl or heteroaryl, wherein the $C_{1-6}$ alkyl, $C_{3-8}$ cycloalkyl, $C_{3-8}$ heterocycloalkyl, aryl or heteroaryl can be substituted with one or more of halogen, hydroxyl, amino, carboxyl, cyano, nitro, $C_{1-6}$ alkyl, $C_{1-8}$ cycloalkyl, $C_{1-8}$ heterocycloalkyl, $C_{1-6}$ alkoxy, for example, methoxy, ethoxy and propoxy, hydroxy-$C_{1-6}$ alkyl, carboxy-$C_{1-6}$ alkyl, mono$C_{1-6}$ alkylamino, di$C_{1-6}$ alkylamino, $C_{1-6}$ alkylacyl, $C_{1-6}$ alkoxyacyl, $C_{1-6}$ alkylacyloxy, aminoacyl, mono$C_{1-6}$ alkylaminoacyl, di$C_{1-6}$ alkylaminoacyl and $C_{1-6}$ alkylacylamino.

each of $R_3$ and $R_4$ is independently selected from the group consisting of hydrogen, $C_{1-6}$ alkyl, $C_{3-8}$ cycloalkyl and $C_{3-8}$ heterocycloalkyl, wherein the $C_{1-6}$ alkyl, $C_{3-8}$ cycloalkyl or $C_{3-8}$ heterocycloalkyl can be substituted with one or more of halogen, hydroxyl, amino, carboxyl, cyano, nitro, $C_{1-6}$ alkyl, $C_{3-8}$ cycloalkyl, $C_{3-8}$ heterocycloalkyl, $C_{1-6}$ alkoxy, aryl and heteroaryl;

each of $R_5$ and $R_6$ is independently selected from the group consisting of hydrogen, cyano, hydroxyl, amino, $C_{1-6}$ alkyl, $C_{3-8}$ cycloalkyl, $C_{3-8}$ heterocycloalkyl, halogen, $C_{1-6}$ alkoxy-$C_{1-6}$ alkyl, aryl and heteroaryl, wherein each of m and n is independently selected from the group consisting of 1, 2 and 3, and when m or n is 2, each $R_5$ or $R_6$ together with the C atom to which they are attached can form a $C_{3-8}$ cycloalkyl or $C_{3-8}$ heterocycloalkyl; wherein the hydroxyl, amino, $C_{1-6}$ alkyl, $C_{3-8}$ cycloalkyl, $C_{3-8}$ heterocycloalkyl, halogen, $C_{1-6}$ alkoxy-$C_{1-6}$ alkyl, aryl and heteroaryl can be substituted with one or more of halogen, hydroxyl, amino, carboxyl, cyano, nitro, $C_{1-6}$ alkyl, $C_{3-8}$ cycloalkyl, $C_{3-8}$ heterocycloalkyl, $C_{1-6}$ alkoxy, hydroxy-$C_{1-6}$ alkyl, carboxy-$C_{1-6}$ alkyl, mono$C_{1-6}$ alkylamino, di$C_{1-6}$ alkylamino, $C_{1-6}$ alkylacyl, $C_{1-6}$ alkoxyacyl, $C_{1-6}$ alkylacyloxy, aminoacyl, mono$C_{1-6}$ alkylaminoacyl, di$C_{1-6}$ alkylaminoacyl and $C_{1-6}$ alkylacylamino.

Further preferably, the compound provided by the present invention is the compound of formula I or formula Ia or a pharmaceutically acceptable salt, isomer, solvate, crystal or prodrug thereof, wherein:

each of $L_1$ and $L_2$ is independently selected from the group consisting of the following groups:

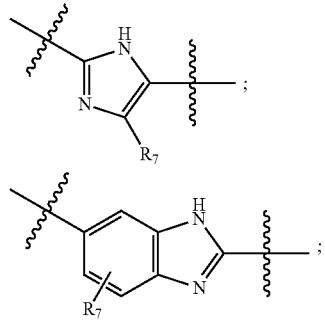

-continued

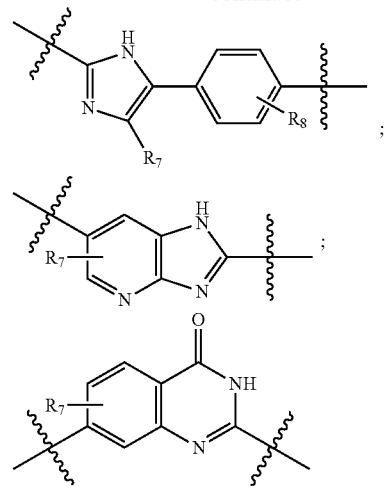

wherein each of $R_7$ and $R_8$ is independently selected from the group consisting of hydrogen, halogen, $C_{1-6}$ alkyl, $C_{1-6}$ alkoxy, $C_{1-6}$ haloalkyl, hydroxy-$C_{1-6}$ alkyl, $C_{1-6}$ alkoxy-$C_{1-6}$ alkyl;

each of p and q is independently selected from the group consisting of 1 and 2;

each of $R_1$ and $R_2$ is independently selected from the group consisting of hydrogen, methyl, ethyl, propyl, isopropyl, n-butyl, sec-butyl, isobutyl, tert-butyl, cyclopropyl, cyclobutyl, cyclopentyl, cyclohexyl and phenyl, wherein the methyl, ethyl, propyl, isopropyl, n-butyl, sec-butyl, isobutyl, tert-butyl, cyclopropyl, cyclobutyl, cyclopentyl, cyclohexyl and phenyl can be substituted with one or more of halogen, hydroxyl, amino, carboxyl, cyano, nitro, $C_{1-6}$ alkyl, $C_{3-6}$ cycloalkyl, $C_{3-6}$ heterocycloalkyl, $C_{1-6}$ alkoxy, for example, methoxy, ethoxy, propoxy, hydroxy-$C_{1-6}$ alkyl, carboxy-$C_{1-6}$ alkyl, mono$C_{1-6}$ alkylamino, di$C_{1-6}$ alkylamino, $C_{1-6}$ alkylacyl, $C_{1-6}$ alkoxyacyl, $C_{1-6}$ alkylacyloxy, aminoacyl, mono$C_{1-6}$ alkylaminoacyl, di$C_{1-6}$ alkylaminoacyl and $C_{1-6}$ alkylacylamino;

each of $R_3$ and $R_4$ is independently selected from the group consisting of hydrogen, $C_{1-6}$ alkyl, $C_{3-6}$ cycloalkyl, $C_{3-6}$ cycloalkyl-$C_{1-6}$ alkyl-, $C_{3-6}$ heterocycloalkyl, $C_{3-6}$ heterocycloalkyl-$C_{1-6}$ alkyl-, wherein the $C_{1-6}$ alkyl, $C_{3-6}$ cycloalkyl, $C_{3-6}$ cycloalkyl-$C_{1-6}$ alkyl-, $C_{3-6}$ heterocycloalkyl, $C_{3-6}$ heterocycloalkyl-$C_{1-6}$ alkyl can be substituted with one or more of halogen, hydroxyl, amino, carboxyl, cyano, nitro, $C_{1-6}$ alkyl, $C_{1-6}$ alkoxy, aryl and heteroaryl;

each of $R_5$ and $R_6$ is independently selected from the group consisting of hydrogen, halogen, cyano, hydroxyl, amino, carboxyl, nitro, $C_{1-6}$ alkyl, $C_{3-6}$ cycloalkyl, $C_{3-6}$ heterocycloalkyl, $C_{1-6}$ alkoxyhaloalkyl, cyano$C_{1-6}$ alkyl, hydroxy$C_{1-6}$ alkyl, amino-$C_{1-6}$ alkyl, carboxy$C_{1-6}$ alkyl, nitro-$C_{1-6}$ alkyl, $C_{3-6}$ cycloalkyl-$C_{1-6}$ alkyl, $C_{3-6}$ heterocycloalkyl-$C_{1-6}$ alkyl, or when m or n is 2,

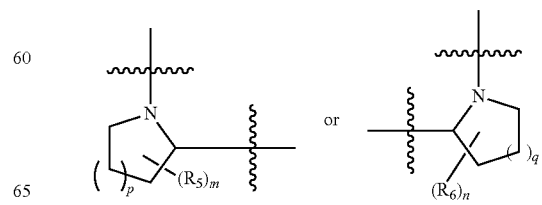

is each independently selected from the group consisting of azaspiroalkyl (e.g. azaspiro[2.4]heptyl, azaspiro[3.4]octyl, azaspiro[4.4]nonyl, azaspiro[2.5]octyl, azaspiro[3.5]nonyl, azaspiro[4.5]decyl, azaspiro[2.6]nonyl and azaspiro[3.6]decyl), oxaazaspiroalkyl (e.g. oxa-azaspiro[2.4]heptyl, oxa-azaspiro[3.4]octyl, oxa-azaspiro[4.4]nonyl, dioxa-azaspiro[4.4]nonyl, oxa-azaspiro[4.5]decyl, dioxa-azaspiro[4.5]decyl and trioxa-azaspiro[4.5]decyl), azabicycloalkyl (e.g., azabicyclo[3.1.0]hexane, azabicyclo[3.2.0]heptyl, octahydrocyclopentapyrrolyl, octahydro-1H-isoindolyl, octahydro-1H-indolyl and azabicyclo[2.2.1]heptyl).

In some specific embodiments, the present invention provides the compound of general formula Ia or a pharmaceutically acceptable salt, isomer, solvate, crystal or prodrug thereof, wherein

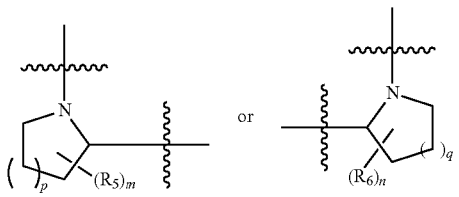

or is each independently selected from the group consisting of submitted or unsubstituted

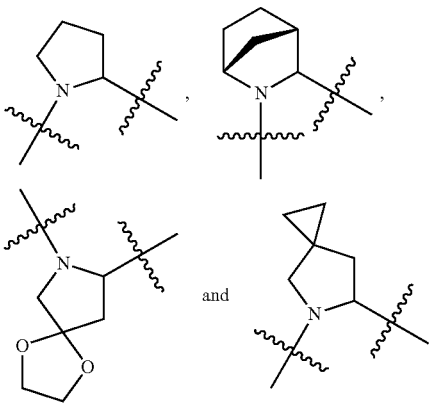

and

The present invention provides the following specific compounds:

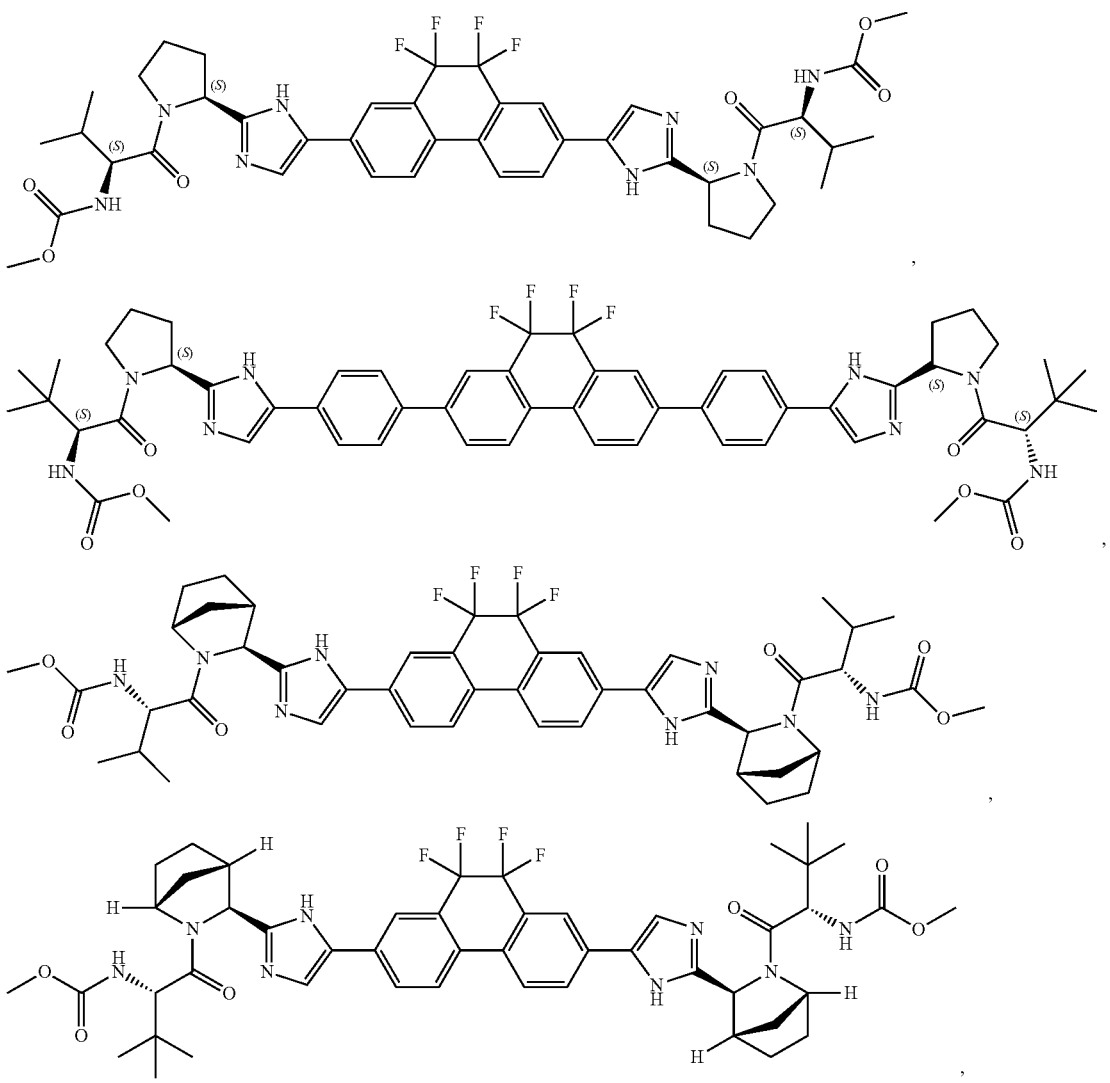

-continued
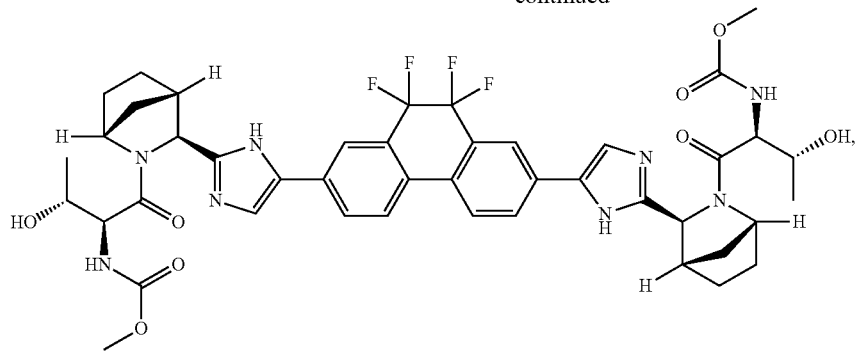
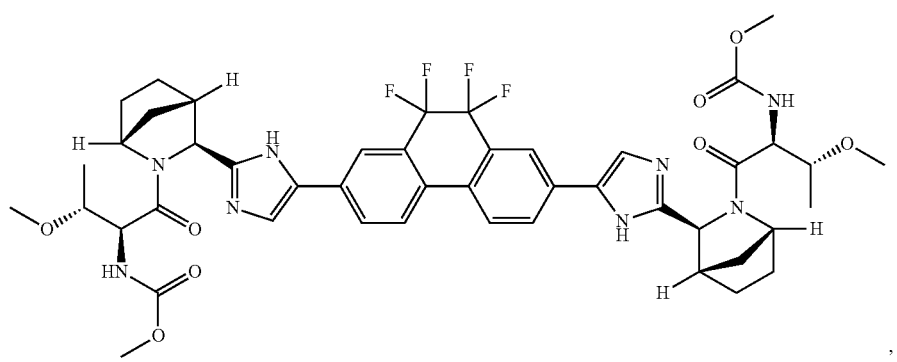
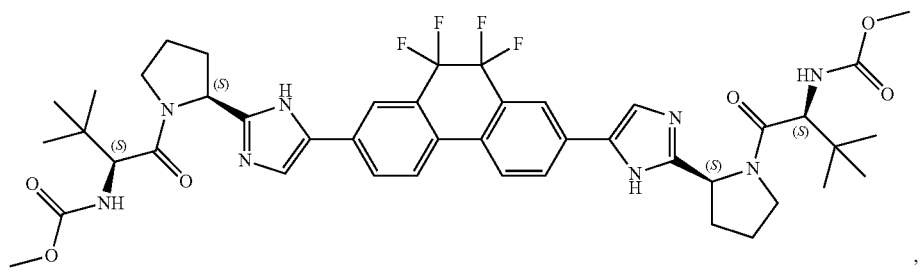
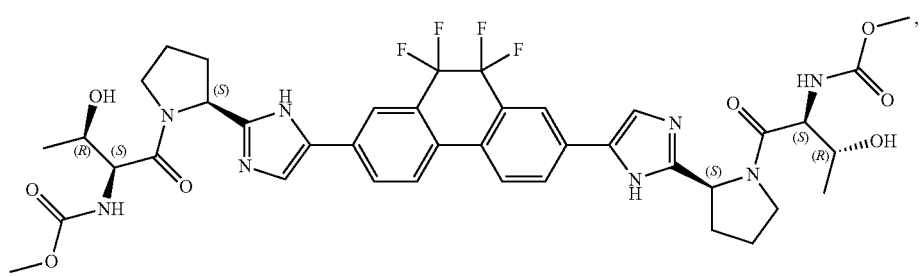
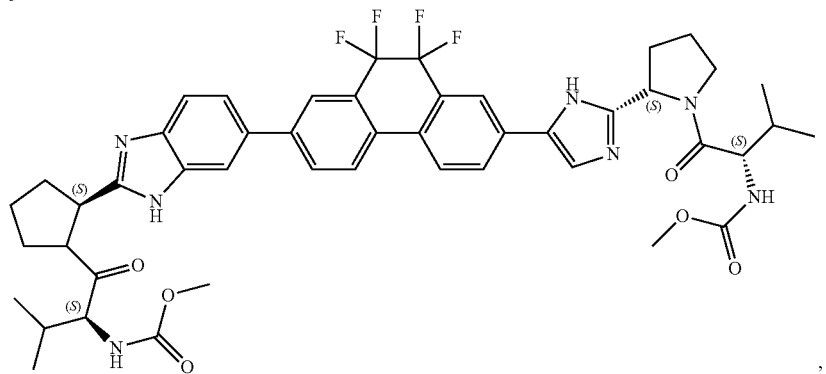

-continued
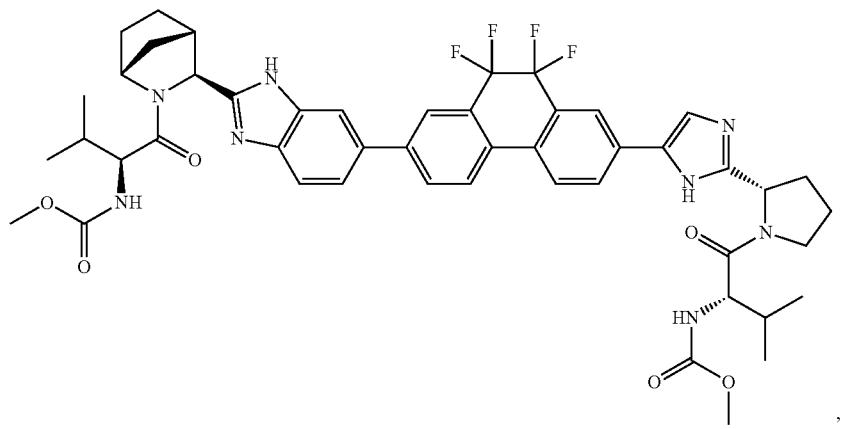
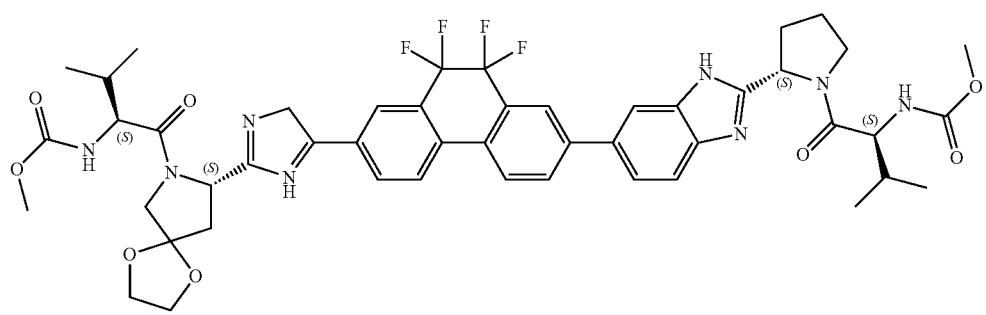
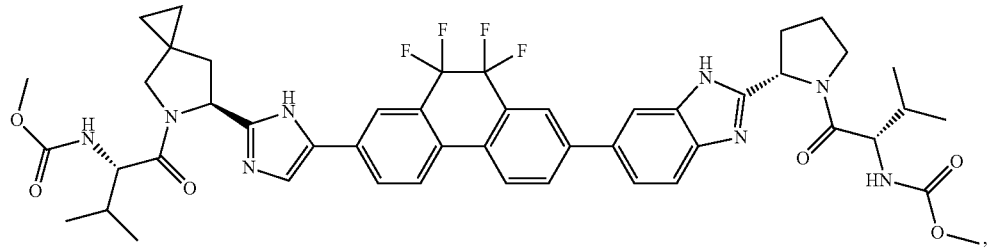
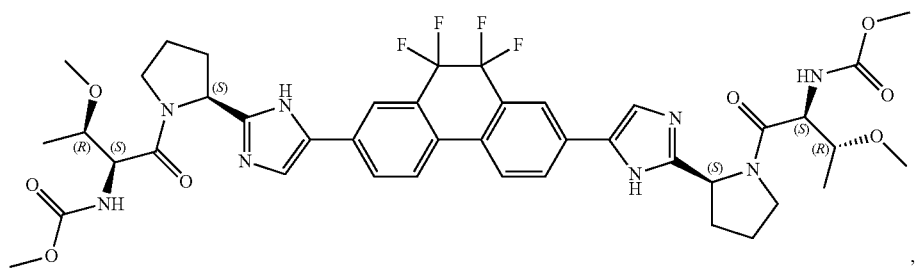
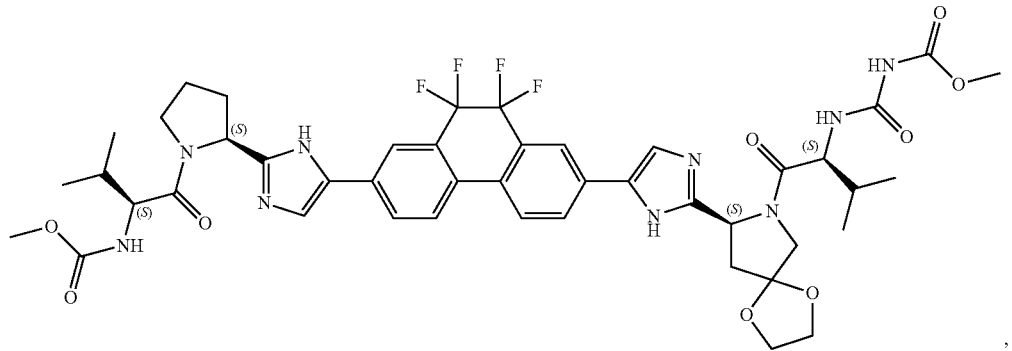

-continued

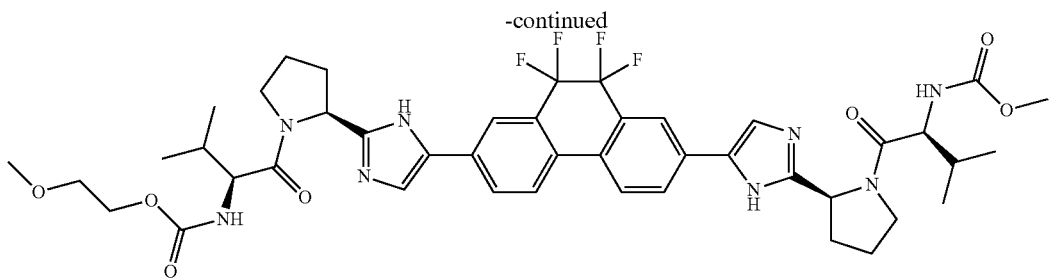

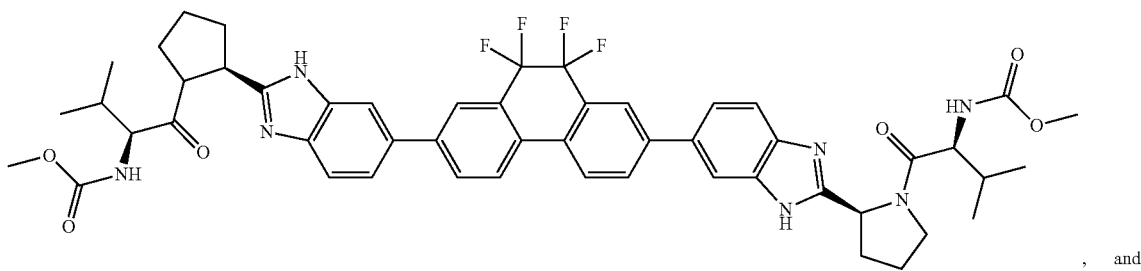

, and

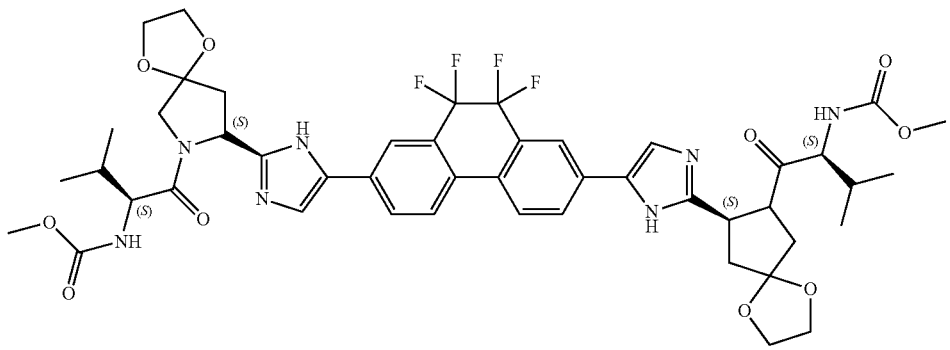

.

The present invention also provides the intermediate of formula (II) in the preparation of the compound of the present invention or a pharmaceutically acceptable salt, isomer, solvate, crystal or prodrug thereof:

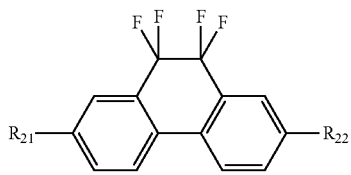

(II)

wherein, each of $R_{21}$ and $R_{22}$ is independently selected from the group consisting of hydrogen, halogen, trifluoromethanesulfonate group, mesylate group, p-tosylate group and

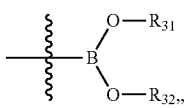

wherein each of $R_{31}$ and $R_{32}$ is independently selected from the group consisting of hydrogen, $C_{1-6}$ alkyl, or $R_{31}$ and $R_{32}$ are cyclized together with the atom attached thereto to constitute a 5- to 7-membered heterocycle optionally substituted with one or more of $C_{1-6}$ alkyl, halogen, amino, carboxyl, cyano, nitro, or $C_{1-6}$ alkoxy; preferably, each of $R_{21}$ and $R_{22}$ is independently selected from the group consisting of hydrogen, chlorine, bromine, iodine or

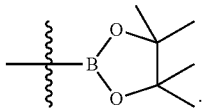 [SMILES: *B1OC(C)(C)C(C)(C)O1]

.

In another aspect, the present invention provides a method for preparing the compound of the general formula of the present invention. The method for preparing the compound of general formula I comprises the following steps:

(1) preparing the intermediate of formula (3):

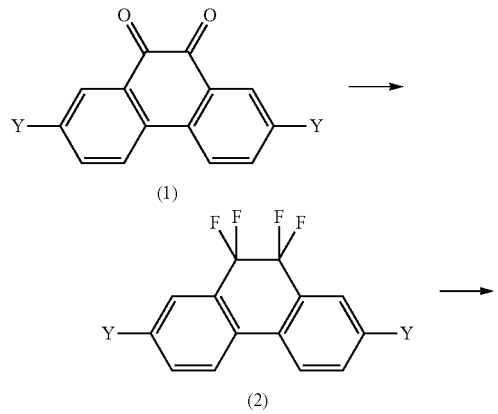

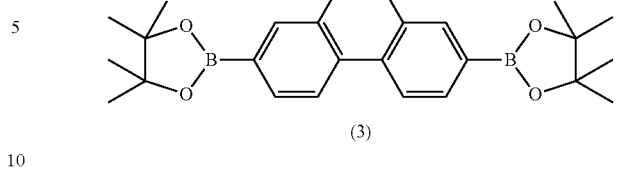

a) subjecting the compound of formula (1) to a fluorination reaction to obtain the intermediate of formula (2); and b) reacting the intermediate of formula (2) with bis(pinacolato)diboron to obtain the intermediate of formula (3);

(2) preparing the compound of general formula (I):

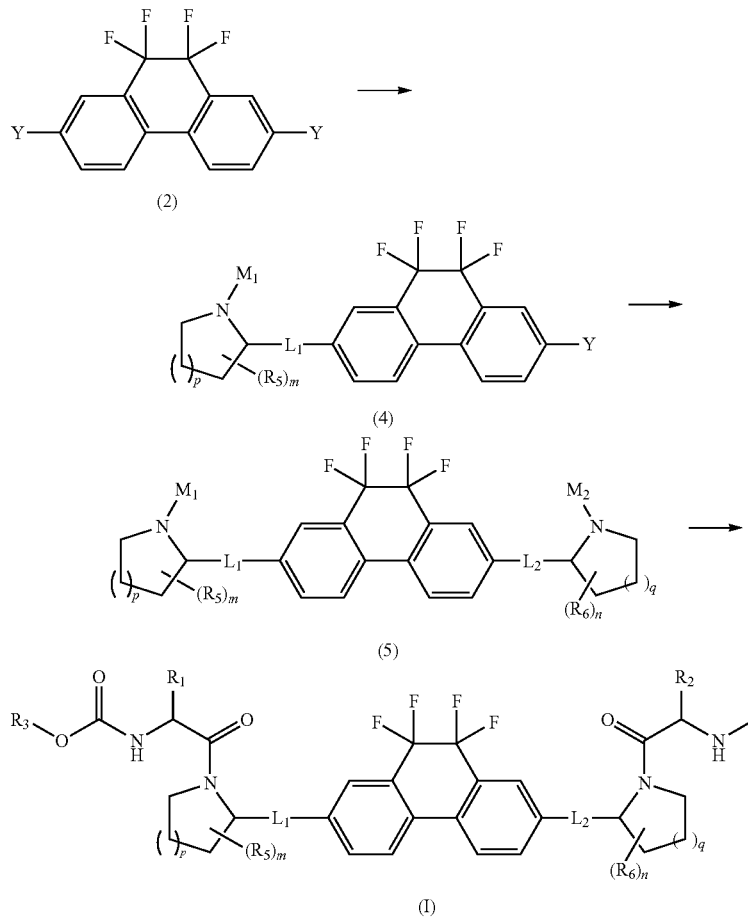

or

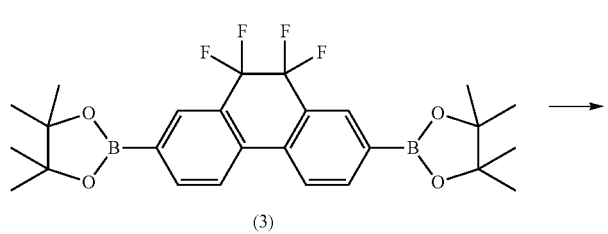

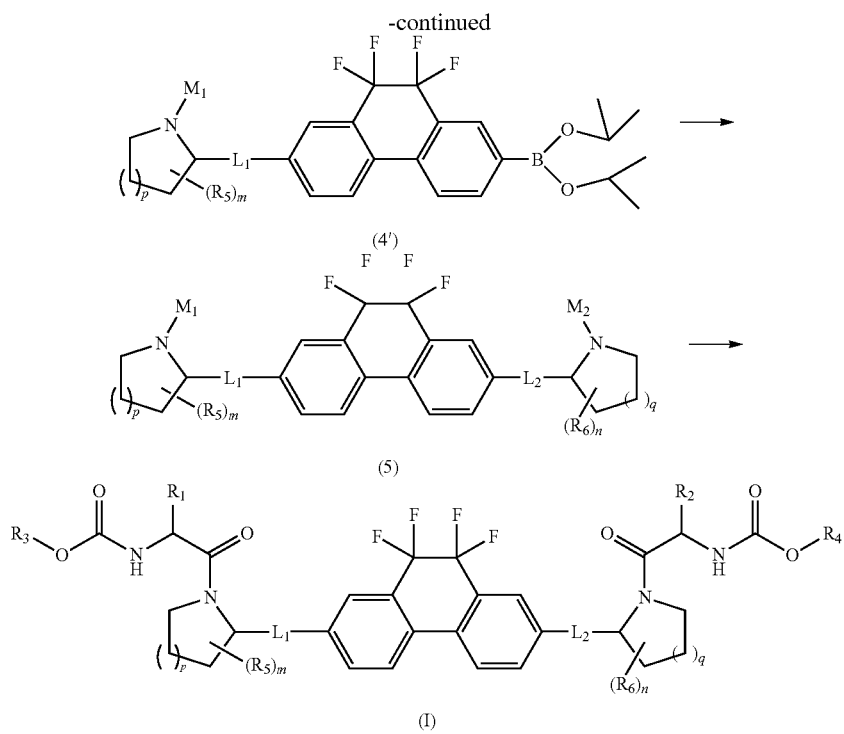

c) subjecting the intermediate of formula (2) to a coupling reaction to obtain the intermediate of formula (4), or subjecting the intermediate of formula (3) to a coupling reaction to obtain the intermediate of formula (4');

d) subjecting the intermediate of formula (4) or (4') to a coupling reaction to obtain the intermediate of formula (5), and if necessary, comprising a step of removing the protecting group;

e) subjecting the intermediate of formula (5) to amidation to obtain the compound of general formula (I), and if necessary, comprising a step of removing the protecting group.

Wherein $R_1$, $R_2$, $R_3$, $R_4$, $R_5$, $R_6$, $L_1$ and $L_2$ have the meanings as defined for formula I, $M_1$ represents hydrogen, trimethylsilylethoxy or tert-butoxycarbonyl, $M_2$ represents hydrogen, trimethylsilylethoxy or tert-butoxycarbonyl, and Y represents halogen, preferably chlorine, bromine and iodine.

In particular, for the preparation of the compound of general formula I wherein at least one of $L_1$ or $L_2$ is selected from imidazolyl, the following method can also be used, comprising:

(1) preparing the intermediate of formula (106):

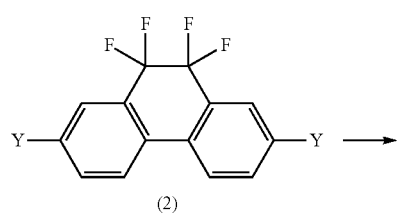

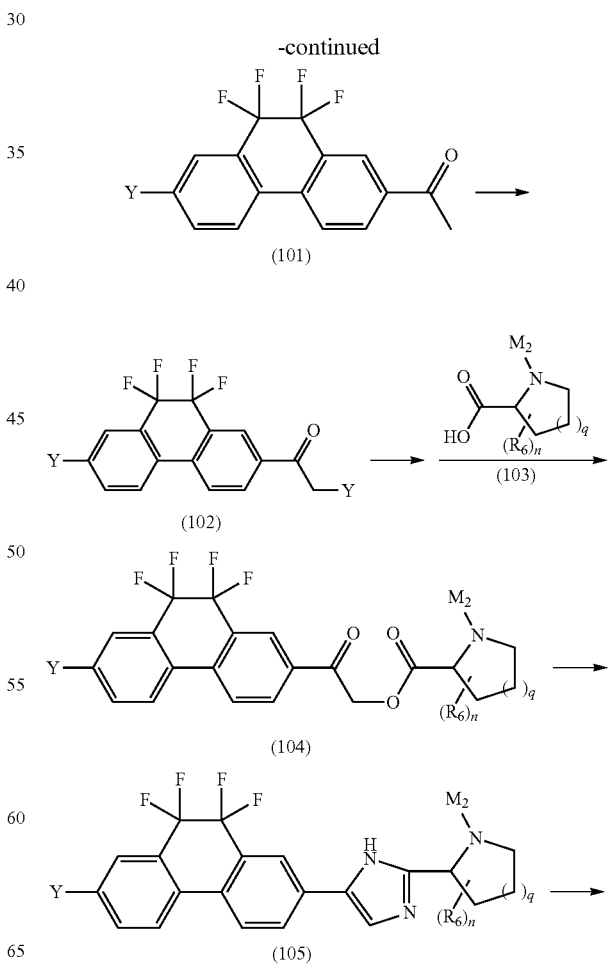

-continued

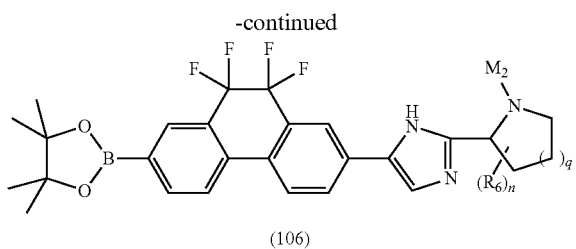

(106)

b-1) subjecting the intermediate of formula (2) to a Stille reaction and an acid-catalyzed hydrolysis reaction to obtain the intermediate of formula (101);

b-2) subjecting the intermediate of formula (101) to a halogenation reaction to obtain the intermediate of formula (102);

b-3) reacting the intermediate of formula (102) with the intermediate of formula (103) to obtain the intermediate of formula (104);

b-4) subjecting the intermediate of formula (104) to the action of an ammonia source; and b-5) reacting the intermediate of formula (105) with bis(pinacolato)diboron to obtain the intermediate of formula (106); and (2) preparing the compound of general formula I wherein at least one of $L_1$ or $L_2$ is selected from imidazolyl:

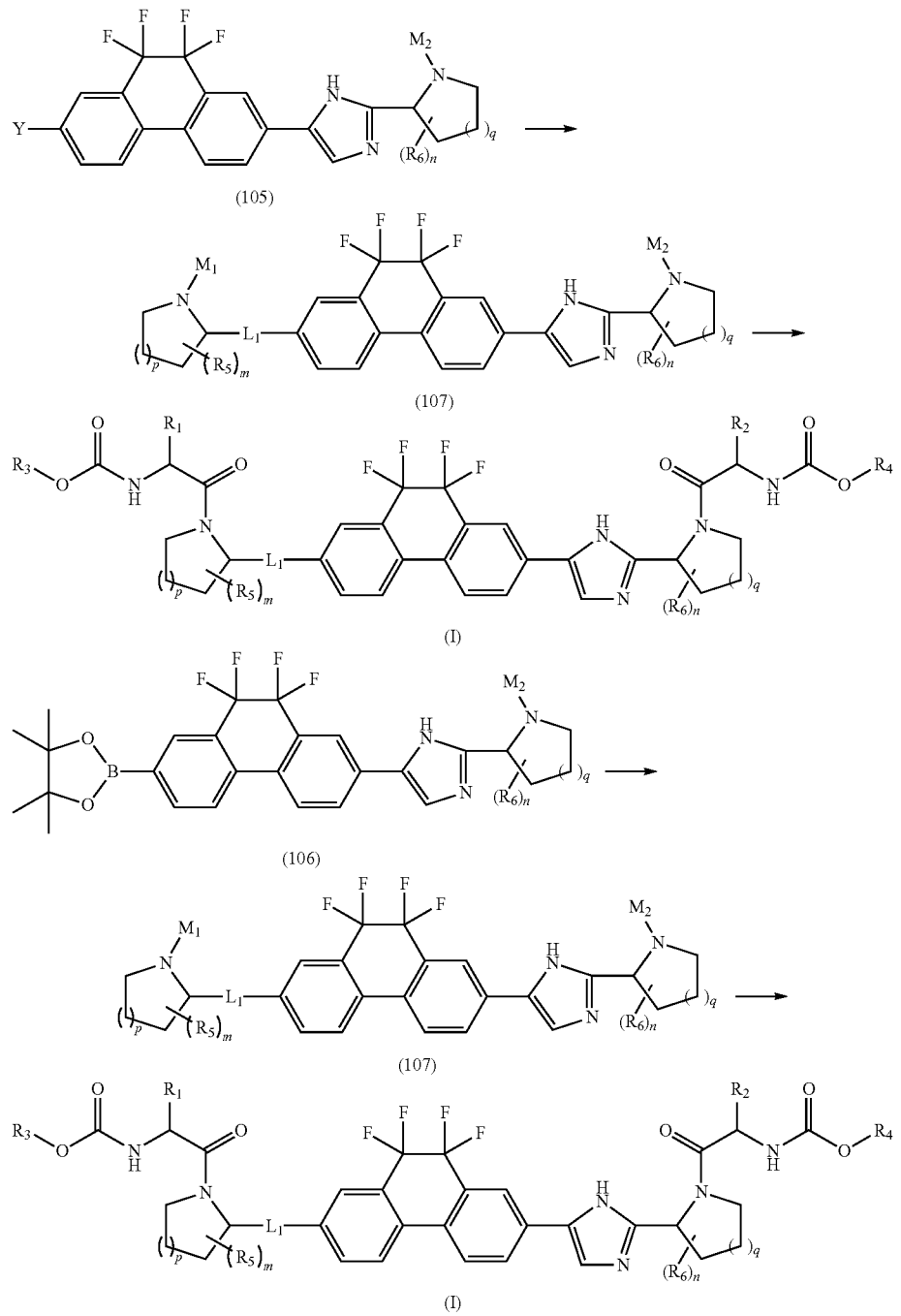

b-6) subjecting the intermediate of formula (105) to a coupling reaction to obtain the intermediate of formula (107), or subjecting the intermediate of formula (106) to a coupling reaction to obtain the intermediate of formula (107), and if necessary, comprising a step of removing the protecting group; and b-7) subjecting the intermediate of formula (107) to amidation to obtain the compound of general formula (I), and if necessary, comprising a step of removing the protecting group.

Wherein $R_1$, $R_2$, $R_3$, $R_4$, $R_5$, $R_6$, $L_1$ and $L_2$ have the meanings as defined for formula I, $M_1$ represents hydrogen, trimethylsilyl ethoxy or tert-butoxycarbonyl, $M_2$ represents hydrogen, trimethylsilylethoxy, or tert-butoxycarbonyl, Y represents halogen, preferably chlorine, bromine or iodine, and the ammonia source refers to aqueous ammonia, ammonia gas or ammonium salt compound, such as ammonium sulfate, ammonium carbonate, ammonium bicarbonate, ammonium acetate, ammonium chloride and the like.

In the third aspect, the present invention provides a pharmaceutical composition comprising the compound of the present invention or a pharmaceutically acceptable salt, isomer, solvate, crystal or prodrug thereof.

In some embodiments, the present invention provides the compound of the present invention or a pharmaceutically acceptable salt, isomer, solvate, crystal or prodrug thereof and the pharmaceutical composition comprising the compound of the present invention or a pharmaceutically acceptable salt, isomer, solvate, crystal or prodrug thereof, for the treatment and/or prevention of a liver disease caused by hepatitis C virus.

In some embodiments, the present invention provides a pharmaceutical composition comprising the compound of the present invention or a pharmaceutically acceptable salt, isomer, solvate, crystal or prodrug thereof, and one or more selected from the group consisting of interferons, triazole nucleoside drugs, glycyrrhizin compound preparation and HCV protease inhibitor.

The compound of the present invention or a pharmaceutically acceptable salt, isomer, solvate, crystal or prodrug thereof can be formulated with a pharmaceutically acceptable carrier, diluent or excipient to prepare a pharmaceutical formulation suitable for oral or parenteral administration. The method for administration includes, but not limited to intradermal, intramuscular, intraperitoneal, intravenous, subcutaneous, intranasal and oral routes. The formulation can be administered by any route, for example by infusion or bolus injection, by route through epithelial or mucocutaneous absorption (e.g., oral mucosa or rectum, etc.). The administration can be systemic or local. Examples of formulations for oral administration include solid or liquid dosage forms, and specifically, include tablet, pill, granule, powder, capsule, syrup, emulsion, suspension and the like. The formulation can be prepared by methods known in the art, and comprises carrier, diluent or excipient conventionally used in the art of pharmaceutical preparation.

In the fourth aspect, the present invention provides a method for the treatment and/or prevention of a liver disease caused by hepatitis C virus with the compound of the present invention or a pharmaceutically acceptable salt, isomer, solvate, crystal or prodrug thereof or the pharmaceutical composition of the present invention, and a use of the preparation of a medication for the prevention and/or treatment of a liver disease caused by hepatitis C virus, comprising administering the compound of the present invention or a pharmaceutically acceptable salt, isomer, solvate, crystal or prodrug thereof or the pharmaceutical composition comprising the compound of the present invention or a pharmaceutically acceptable salt, isomer, solvate, crystal or prodrug thereof to a patient having a liver disease caused by hepatitis C virus to effectively inhibit HCV and to prevent the progression of disease. In some embodiments, the present invention provides a method for treating and/or preventing a infection caused by hepatitis C virus, said method comprises administering a therapeutically and/or prophylactically effective amount of the compound of the present invention or a pharmaceutically acceptable salt, isomer, solvate, crystal or prodrug thereof or the pharmaceutical composition of the present invention to an individual in need thereof. The compound of the present invention or a pharmaceutically acceptable salt, isomer, solvate, crystal or prodrug thereof or the pharmaceutical composition of the present invention may be administered to a mammal in need thereof to inhibit HCV and prevent the progression of disease.

In other embodiments, the method or use for the treatment and/or prevention of an infection caused by hepatitis C virus further comprises administering to the subject the compound of formula I of the present invention or a pharmaceutically acceptable salt, isomer, solvate, crystal or prodrug thereof or the pharmaceutical composition comprising the same, and at least one other compound with anti-HCV activity before, after or simultaneously with the administration of the compound of formula I of the present invention or a pharmaceutically acceptable salt, isomer, solvate, crystal or prodrug thereof or the pharmaceutical composition comprising the same. In some embodiments, said at least one of the other compounds is interferon or ribavirin. In some specific embodiments, the interferon is selected from the group consisting of interferon α2B, PEGylated interferon α, consensus interferon, interferon α2A and lymphoblastoid interferon T. In other embodiments, said at least one of the other compounds is selected from the group consisting of interleukin 2, interleukin 6, interleukin 12, interfering RNA, antisense RNA, imiquimod, ribavirin, inosine 5'-monophosphate dehydrogenase inhibitor, amantadine and rimantadine. In other embodiments, said at least one of the other compounds can effectively inhibit the function of a target to treat HCV infection, wherein said target is selected from the group consisting of HCV metalloprotease, HCV serine protease, HCV polymerase, HCV helicase, HCV NS4B protein, HCV NS5B protein, HCV entry, HCV assembly, HCV release, HCV NS3/4A protein and IMP DH.

DESCRIPTION OF TERMINOLOGY

"Alkyl" as used in the present invention refers to a linear or branched saturated hydrocarbyl group. Suitable alkyl is a substituted or unsubstituted $C_{1-10}$ alkyl, such as methyl, ethyl, n-propyl, isopropyl, cyclopropyl, n-butyl, sec-butyl, isobutyl, tert-butyl, cyclobutyl, n-pentyl, isopentyl, cyclopentyl, cyclohexyl, n-hexyl and the like.

"Cycloalkyl" as used in the present invention refers to a cyclic saturated hydrocarbyl group. Suitable cycloalkyl can be a substituted or unsubstituted monocyclic, bicyclic or tricyclic saturated hydrocarbyl having 3-10 carbon atoms, such as cyclopropyl, cyclobutyl, cyclopentyl or cyclohexyl.

"Alkoxy" as used in the present invention refers to —O-alkyl. According to the present invention, suitable alkoxy is $C_{1-10}$ alkoxy, such as $C_{1-8}$ alkoxy, $C_{1-7}$ alkoxy, $C_{1-6}$ alkoxy, $C_{1-5}$ alkoxy, $C_{1-4}$ alkoxy alkoxy and $C_{1-3}$ alkoxy, including methoxy, ethoxy, propoxy, isopropoxy, isobutoxy, sec-butoxy and the like.

"Halogen" as used in the present invention refers to fluorine, chlorine, bromine and iodine.

"Haloalkyl" as used in the present invention refers to alkyl substituted with at least one halogen.

"Haloalkoxy" as used in the present invention refers to alkoxy substituted with at least one halogen.

"Aminoacyl" as used in the present invention refers to —C(O)—NH$_2$.

"Monoalkylaminoacyl" as used in the present invention refers to —C(O)—NH-alkyl.

"Dialkylaminoacyl" as used in the present invention refers to —C(O)—N(alkyl)(alkyl).

"Aryl" as used in the present invention refers to an aromatic system, which can comprise single ring or multiple fused rings, such as bicyclic or tricyclic aromatic ring, wherein at least part of the fused ring forms a conjugated aromatic system, and comprises 5-50 carbon atoms, preferably about 6 to about 14 carbon atoms. Suitable aryl includes, but are not limited to, phenyl, naphthyl, biphenyl, anthryl, tetrahydronaphthyl, fluorenyl, indanyl, biphenylenyl and acenaphthenyl.

"Heteroaryl" as used in the present invention refers to an aromatic group in which at least one carbon atom in the aromatic monocyclic or multiple fused rings, such as bicyclic or tricyclic ring, is replaced by a heteroatom, wherein the heteroatom is O, S or N. Suitable heteroaryl includes, but are not limited to, imidazolyl, benzimidazolyl, imidazopyridyl, quinazolinonyl, pyrrolyl, imidazolonyl, furyl, thienyl, pyrazolyl, oxazolyl, thiazolyl, isoxazolyl, isothiazolyl, oxadiazolyl, triazolyl and the like.

"Solvate" as used in the present invention, in its conventional sense, refers to a complex formed by the combination of a solute (such as an active compound, salt of an active compound) and a solvent (such as water). The solvent refers to a solvent known to or can be readily determined by those skilled in the art. If the solvent is water, the solvate is commonly referred to hydrate, such as monohydrate, dihydrate, trihydrate and the like.

"Crystal" as used in the present invention refers to various solid forms of the compound of the present invention, comprising crystalline and amorphous form.

"Isomer" as used in the present invention refers to a stereoisomer produced by different spatial arrangements of atoms in the molecule, including enantiomer and diastereomer.

"Prodrug" as used in the present invention refers to a compound which, under the physiological condition of the organism, is converted into the compound of the present invention due to reaction with enzyme, gastric acid and the like, i.e., a compound which is converted into the compound of the present invention by oxidation, reduction, hydrolysis and the like under the action of enzyme, and/or a compound which is converted into the compound of the present invention by hydrolysis reaction under the action of gastric acid and the like.

"Pharmaceutically acceptable salt" as used in the present invention refers to a pharmaceutically acceptable salt formed by the compound of the present invention and an acid, wherein the acid includes, but are not limited to, phosphoric acid, sulfuric acid, hydrochloric acid, hydrobromic acid, citric acid, maleic acid, malonic acid, mandelic acid, succinic acid, fumaric acid, acetic acid, lactic acid, nitric acid and the like.

"Pharmaceutical composition" as used in the present invention refers to a mixture comprising any one compound as described in the present invention, including its isomer, prodrug, solvate, pharmaceutically acceptable salt or other chemically protected forms, and one or more pharmaceutically acceptable carrier.

"Pharmaceutically acceptable carriers" as used in the present invention refers to a carrier which does not cause a significant irritation to the organism or does not interfere with the biological activity and properties of the administered compound, comprising solvent, diluent or other excipient, dispersant, surfactant, isotonic agent, thickening agent or emulsifying agent, preservative, solid binder, lubricant and the like, unless any conventional carrier medium is incompatible with the compound of the present invention. Some examples which can be used as a pharmaceutically acceptable carrier include, but not limited to, sugar, such as lactose, glucose and sucrose; starch, such as corn starch and potato starch; cellulose and derivative thereof, such as sodium carboxymethyl cellulose, as well as cellulose and cellulose acetate; malt, gelatin and the like.

"Excipient" as used in the present invention refers to an inert substance added to the pharmaceutical composition to further facilitate the administration of the compound. Excipient may include calcium carbonate, calcium phosphate, various sugars and various types of starch, cellulose derivative, gelatin, vegetable oil and polyethylene glycol.

DETAILED EMBODIMENTS

The following representative examples are included in order to better illustrate the present invention and are not intended to limit the scope of the present invention.

Example 1

Dimethyl (2S,2'S)-1,1'-((2S,2'S)-2,2'-(5,5'-(9,9,10,10-tetrafluoro-9,10-dihydrophenanthren-2,7-diyl)bis(1H-imidazol-5,2-diyl))bis(pyrrolidin-2,1-diyl))bis(3-methyl-1-oxobutan-2,1-diyl)dicarbamate

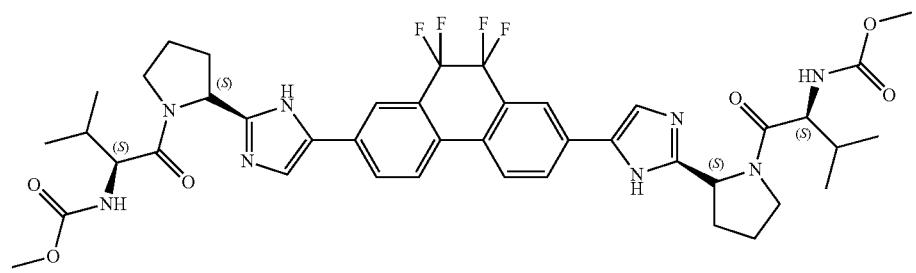

Step 1 Preparation of (S)-1-tert-butoxycarbonyl-2-formylpyrrolidine

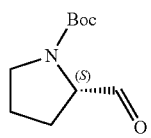

In a 250 mL eggplant-shaped flask, 16 mL oxalyl chloride and 125 mL anhydrous dichloromethane were added, and under nitrogen gas protection at −78° C., 10 mL dichloromethane solution dissolved with 23 mL DMSO and 10 mL dichloromethane solution dissolved with 10 g (s)-1-tert-butoxycarbonyl-2-hydroxymethyl-pyrrolidine were slowly added thereto. After the addition, the mixture was further stirred at −78° C. for 30 min, and then 46 mL triethylamine (TEA) was added dropwise slowly thereto. After the addition, the mixture was stirred at 0-4° C. for 30 min. After completion of the reaction, the reaction liquid was slowly poured into 100 g of ice cubes, and 200 mL saturated aqueous sodium chloride solution was added thereto, and then the mixture was extracted with dichloromethane (3×200 mL). The organic phase was collected, dried over anhydrous sodium sulfate, and concentrated to give the title compound, which was used directly in the next step of reaction.

LC-MS m/z: $[M+H]^+$=200.

Step 2 Preparation of (S)-1-tert-butoxycarbonyl-2-(1H-imidazol-2-yl)pyrrolidine

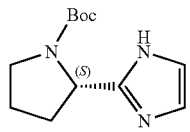

12 g compound (S)-1-tert-butoxycarbonyl-2-formylpyrrolidine prepared in step 1 was weighed into a 100 mL reaction flask, and dissolved by adding 30 mL anhydrous methanol and 30 mL aqueous ammonia solution, and at 0-4° C., 14 mL glyoxal was slowly added dropwise thereto. The reaction was performed at room temperature for 16 h. After completion of the reaction, the reaction liquid was concentrated to remove the majority of the ethanol, and extracted by adding dichloromethane (3×50 mL). The combined organic layer was dried over anhydrous sodium sulfate, filtered, and concentrated to give a crude product. The crude product was recrystallized in 100 mL mixed solution of petroleum ether/ethyl acetate in 1:1 volume ratio to give the title compound.

LC-MS m/z: $[M+H]^+$=238.

Step 3 Preparation of (S)-1-tert-butoxycarbonyl-2-(4,5-dibromo-1H-imidazol-2-yl)pyrrolidine

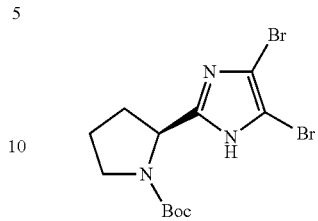

2.4 g compound (S)-1-tert-butoxycarbonyl-2-(1H-imidazol-2-yl)pyrrolidine prepared in step 2 was weighed into a 100 mL reaction flask, and 3.6 g N-bromosuccinimide (NBS) and 30 mL THF were added thereto. The reaction was performed under nitrogen gas protection at room temperature for 3 h. After completion of the reaction, 20 mL water was added, and the mixture was extracted with ethyl acetate (3×60 mL). The combined organic phase was dried, filtered, concentrated and purified by column chromatography to give the title compound.

ESI-MS m/z: $[M+H]^+$=394.0, calcd: 393.9.

Step 4 Preparation of (S)-1-tert-butoxycarbonyl-2-(4-bromo-1H-imidazol-2-yl)pyrrolidine

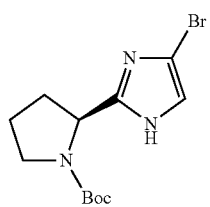 [SMILES: CC(C)(C)OC(=O)N1CCC[C@H]1c1nc(Br)c[nH]1]

9.58 g compound (S)-1-tert-butoxycarbonyl-2-(4,5-dibromo-1H-imidazol-2-yl)pyrrolidine prepared in step 3 and 3.0 g sodium sulfite was weighed into a 100 mL reaction flask, and 50 mL ethanol/water mixed solution in volume ratio of 1:1 was added thereto. The reaction was performed at 90° C. for 24 h. The mixture was filtered, concentrated and purified by column chromatography to give the title compound.

ESI-MS m/z: $[M+H]^+$=316.1, 318.1, calcd: 316.1, 318.1.

Step 5 Preparation of (S)-2-(4-bromo-1H-imidazol-2-yl)pyrrolidine

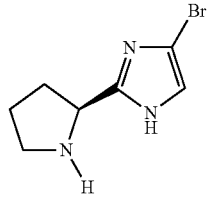 [SMILES: Brc1c[nH]c([C@@H]2CCCN2)n1]

1 g compound (S)-1-tert-butoxycarbonyl-2-(4-bromo-1H-imidazol-2-yl) pyrrolidine prepared in step 4 was weighted into a 50 mL reaction flask, and 2 mL trifluoroacetic acid (TFA) and 8 mL methylene chloride were added thereto. The reaction was performed at room temperature for 3 h. After completion of the reaction, the mixture was concentrated, diluted by adding 30 mL dichloromethane, washed with saturated sodium bicarbonate solution (1×20 mL) and saturated brine (1×20 mL), dried over anhydrous sodium, filtered, and concentrated to give the title compound.

Step 6 Methyl (S)-1-((S)-2-(4-bromo-1H-imidazol-2-yl)pyrrolidin-1-yl)-3-methyl-1-oxobutan-2-yl)carbamate

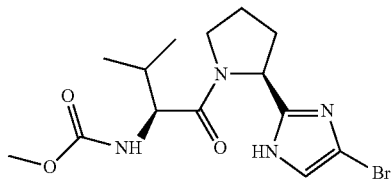 [SMILES: COC(=O)N[C@H](C(=O)N1CCC[C@H]1c1nc(Br)c[nH]1)C(C)C]

1.2 g compound (S)-2-(4-bromo-1H-imidazol-2-yl)pyrrolidine prepared in step 5, 665 mg (S)-2-(methoxycarbonylamino)-3-methylbutyric acid, 1.44 g 2-(7-azabenzotriazol-1-yl)-N,N,N',N'-tetramethyluronium hexafluorophosphate (HATU) and 1.23 g DIPEA were weighed into a 50 mL reaction flask, and 10 mL DMF was added thereto. The reaction was performed at room temperature for 24 h. After completion of the reaction, 20 mL water was added. The mixture was extracted with ethyl acetate (3×60 mL), and the combined organic phase was dried, filtered, concentrated, and purified by column chromatography to give the title compound.

¹H NMR (300 MHz, d₆-DMSO) δ ppm: 12.0-13.2 (brs, 1H), 7.39 (s, 1H), 7.19 (s, 1H), 4.91-4.93 (m, 1H), 4.51-4.55 (m, 1H), 3.61-3.65 (m, 1H), 3.49-3.52 (m, 1H), 3.47 (s, 3H), 2.66-2.72 (m, 1H), 2.02-2.12 (m, 2H), 1.96-2.02 (m, 2H), 0.79-0.87 (m, 6H).

ESI-MS m/z: [M−56+H]⁺=317.2, [M+H]⁺ calcd: 373.1.

Step 7 Preparation of 2,7-dibromo-9,9,10,10-tetrafluoro-9,10-dihydro phenanthrene

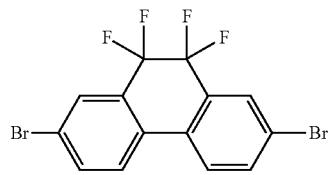 [SMILES: FC1(F)c2cc(Br)ccc2-c2ccc(Br)cc2C1(F)F]

10 g 2,7-dibromophenanthraquinone and 5.0 g bis(2-methoxyethyl)amino sulfur trifluoride (BAST) were weighed into a 50 mL tetrafluoride-pot and reacted at 80° C. for 48 h. After completion of the reaction, the reaction was quenched by adding 30 mL ice water, and the reaction mixture was extracted with ethyl acetate (4×60 mL). The combined organic phase was washed with saturated brine (3×60 mL), dried, filtered, concentrated, and purified by column chromatography to give the title compound.

¹HNMR (300 MHz, CDCl₃) δ ppm: 7.93 (s, 2H), 7.65-7.75 (m, 4H).

Step 8 Preparation of 2,2'-(9,9,10,10-tetrafluoro-9,10-dihydrophenanthren-2,7-diyl)bis(4,4,5,5-tetramethyl-1,3,2-dioxaborolane)

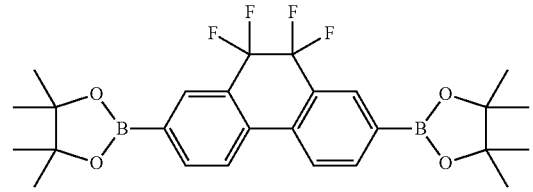

0.8 g compound 2,7-dibromo-9,9,10,10-tetrafluoro-9,10-dihydrophenanthrene prepared in step 7, 1.98 g bis(pinacolato)diboron, 1.2 g potassium acetate and 70.2 mg 1,1'-bis(diphenylphosphino)ferrocene-palladium dichloride (Pd(dppf)Cl₂) were weighted into a 100 mL reaction flask, and 5 mL 1,4-dioxane were added thereto. The reaction was performed under nitrogen gas protection at 100° C. for 24 h. After completion of the reaction, 100 mL water was added and the mixture was extracted with ethyl acetate (3×60 mL). The combined organic phase was washed with saturated brine (3×60 mL), dried, filtered, concentrated, and purified by column chromatography to give the title compound.

¹HNMR: (300 MHz, CDCl₃) δ ppm: 8.24 (s, 2H), 8.02 (d, 2H), 7.87 (d, 2H), 1.37 (s, 24H).

Step 9 Dimethyl (2S,2'S)-1,1'-((2S,2'S)-2,2'-(5,5'-(9,9,10,10-tetrafluoro-9,10-dihydrophenanthren-2,7-diyl)bis(1H-imidazol-5,2-diyl))bis(pyrrolidin-2,1-diyl))bis(3-methyl-1-oxobutan-2,1-diyl)dicarbamate

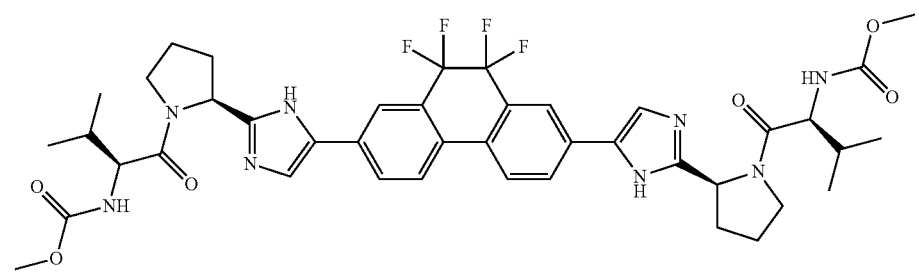

155 mg compound methyl (S)-1-((S)-2-(4-bromo-1H-imidazol-2-yl)pyrrolidin-1-yl)-3-methyl-1-oxobutan-2-yl) carbamate prepared in step 6, 80 mg compound 2,2'-(9,9,10,10-tetrafluoro-9,10-dihydrophenanthren-2,7-diyl)bis(4,4,5,5-tetramethyl-1,3,2-dioxaborolane) prepared in step 8, 406 mg cesium carbonate and 29.13 mg Pd(PPh₃)₂Cl₂ were weighted into a 100 mL reaction flask, and 6 mL DMF/H₂O mixed solution in a volume ratio of 2:1 was added thereto. The reaction was performed under nitrogen gas protection at 100° C. for 24 h. After completion of the reaction, 20 mL water was added and the mixture was extracted with ethyl acetate (3×60 mL). The combined organic phase was dried, filtered, concentrated and purified by column chromatography to give the title compound.

¹HNMR: (300 MHz, MeOD) δ ppm: 8.24-8.30 (m, 4H), 8.06-8.09 (m, 2H), 7.92-7.97 (m, 2H), 5.23-5.28 (m, 2H), 4.23-4.26 (m, 2H), 4.06-4.11 (m, 2H), 3.72-3.86 (m, 2H), 3.68-3.78 (m, 6H), 2.52-2.56 (m, 2H), 2.23-2.27 (m, 8H), 0.86-0.95 (m, 12H).

ESI-MS m/z: [M+H]⁺=837.2, calcd: 837.2.

Example 2

Preparation of dimethyl (2S,2'S)-1,1'-((2S,2'S)-2,2'-(5,5'-(4,4'-(9,9,10,10-tetrafluoro-9,10-dihydro-phenanthren-2,7-diyl)bis(4,1-phenylene))bis(1H-imidazol-5,2-diyl))bis(pyrrolidin-2,1-diyl))bis(3,3-dimethyl-1-oxobutan-2,1-diyl)dicarbamate

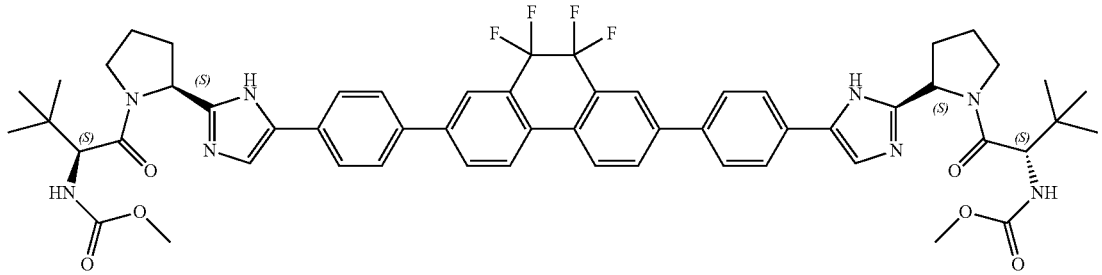

Step 2 Preparation of (S)-1-tert-butoxycarbonyl-2-(5-(4-bromophenyl)-1H-imidazol-2-yl)pyrrolidine

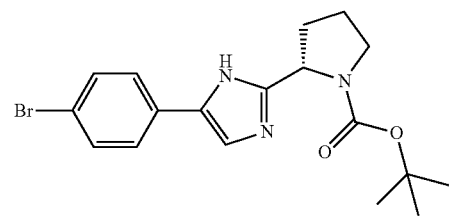

4 g compound (S)-1-tert-butoxycarbonyl-2-(2-(4-bromophenyl)-2-oxoethoxycarbonyOpyrrolidine prepared in step 1 and 7.5 g ammonium acetate were weighted into a 250 mL reaction flask, and 50 mL xylene was added thereto. The reaction was performed at 120° C. for 4 h. After completion of the reaction, the reaction mixture was spin-dried and then dissolved by adding 60 mL ethyl acetate, washed with saturated aqueous sodium bicarbonate (2×60 mL) and saturated brine (1×60 mL). The organic phase was dried over anhydrous sodium sulfate, filtered, concentrated and purified by column chromatography to give the title compound.

¹HNMR (300 MHz, d₆-DMSO) δ ppm: 11.92 (brs, 1H), 7.66-7.69 (m, 2H), 7.48-7.51 (m, 3H), 4.75-4.81 (m, 1H), 3.39-3.52 (m, 1H), 3.31-3.37 (m, 1H), 1.85-2.02 (m, 4H), 1.23-1.39 (m, 9H).

ESI-MS m/z: [M+H]⁺=392.0, calcd: 392.0.

Step 1 Preparation of (S)-1-tert-butoxycarbonyl-2-(2-(4-bromophenyl)-2-oxoethoxycarbonyl)pyrrolidine Step 3 Preparation of (S)-1-tert-butoxycarbonyl-2-(5-(4-(4,4,5,5-tetramethyl-1,3,2-dioxaborolan-2-yl)phenyl)-1H-imidazol-2-yl)pyrrolidine

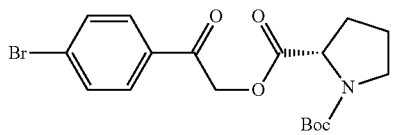 [SMILES: CC(C)(C)OC(=O)N1CCC[C@H]1C(=O)OCC(=O)c1ccc(Br)cc1]

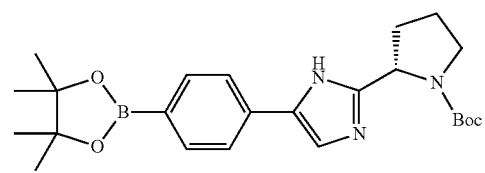 [SMILES: CC(C)(C)OC(=O)N1CCC[C@H]1c1ncc(-c2ccc(B3OC(C)(C)C(C)(C)O3)cc2)[nH]1]

5 g 2-bromo-1-(4-bromophenyl)ethylketone was weighted into a 250 mL reaction flask and 30 mL acetonitrile was added thereto, and at 0° C., 4 g (S)-1-tert-butoxycarbonylproline was added, and then after 5.45 g triethylamine was added in portions, the mixture was stirred at 25° C. for 2 h. After completion of the reaction, the mixture was concentrated to give the title compound, which was used directly in the next step.

The title compound was prepared by using compound (S)-1-tert-butoxy carb onyl-2-(5-(4-bromophenyl)-1H-imidazol-2-yl)pyrrolidine prepared in step 2 and bis(pinacolato)diboron as the starting materials according to the method in step 8 of Example 1.

¹HNMR (300 MHz, CD₃Cl) δ ppm: 7.79-7.81 (m, 2H), 7.62-7.69 (m, 2H), 7.26-7.27 (m, 1H), 4.97-4.99 (m, 1H), 3.39-3.43 (m, 2H), 2.97-3.02 (b, 1H), 2.09-2.16 (m, 2H), 1.96-2.00 (m, 2H), 1.26-1.49 (m, 21H).

ESI-MS m/z: [M+H]⁺=440.3, calcd: 440.2.

Step 4 Preparation of (S)-2-(5-(4-(4,4,5,5-tetramethyl-1,3,2-dioxaborolan-2-yl)phenyl)-1H-imidazol-2-yl)pyrrolidine

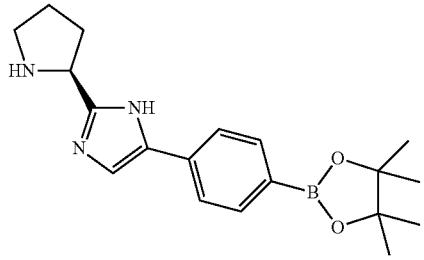 [SMILES: CC1(C)OB(c2ccc(-c3cnc([C@@H]4CCCN4)[nH]3)cc2)OC1(C)C]

The title compound was prepared by using compound (S)-1-tert-butoxy carbonyl-2-(5-(4-(4,4,5,5-tetramethyl-1,3,2-dioxaborolan-2-yl)phenyl)-1H-imidazol-2-yl)pyrrolidine prepared in step 3 as the starting material according to the method in step 5 of Example 1.

Step 5 Preparation of (S)-2-(methoxycarbonylamino)-3,3-dimethyl butyric acid

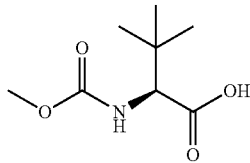

2 g (S)-2-amino-3,3-dimethyl butyric acid was weighted into a 100 mL eggplant-shaped flask, 15.27 mL aqueous NaOH solution (1 M) and 809 mg sodium carbonate were added thereto, and at 0-4° C., 1.3 mL methyl chloroformate was added dropwise slowly. After the addition, the reaction was continued at 0-4° C. for 20 min, then at room temperature for 4 h, and then cooled to 0° C. After diluting the reaction mixture by adding 20 mL diethyl ether, 3 mL concentrated hydrochloric acid was slowly added dropwise. The mixture was extracted with ethyl acetate (2×50 mL). The combined organic phase was washed with saturated brine (1×50 mL), dried over anhydrous sodium sulfate, filtered, concentrated and purified by column chromatography to give the title compound.

LC-MS m/z: [M+H]=190.

Step 6 Preparation of methyl (S-3,3-dimethyl-1-oxo-1-((S)-2-(5-(4-(4,4,5,5-tetramethyl-1,3,2-dioxaborolan-2-yl)phenyl)-1H-imidazol-2-yl)pyrrolidin-1-yl)butan-2-yl)carbamate

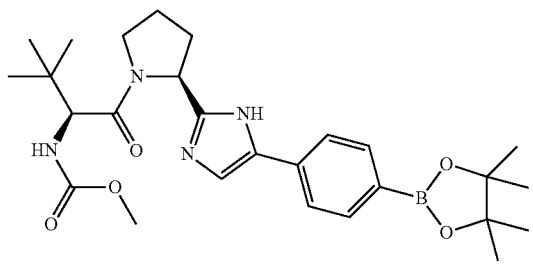 [SMILES: COC(=O)N[C@H](C(=O)N1CCC[C@H]1c1ncc(-c2ccc(B3OC(C)(C)C(C)(C)O3)cc2)[nH]1)C(C)(C)C]

0.5 g compound (S)-2-(5-(4-(4,4,5,5-tetramethyl-1,3,2-dioxaborolan-2-yl)phenyl)-1H-imidazol-2-yl)pyrrolidine prepared in step 4 was weighted into a 100 mL reaction flask, and after dissolved by adding 5 mL dichloromethane, 284 mg compound (S)-2-(methoxycarbonylamino)-3,3-dimethylbutyric acid prepared in step 5, 621 mg HATU and 421 mg DIPEA were added thereto. The reaction was performed at 20° C. for 2 h. After completion of the reaction, 20 mL water was added and the mixture was extracted with dichloromethane (3×60 mL). The combined organic phase was dried, filtered, concentrated and purified by column chromatography to give the title compound.

Step 7 Preparation of dimethyl (2S,2'S)-1,1'-((2S,2'S)-2,2'-(5,5'-(9,9,10,10-tetrafluoro-9,10-dihydrophenanthren-2,7-diyl)bis(4,1-phenylene)bis(1H-imidazol-5,2-diyl))bis(pyrrolidin-2,1-diyl))bis(3,3-dimethyl-1-oxobutan-2,1-diyl)dicarbamate

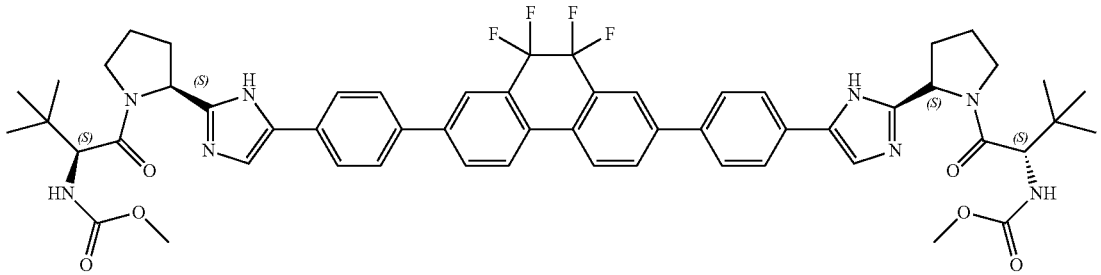

The title compound was prepared by using compound methyl (S-3,3-dimethyl-1-oxo-1-((S)-2-(5-(4-(4,4,5,5-tetramethyl-1,3,2-dioxaborolan-2-yl)phenyl)-1H-imidazol-2-yl)pyrrolidin-1-yl)butan-2-yl)carbamate prepared in step 6 and the compound 2,7-bromo-9,9,10,10-tetrafluoro-9,10-dihydrophenanthrene prepared in step 7 of Example 1 as the starting materials according to the method in step 9 of Example 1.

$^1$HNMR: (300 MHz, MeOD) δ ppm: 7.56-8.20 (m, 12H), 7.30-7.428 (m, 4H), 5.20-5.25 (m, 2H), 4.32-4.36 (m, 2H), 3.92-4.02 (m, 4H), 3.66-3.68 (m, 6H), 2.20-2.28 (m, 4H), 2.00-2.11 (m, 4H), 0.86-0.95 (m, 18H).

ESI-MS m/z: [M/2+H]$^+$=509.2, [M+H]$^+$=1017.6, calcd: 1017.4.

Example 3

Dimethyl (2S,2'S)-1,1'-((1R,1'R,3S,3'S,4S,4'S)-3,3'-(5,5'-(9,9,10,10-tetrafluoro-9,10-dihydrophenanthren-2,7-diyl)bis(1H-imidazol-5,2-diyl))bis(2-azabicyclo[2.2.1]heptan-3,2-yl))bis(3-methyl-1-oxobutan-2,1-diyl)dicarbamate

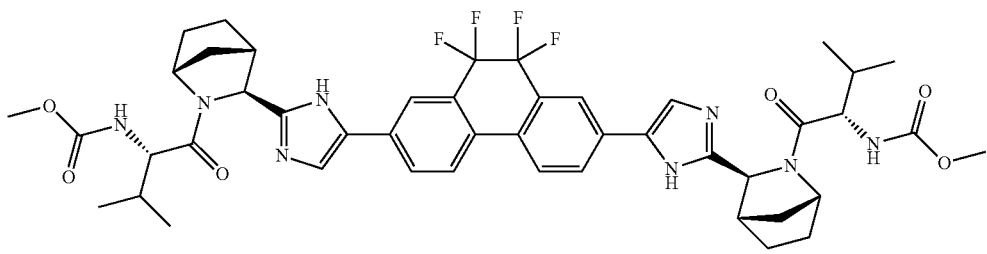

Step 1 2,7-bis(1-ethoxyethen-1-yl)-9,9,10,10-tetrafluoro-9,10-dihydro phenanthrene

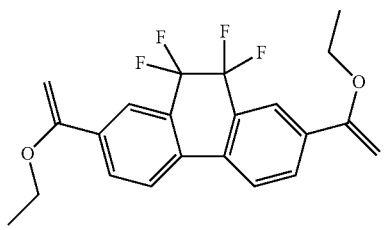 [SMILES: C=C(OCC)c1ccc2c(c1)C(F)(F)C(F)(F)c1cc(C(=C)OCC)ccc1-2]

1 g compound 2,7-dibromo-9,9,10,10-tetrafluoro-9,10-dihydrophenanthrene prepared in step 7 of Example 1 was weighted into a 50 mL three-necked reaction flask, and 15 mL toluene, 1.95 g tributyl(1-ethoxyethenyl)stannane and 0.1 g (PPh$_3$)$_2$PdCl$_2$ were added thereto. After displaced with Ar gas for 3 times, the mixture was stirred at 90° C. for 8 h. The reaction liquid was cooled to room temperature, and 5 mL aqueous solution dissolved with 5 g potassium fluoride was added. The mixture was stirred for 3 h, and then extracted by adding ethyl acetate, washed with aqueous sodium bicarbonate solution and brine, dried over anhydrous sodium sulfate, filtered and concentrated to give the title compound.

Step 2 2,7-diacetyl-9,9,10,10-tetrafluoro-9,10-dihydrophenanthrene

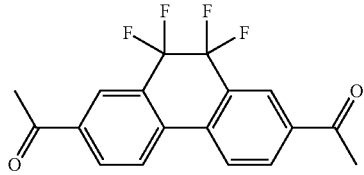 [SMILES: CC(=O)c1ccc2c(c1)C(F)(F)C(F)(F)c1cc(C(C)=O)ccc1-2]

The crude compound 2,7-bis(1-ethoxy ethen-1-yl)-9,9,10,10-tetrafluoro-9,10-dihydrophenanthrene prepared in step 1 was added into a reaction flask and dissolved by adding 20 mL THF, and then 10 mL 2 N hydrochloric acid was added. The mixture was stirred at room temperature for 5 h. After completion of the reaction, the mixture was extracted with ethyl acetate (1×30 mL), washed with sodium bicarbonate solution (2×30 mL), washed with saturated brine (2×50 mL), dried over anhydrous sodium sulfate, filtered, concentrated and purified by column chromatography to give the title compound.

$^1$HNMR (300 MHz, DMSO-d6): 8.46 (2H, d), 8.35 ((4H, d), 2.71 (6H, s).

MS(ESI): [M+1]$^+$=337.1.

Step 3 1,1'-(9,9,10,10-tetrafluoro-9,10-dihydrophenanthren-2,7-diyl)bis(2-bromoethanone)

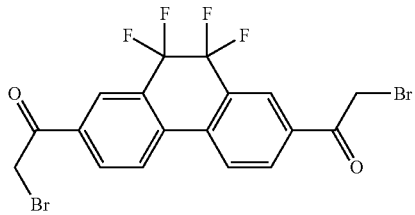 [SMILES: O=C(CBr)c1ccc2c(c1)C(F)(F)C(F)(F)c1cc(C(=O)CBr)ccc1-2]

412 mg compound 2,7-di acetyl-9,9,10,10-tetrafluoro-9,10-dihydrophenanthrene prepared in step 2 was weighted into a 25 mL reaction flask and dissolved by adding 8 mL CHCl$_3$, and then 392 mg bromine was added. The reaction was performed at room temperature for 2 h. After completion of the reaction, the mixture was concentrated to give the title compound.

MS (ESI): [M+1]$^+$=495.0.

Step 4 (1R,1'R,3S,3'S,4S,4'S)-3,3'-(9,9,10,10-tetrafluoro-9,10-dihydro phenanthren-2,7-diyl)bis((2-oxoethoxy)carbonyl)bis(2-tert-butoxycarbonyl-2-azabicyclo[2.2.1]heptane)

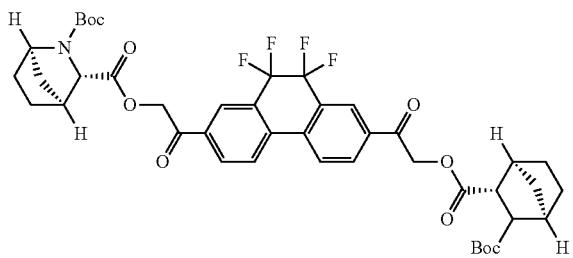 [SMILES: CC(C)(C)OC(=O)C1[C@@H]2CC[C@@H](C2)[C@H]1C(=O)OCC(=O)c1ccc2c(c1)C(F)(F)C(F)(F)c1cc(C(=O)COC(=O)[C@@H]3[C@H]4CC[C@H](C4)N3C(=O)OC(C)(C)C)ccc1-2]

580 mg compound 1,1'-(9,9,10,10-tetrafluoro-9,10-dihydrophenanthren-2,7-diyl)bis(2-bromoethanone) prepared in step 3 was added into a 25 mL reaction flask, and mL acetonitrile, 135 mg (1R,3S,4S)-2-(t-butoxy carbonyl)-2-azabicyclo[2.2.1]heptan-3-carboxylic acid and 137 uL of N,N-diisopropylethylamine (DIPEA) were added thereto. The reaction was performed at room temperature for 1 h. After completion of the reaction, the reaction liquid was concentrated to give the title compound.

MS (ESI): [M+Na]⁺=837.3.

Step 5 (1R,1'R,3S,3'S,4S,4'S)-3,3'-(5,5'-(9,9,10,10-tetrafluoro-9,10-dihydrophenanthren-2,7-diyl)bis(1H-imidazol-5,2-diyl))bis(tert-butyl 2-azabicyclo[2.2.1]heptan-2-formate)

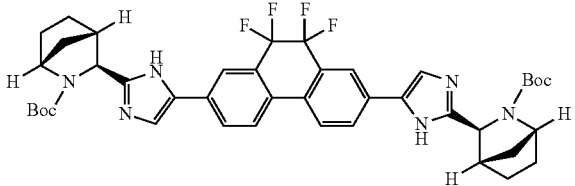 [SMILES: CC(C)(C)OC(=O)N1[C@@H]2CC[C@@H](C2)[C@H]1c1ncc(-c2ccc3c(c2)C(F)(F)C(F)(F)c2cc(-c4cnc([C@@H]5[C@H]6CC[C@H](C6)N5C(=O)OC(C)(C)C)[nH]4)ccc2-3)[nH]1]

The title compound was prepared by using compound (1R,1'R,3S,3'S,4S,4'S)-3,3'-(9,9,10,10-tetrafluoro-9,10-dihydrophenanthren-2,7-diyl)bis((2-oxoethoxy)carbonyl)bis(2-tert-butoxycarbonyl-2-azabicyclo[2.2.1]heptane) prepared in step 4 and ammonium acetate as the starting materials according to the method in step 2 of Example 2 to obtain the title compound.

Step 6 (1R,1'R,3S,3'S,4S,4'S)-3,3'-(5,5'-(9,9,10,10-tetrafluoro-9,10-dihydro phenanthren-2,7-diyl)bis(1H-imidazol-5,2-diyl))bis(2-azabicyclo[2.2.1]heptane)

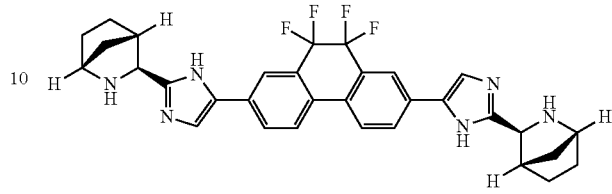

The title compound was prepared by using compound (1R,1'R,3S,3'S,4S,4'S)-3,3'-(5,5'-(9,9,10,10-tetrafluoro-9,10-dihydrophenanthren-2,7-diyl)bis(1H-imidazol-5,2-diyl))bis(tert-butyl 2-azabicyclo[2.2.1]heptan-2-formate) prepared in step 5 as the starting material according to the method in step 5 of Example 1.

MS (ESI): [M+1]⁺=575.2.

Step 7 Dimethyl (2S,2'S)-1,1'-(1R,1'R,3S,3'S,4S,4'S)-3,3'-(5,5'-(9,9,10,10-tetrafluoro-9,10-dihydrophenanthren-2,7-diyl)bis(1H-imidazol-5,2-diyl))bis(2-azabicyclo[2.2.1]heptan-3,2-yl))bis(3-methyl-1-oxobutan-2,1-diyl)dicarbamate

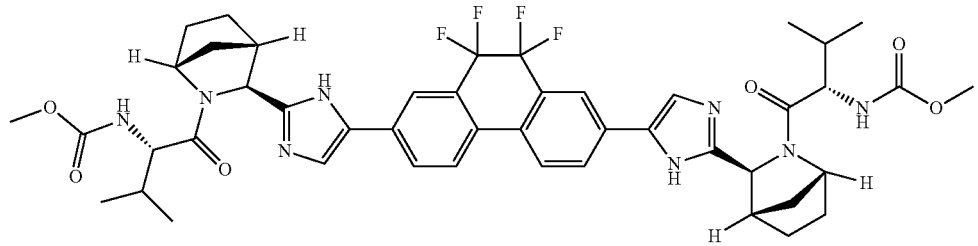

110 mg compound (1R,1'R,3S,3'S,4S,4'S)-3,3'-(5,5'-(9,9,10,10-tetrafluoro-9,10-dihydrophenanthren-2,7-diyl)bis(1H-imidazol-5,2-diyl))bis(2-azabicyclo[2.2.1]heptane) prepared in step 6 and 67 mg MOC-valine (N-methoxycarbonyl-L-valine) were weighted into a 50 mL reaction flask, and 137 uL DIPEA, 145 mg HATU, 47 mg DMAP and 3 mL of DMF were added thereto. The reaction was performed at 50° C. for 12 h. After completion of the reaction, 20 mL water was added, and the mixture was extracted with ethyl acetate (2×20 mL), washed with saturated brine, dried over anhydrous sodium sulfate, filtered, concentrated and purified by column chromatography to give the title compound.

¹HNMR (300 MHz, DMSO-d6): 9.96 (2H, s), 8.10-8.23 (4H, m), 7.98-8.10 (4H, m), 7.44 (1H, m), 7.25-7.32 (1H, m), 4.61 (2H, s), 4.52 (2H, s), 4.19-4.20 (2H, m), 3.56 (6H, s), 2.67-2.69 (2H, m), 2.06-2.26 (4H, m), 1.80-1.84 (6H, m), 1.50-1.54 (4H, m), 0.98-1.00 (6H, m), 0.87-0.89 (6H, m).

MS(ESI): [M+1]⁺=889.5.

Example 4

Dimethyl (2S,2'S)-1,1'-((1R,1'R,3S,3'S,4S,4'S)-3,3'-(5,5'-(9,9,10,10-tetrafluoro-9,10-dihydrophenanthren-2,7-diyl)bis(1H-imidazol-5,2-diyl))bis(2-azabicyclo[2.2.1]heptan-3,2-yl))bis(3,3-dimethyl-1-oxobutan-2,1-diyl)dicarbamate

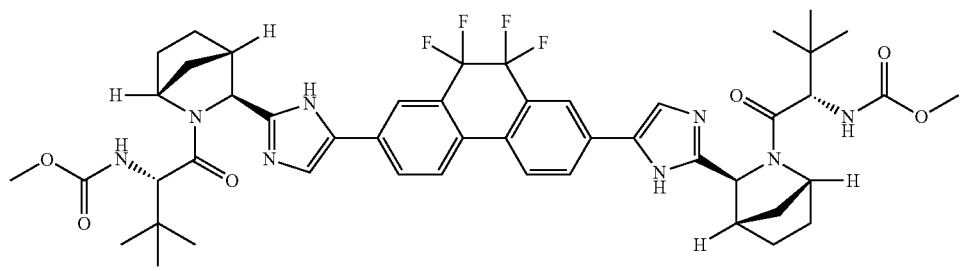

The title compound was prepared by using compound (1R,1'R,3S,3'S,4S,4'S)-3,3'-(5,5'-(9,9,10,10-tetrafluoro-9,10-dihydrophenanthren-2,7-diyl)bis(1H-imidazol-5,2-diyl))bis(2-azabicyclo[2.2.1]heptane) prepared in step 6 of Example 3 and compound (S)-2-(methoxycarbonylamino)-3,3-dimethyl butyric acid prepared in step 5 of Example 2 as the starting materials according to the method in step 7 of Example 3.

$^1$HNMR (300 MHz, DMSO-d6): 10.00 (2H, s) 8.21-8.24 (4H, m), 8.05-8.08 (2H, m), 7.96-8.05 (2H, m), 7.12-7.29 (2H, m), 4.59-4.63 (4H, m), 4.27-4.30 (2H, m), 3.19 (1H, s), 3.57 (6H, s) 2.64 (1H, s), 2.18-2.21 (2H, m), 1.71-1.79 (6H, m), 1.44-1.51 (4H, m), 0.92-1.01 (18H, m).

MS(ESI): $[M/2+1]^+$=459.4.

Example 5

Dimethyl (2S,2'S,3R,3'R)-1,1'-((1R,1'R,3S,3'S,4S,4'S)-3,3'-(5,5'-(9,9,10,10-tetrafluoro-9,10-dihydrophenanthren-2,7-diyl)bis(1H-imidazol-5,2-diyl))bis(2-aza bicyclo[2.2.1]heptan-3,2-diyl))bis(3-hydroxy-1-oxobutan-2,1-diyl)dicarbamate

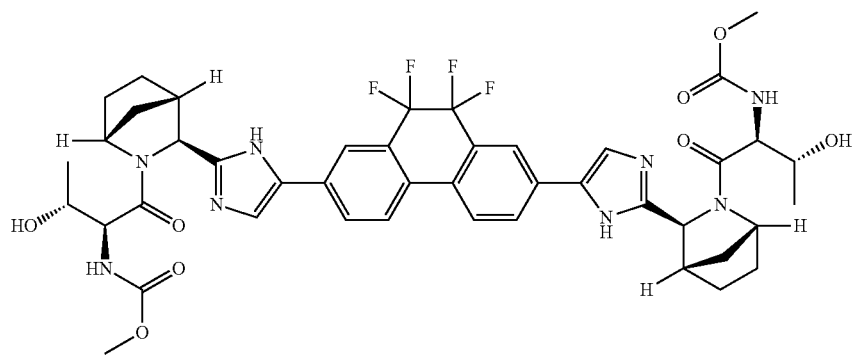 [SMILES: COC(=O)N[C@H](C(=O)N1[C@@H]2CC[C@@H](C2)[C@H]1c1ncc(-c2ccc3c(c2)C(F)(F)C(F)(F)c2cc(-c4cnc([C@@H]5[C@H]6CC[C@H](C6)N5C(=O)[C@@H](NC(=O)OC)[C@@H](C)O)[nH]4)ccc2-3)[nH]1)[C@@H](C)O]

Step 1
(2S,3R)-3-hydroxy-2-(methoxycarbonylamino)butanoic acid

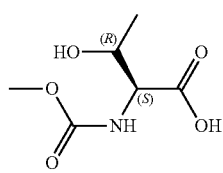

The title compound was prepared by using L-threonine and methyl chloroformate as the starting materials according to the method in step 5 of Example 2.

¹HNMR (400 MHz, DMSO-d₆) δ ppm: 6.86-6.88 (d, 1H), 4.02-4.09 (m, 1H), 3.91-3.94 (m, 1H), 3.55 (s, 3H), 1.08-1.09 (d, 3H).

LC-MS m/z: [M+H]⁺=178.

Step 2 Dimethyl (2S,2'S,3R,3'R)-1,1'-((1R,1'R,3S,3'S,4S,4'S)-3,3'-(5,5'-(9,9,10,10-tetrafluoro-9,10-dihydrophenanthren-2,7-diyl)bis(1H-imidazol-5,2-diyl))bis(2-azabicyclo[2.2.1]heptane-3,2-diyl))bis(3-hydroxy-1-oxobutan-2,1-diyl)dicarbamate The title compound was prepared by using compound (1R,1'R,3S,3'S,4S,4'S)-3,3'-(5,5'-(9,9,10,10-tetrafluoro-9,10-dihydrophenanthren-2,7-diyl)bis(1H-imidazol-5,2-diyl))bis(2-azabicyclo[2.2.1]heptane) prepared in step 6 of Example 3 and compound (2S,3R)-3-hydroxy-2-((methoxycarbonyl)amino)butanoic acid prepared in step 1 as the starting materials according to the method in step 7 of Example 3.

¹HNMR (300 MHz, DMSO-d6): 9.95 (2H, s), 8.22-8.25 (4H, m), 7.95-8.10 (4H, m), 7.43-7.98 (2H, m), 7.28-7.41 (2H, m), 6.95-6.98 (2H, m), 4.60-4.64 (4H, m), 4.32-4.34 (2H, m), 3.95-3.99 (2H, m), 3.48 (6H, s), 2.47-2.50 (2H, m), 2.05-2.09 (2H, m), 1.75-1.81 (4H, m), 1.45-1.49 (4H, m), 1.16-1.23 (6H, m).

MS(ESI): [M+1]⁺=893.6.

Example 6

Dimethyl (2S,2'S,3R,3'R)-1,1'-((1R,1'R,3S,3'S,4S,4'S)-3,3'-(5,5'-(9,9,10,10-tetrafluoro-9,10-dihydrophenanthren-2,7-diyl)bis(1H-imidazol-5,2-diyl))bis(2-aza bicyclo[2.2.1]heptan-3,2-diyl))bis(3-methoxy-1-oxobutan-2,1-diyl)dicarbamate Step 1 (2S,3R)-3-methoxy-2-((methoxycarbonyl)amino)butyric acid

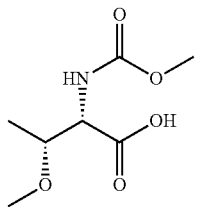

1 g O-methyl-L-threonine was weighted into a 50 mL single-necked flask and dissolved by adding 10 mL tetrahydrofuran, and then at 0° C., 10 mL aqueous solution dissolved with 0.33 g sodium hydroxide was added thereto. The mixture was stirred for 10 min, and then also at 0° C., 5 mL THF solution dissolved with 0.64 mL methyl chloroformate was added dropwise. The mixture was stirred at room temperature for 12 h. After completion of the reaction, the mixture was concentrated, diluted with 20 mL ethyl acetate, washed with saturated brine, dried over anhydrous sodium sulfate, filtered, and concentrated to give the title compound.

MS(ESI): [M+1]⁺=192.

Step 2 Dimethyl (2S,2'S,3R,3'R)-1,1'-((1R,1'R,3S,3'S,4S,4'S)-3,3'-(5,5'-(9,9,10,10-tetrafluoro-9,10-dihydrophenanthren-2,7-diyl)bis(1H-imidazol-5,2-diyl))bis(2-azabicyclo[2.2.1]heptan-3,2-diyl))bis(3-methoxy-1-oxobutan-2,1-diyl)dicarbamate The title compound was prepared by using compound (1R,1'R,3S,3'S,4S,4'S)-3,3'-(5,5'-(9,9,10,10-tetrafluoro-9,10-dihydrophenanthren-2,7-diyl)bis(1H-imidazol-5,2-diyl))bis(2-azabicyclo[2.2.1]heptane) prepared in step 6 of Example 3 and compound (2S,3R)-3-methoxy-2-((methoxycarbonyl)amino)butyric acid prepared in step 1 as the starting materials according to the method in step 7 of Example 3.

¹HNMR (300 MHz, DMSO-d6): 8.10-8.26 (4H, m), 8.01-8.07 (4H, m), 7.15-7.19 (2H, m), 4.54-4.61 (4H, m), 4.32-4.34 (2H, m), 3.56 (6H, s), 3.23 (6H, s), 2.49-2.52 (2H, m), 1.83-2.15 (2H, m), 1.72-1.78 (6H, m), 1.46-1.52 (4H, m), 1.08-1.16 (6H, m).

MS(ESI): [M+1]⁺=921.5.

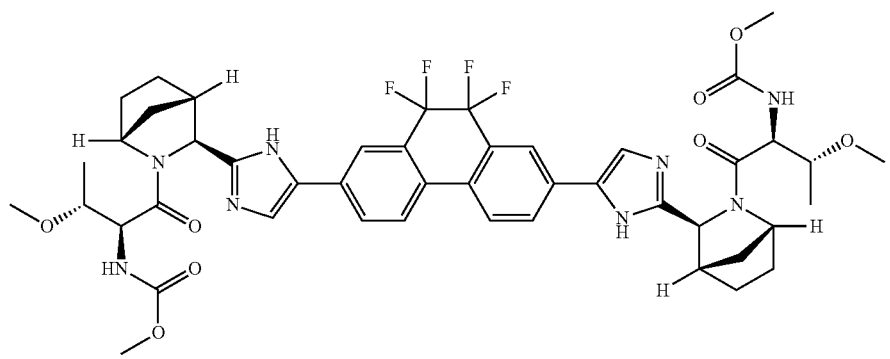

Example 7

Dimethyl (2S,2'S)-1,1'-((2S,2'S)-2,2'-(5,5'-(9,9,10,10-tetrafluoro-9,10-dihydrophenanthren-2,7-diyl)bis(1H-imidazol-5,2-diyl))bis(pyrrolidin-2,1-diyl))bis(3,3-dimethyl-1-oxobutan-2,1-diyl)dicarbamate

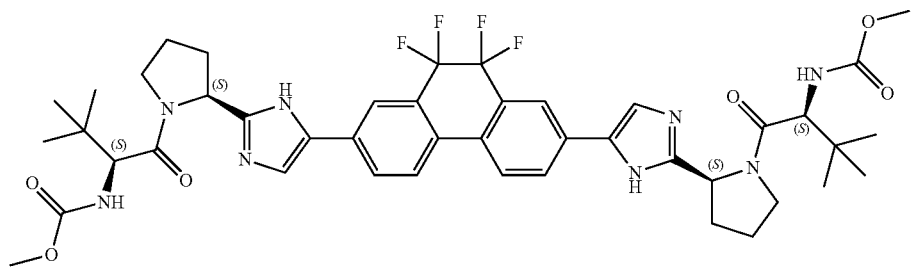

Step 1 (2S,2'S)-1,1'-di-tert-butoxycarbonyl-2,2'-((9,9,10,10-tetrafluoro-9,10-dihydrophenanthren-2,7-diyl)bis((2-oxoethoxy)carbonyl))dipyrrolidine

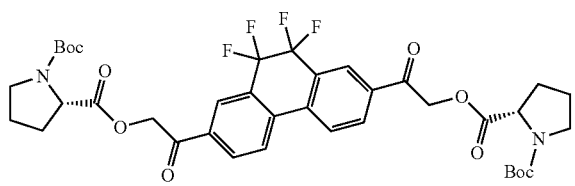 [SMILES: CC(C)(C)OC(=O)N1CCC[C@H]1C(=O)OCC(=O)c1ccc2c(c1)C(F)(F)C(F)(F)c1cc(C(=O)COC(=O)[C@@H]3CCCN3C(=O)OC(C)(C)C)ccc1-2]

The title compound was prepared by using compound 1,1'-(9,9,10,10-tetrafluoro-9,10-dihydrophenanthren-2,7-diyl)bis(2-bromo ethanone) prepared in step 3 of Example 3 and (S)-1-tert-butoxycarbonyl-2-carboxypyrrolidine as the starting materials according to the method in step 4 of Example 3.

Step 2 (2S,2'S)-1,1'-di-tert-butoxycarbonyl-2,2'-(5,5'-(9,9,10,10-tetrafluoro-9,10-dihydrophenanthren-2,7-diyl)bis(1H-imidazol-5,2-diyl))dipyrrolidine

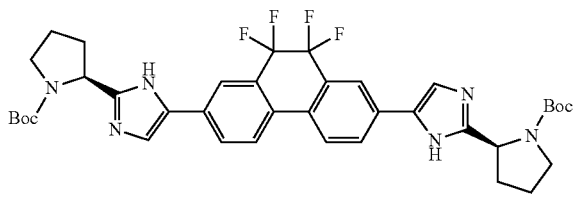 [SMILES: CC(C)(C)OC(=O)N1CCC[C@H]1c1ncc(-c2ccc3c(c2)C(F)(F)C(F)(F)c2cc(-c4cnc([C@@H]5CCCN5C(=O)OC(C)(C)C)[nH]4)ccc2-3)[nH]1]

The title compound was prepared by using compound (2S,2'S)-1,1'-di-tert-butoxy carbonyl-2,2'-((9,9,10,10-tetrafluoro-9,10-dihydrophenanthren-2,7-diyl)bis((2-oxoethoxy)carbonyl))dipyrrolidine prepared in step 1 as the starting material according to the method in step 2 of Example 2.

Step 3 (2S,2'S)-2,2'-(5,5'-(9,9,10,10-tetrafluoro-9,10-dihydrophenanthren-2,7-diyl)bis(1H-imidazol-5,2-diyl))dipyrrolidine

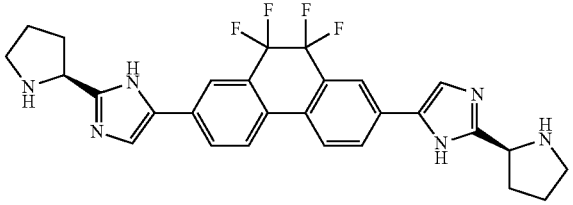 [SMILES: FC1(F)c2cc(-c3cnc([C@@H]4CCCN4)[nH]3)ccc2-c2ccc(-c3cnc([C@@H]4CCCN4)[nH]3)cc2C1(F)F]

The title compound was prepared by using compound (2S,2'S)-1,1'-di-tert-butoxy carbonyl-2,2'-(5,5'-(9,9,10,10-tetrafluoro-9,10-dihydrophenanthren-2,7-diyl)bis(1H-imidazol-5,2-diyl))dipyrrolidine prepared in step 2 as the starting material according to the method in step 5 of Example 1.

Step 4 Dimethyl (2S,2'S)-1,1'-((2S,2'S)-2,2'-(5,5'-(9,9,10,10-tetrafluoro-9,10-dihydrophenanthren-2,7-diyl(bis(1H-imidazol-5,2-diyl))bis(pyrrolidin-2,1-diyl))bis(3,3-dimethyl-1-oxobutan-2,1-diyl)dicarbamate

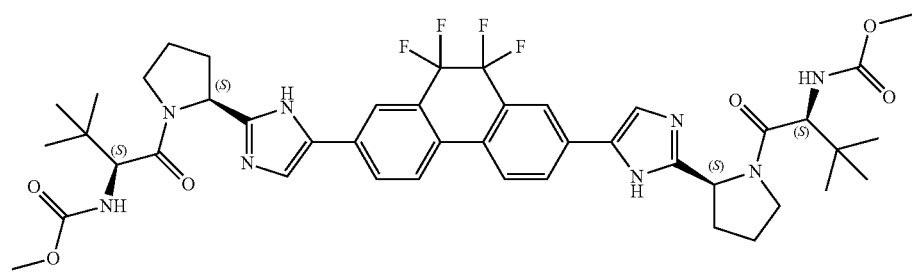

The title compound was prepared by using compound (2S,2'S)-2,2'-(5,5'-(9,9,10,10-tetrafluoro-9,10-dihydrophenanthren-2,7-diyl)bis(1H-imidazol-5,2-diyl))dipyrrolidine prepared in step 3 and compound (S)-2-(methoxycarbonylamino)-3,3-dimethyl butyric acid prepared in step 5 of Example 2 as the starting materials according to the method in step 7 of Example 3.

¹HNMR: (300 MHz, MeOD) δ ppm: 8.24-8.30 (m, 4H), 8.05-8.08 (m, 2H), 7.93-7.97 (m, 2H), 5.20-5.25 (m, 2H), 4.32 (s, 2H), 4.06-4.11 (m, 2H), 3.72-3.86 (m, 2H), 3.66 (s, 6H), 2.52-2.56 (m, 2H), 2.23-2.27 (m, 6H), 0.86-0.95 (m, 18H).

ESI-MS m/z: [M+H]⁺=865.3, 432.1, calcd: 865.4.

Example 8

Dimethyl ((2S,2'S,3R,3'R)-((2S,2'S)-2,2'-(5,5'-(9,9,10,10-tetrafluoro-9,10-dihydrophenanthren-2,7-diyl)bis(1H-imidazol-5,2-diyl))bis(pyrrolidin-2,1-diyl))bis(3-hydroxy-1-oxobutan-2,1-diyl))dicarbamate

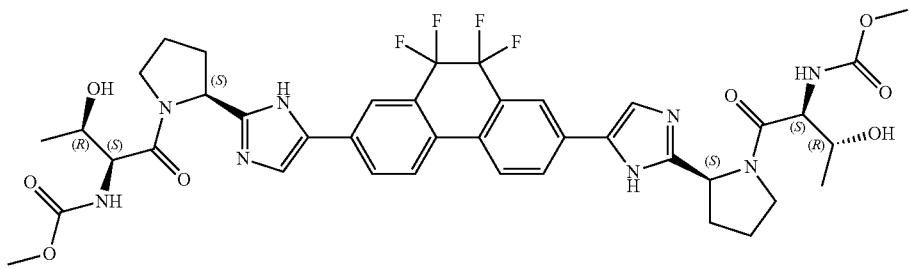

The title compound was prepared by using compound (2S,2'S)-2,2'-(5,5'-(9,9,10,10-tetrafluoro-9,10-dihydrophenanthren-2,7-diyl)bis(1H-imidazol-5,2-diyl))dipyrrolidine prepared in step 3 of Example 7 and compound (2S,3R)-3-hydroxy-2-((methoxycarbonyl)amino)butanoic acid prepared in step 1 of Example 5 as the starting materials according to the method in step 7 of Example 3.

¹HNMR: (500 MHz, MeOD) δ ppm: 8.24-8.30 (m, 4H), 8.06-8.09 (m, 2H), 7.92-9.97 (m, 2H), 5.23-5.28 (m, 2H), 4.51-4.56 (m, 2H), 4.11-4.16 (m, 2H), 3.94-4.02 (m, 4H), 3.68 (s, 6H), 2.52-2.56 (m, 2H), 2.23-2.27 (m, 6H), 1.15-1.20 (m, 6H).

ESI-MS m/z: [M+H]⁺=841.5, calcd: 841.3.

Example 9

Methyl N-((2S)-1-((2S)-2-(5-(7-(2-((S)-1-((S)-2-((methoxycarbonyl)amino)-3-methylbutanoyl)pyrrolidin-2-yl)-1H-imidazol-5-yl)-9,9,10,10-tetrafluoro-9,10-dihydrophenanthren-2-yl))-1H-benzo[d]imidazol-2-yl)pyrrolidin-1-yl)-3-methyl-1-oxobutan-2-yl)carbamate

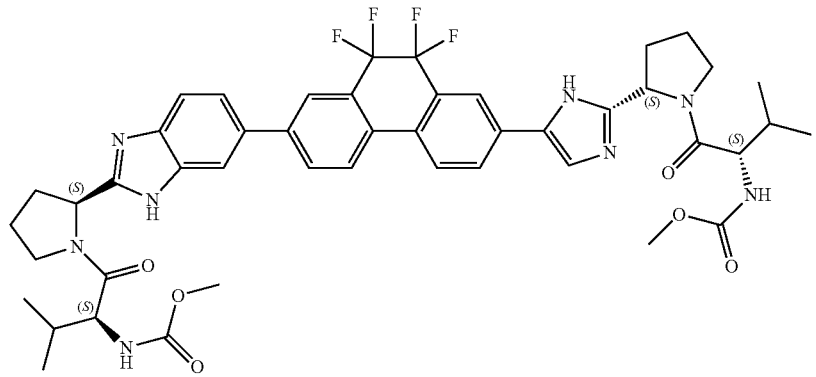

Step 1 2-acetyl-7-bromo-9,9,10,10-tetrafluoro-9,10-dihydrophenanthrene

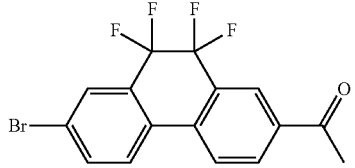 [SMILES: CC(=O)c1ccc2c(c1)C(F)(F)C(F)(F)c1cc(Br)ccc1-2]

2.07 g compound 2,7-dibromo-9,9,10,10-tetrafluoro-9,10-dihydrophenanthrene prepared in step 7 of Example 1 was weighted into a 50 mL three-necked flask, and 2.33 g Pd(PPh$_3$)$_4$, 1.65 g Pd(dppf)Cl$_2$, 1.7 mL tributyl(1-ethoxyethenyl)stannane and 30 mL 1,4-dioxane were added thereto. The reaction was performed under N2 protection at 80° C. for 8 h. After completion of the reaction, the reaction mixture was purified by column chromatography to give 2-(1-ethoxyethen-1-yl)-7-bromo-9,9,10,10-tetrafluoro-9,10-dihydrophenanthrene.

30 mL tetrahydrofuran was added into 2-(1-ethoxyethen-1-yl)-7-bromo-9,9,10,10-tetrafluoro-9,10-dihydrophenanthrene obtained by purification with column chromatography, then 3 N hydrochloric acid was added and stirred at room temperature for 6. After completion of the reaction, the reaction mixture was purified by column chromatography to give the title compound.

$^1$H NMR (300 MHz, DMSO-d6): 8.37 (1H, d), 8.32 (2H, d), 8.24 (1H, d), 8.13 (1H, s), 8.05 (1H, d), 2.69 (3H, s).

MS (ESI): [M+1]$^+$=373.0.

Step 2 2-bromo-1-(7-bromo-9,9,10,10-tetrafluoro-9,10-dihydrophenanthren-2-yl)ethanone

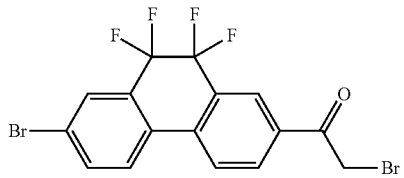 [SMILES: O=C(CBr)c1ccc2c(c1)C(F)(F)C(F)(F)c1cc(Br)ccc1-2]

0.74 g compound 2-acetyl-7-bromo-9,9,10,10-tetrafluoro-9,10-dihydrophenanthrene prepared in step 1 was weighted into a 50 mL three-necked flask, into which 20 mL anhydrous methylene chloride and 0.35 mL triethylamine were added, and under N2 protection at 0° C., 0.43 mL trimethylsilyl trifluoromethanesulfonate (TMSOTf) was added dropwise. The mixture was stirred at 0° C. for 30 min, and then warmed to room temperature. The reaction was performed at room temperature for 1 h. After completion of the reaction, 0.53 g NBS was added at room temperature, and the reaction was continued for 1 h. After completion of the reaction, the reaction liquid was concentrated to give the title compound, which was used directly in the next reaction step.

Step 3 (S)-1-tert-butoxycarbonyl-2-(((7-bromo-9,9,10,10-tetrafluoro-9,10-dihydrophenanthren-2-yl)-2-oxoethoxy)carbonyl)pyrrolidine

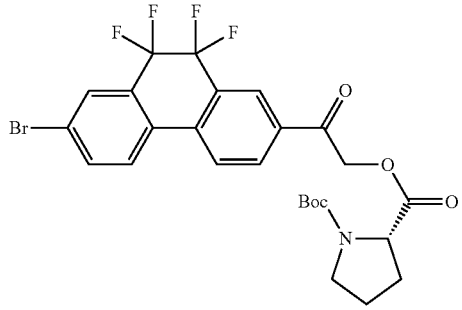 [SMILES: CC(C)(C)OC(=O)N1CCC[C@H]1C(=O)OCC(=O)c1ccc2c(c1)C(F)(F)C(F)(F)c1cc(Br)ccc1-2]

Compound 2-bromo-1-(7-bromo-9,9,10,10-tetrafluoro-9,10-dihydro phenanthren-2-yl)ethanone obtained in step 2 was added into a 50 mL eggplant-shaped flask, into which 20 mL acetonitrile, 0.65 mL DIEA and 425 mg N-Boc-L-proline were added. The reaction was performed at room temperature for 3 h. After completion of the reaction, the reaction liquid was concentrated to give the title compound, which was used directly in the next reaction step.

MS (ESI): [M−100+1]$^+$=486.1, [M+1]$^+$=586.1 (calcd).

Step 4 (S)-1-tert-butoxycarbonyl-2-(5-(7-bromo-9,9,10,10-tetrafluoro-9,10-dihydrophenanthren-2-yl)-1H-imidazol-2-yl)pyrrolidine

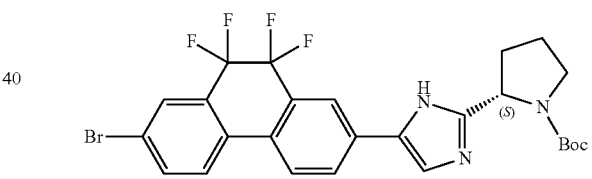

The title compound was prepared by using compound (S)-1-tert-butoxycarbonyl-2-(((7-bromo-9,9,10,10-tetrafluoro-9,10-dihydrophenanthren-2-yl)-2-oxoethoxy)carbonyl)pyrrolidine prepared in step 3 as the starting material according to the method in step 2 of Example 2.

MS (ESI): [M+1]$^+$=566.1.

Step 5 (S)-1-tert-butoxycarbonyl-2-(2-amino-4-bromophenylaminoacyl)pyrrolidine

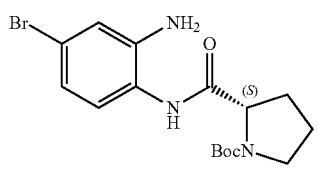

12.9 g Boc-L-proline was weighted into a 250 mL eggplant-shaped flask, and after dissolved by adding 150 mL DMF, 27.4 g 2-(7-azabenzotriazol-1-yl)-N,N,N',N'-tetramethyluronium hexafluorophosphate (HATU) and 11.6 g N,N-diisopropylethyl amine (DIPEA) were added thereto. The mixture was stirred at room temperature for 30 min, 11 g 4-bromo-o-phenylenediamine was slowly added thereto. After the addition, the reaction was performed at room temperature for 16 h. After the reaction was stopped, the reaction liquid was poured into 200 mL ice water and extracted with ethyl acetate (2×200 mL). The combined organic phase was washed with a saturated sodium chloride aqueous solution (2×200 mL), dried over anhydrous sodium sulfate, and concentrated to give the title compound, which was used directly in the next reaction step.

LC-MS m/z: [M+H]⁺=384.

Step 6 (S)-1-tert-butoxycarbonyl-2-(6-bromo-1H-benzo[d]imidazol-2-yl)pyrrolidine

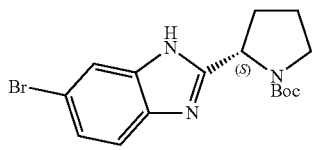

22 g compound (S)-1-tert-butoxycarbonyl-2-(2-amino-4-bromophenylamino acyl)pyrrolidine prepared in step 5 was weighted into a reaction flask and dissolved by adding 150 mL acetic acid. The reaction was performed at 85° C. for 2 h. After the reaction was stopped, the mixture was stirred at 0-4° C., and 40% aqueous sodium hydroxide solution was slowly added dropwise to adjust the pH to about 9. The mixture was extracted with ethyl acetate (2×200 mL). The combined organic phase was washed with saturated sodium chloride aqueous solution (2×200 mL), dried over anhydrous sodium sulfate, concentrated and purified by silica gel column chromatography to give the title compound.

LC-MS m/z: [M+H]⁺=366.

Step 7 (S)-1-tert-butoxycarbonyl-2-(6-(4,4,5,5-tetramethyl-1,3,2-dioxaborolan-2-yl)-1H-benzo[d]imidazol-2-yl)pyrrolidine

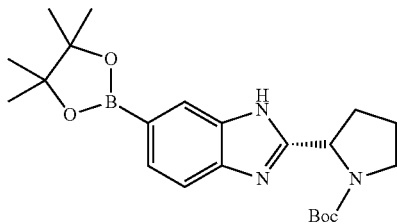

The title compound was prepared by using compound (S)-1-tert-butoxy carbonyl-2-(6-bromo-1H-benzo[d]imidazol-2-yl)pyrrolidine prepared in step 6 as the starting material according to the method in step 8 of Example 1.

LC-MS m/z: [M+H]⁺=414.

Step 8 (S)-1-tert-butoxycarbonyl-2-(5-(7-(2-((S)-1-(tert-butoxycarbonyl)pyrrolidin-2-yl)-1H-benzo[d]imidazol-6-yl)-9,9,10,10-tetrafluoro-9,10-dihydrophenanthren-2-yl)-1H-imidazol-2-yl)pyrrolidine

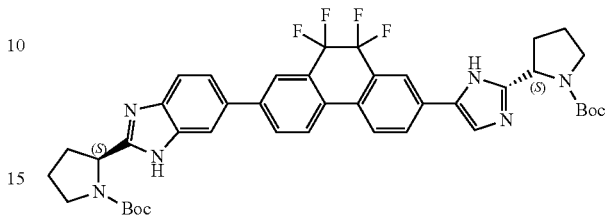

150 mg compound (S)-1-tert-butoxy carbonyl-2-(6-(4,4,5,5-tetramethyl-1,3,2-dioxaborolan-2-yl)-1H-benzo[d]imidazol-2-yl)pyrrolidine prepared in step 7, 109 mg compound (S)-1-tert-butoxy carbonyl-2-(5-(7-bromo-9,9,10,10-tetrafluoro-9,10-dihydrophenanthren-2-yl)-1H-imidazol-2-yl)pyrrolidine prepared in step 4, 31 mg tetrakistriphenylphosphine palladium (Pd(PPh₃)₄) and 110 mg potassium carbonate were weighted into a 50 mL three-necked flask, and 8 mL ethylene glycol dimethyl ether and 2 mL water were added thereto. The reaction was performed under nitrogen protection at 80° C. for 2 h. After completion of the reaction, the mixture was cooled to room temperature, and 10 mL water was added. The mixture was extracted with ethyl acetate (2×10 mL), washed with saturated brine (1×20 mL), dried over anhydrous sodium sulfate, filtered, and concentrated to give the title compound.

LC-MS m/z: [M+H]⁺=773.4.

Step 9 (S)-2-(5-(7-(2-((S)-pyrrolidin-2-yl)-1H-benzo[d]imidazol-6-yl)-9,9,10,10-tetrafluoro-9,10-dihydrophenanthren-2-yl)-1H-imidazol-2-yl)pyrrolidine

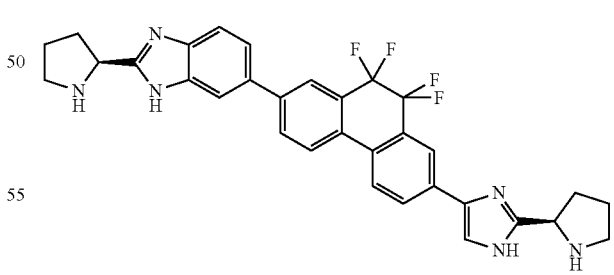

The title compound was prepared by using compound (S)-1-tert-butoxy carb onyl-2-(5-(7-(2-((S)-1-(tert-butoxycarbonyl)pyrrolidin-2-yl)-1H-benzo[d]imidazol-6-yl)-9,9,10,10-tetrafluoro-9,10-dihydrophenanthren-2-yl)-1H-imidazol-2-yl)pyrrolidine prepared in step 8 as the starting material according to the method in step 5 of Example 1.

LC-MS m/z: [M+H]⁺=573.4.

Step 10 Methyl N-((2S)-1-((2S)-2-(5-(7-(2-((S)-1-((S)-2-((methoxycarbonyl)amino)-3-methylbutanoyl)pyrrolidin-2-yl)-1H-imidazol-5-yl)-9,9,10,10-tetrafluoro-9,10-dihydrophenanthren-2-yl))-1H-benzo[d]imidazol-2-yl)pyrrolidin-1-yl)-3-methyl-1-oxobutan-2-yl)carbamate

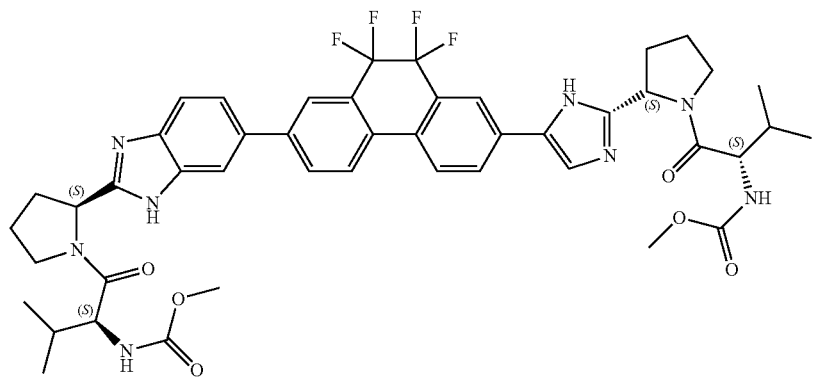

The title compound was prepared by using compound (S)-2-(5-(7-(2-((S)-pyrrolidin-2-yl)-1H-benzo[d]imidazol-6-yl)-9,9,10,10-tetrafluoro-9,10-dihydrophenanthren-2-yl)-1H-imidazol-2-yl)pyrrolidine prepared in step 9 and MOC-valine as the starting materials according to the method in step 6 of Example 1.

LC-MS m/z: [M+H]⁺=887.5.

¹HNMR: (500 MHz, DMSO) δ ppm: 8.34~8.36 (3H, m), 8.17~8.20 (4H, m), 8.07 (1H, s), 7.78~7.83 (2H, m), 5.15~5.18 (1H, m), 4.80 (1H, s), 4.60 (1H, s), 4.24~4.25 (1H, m), 4.15~4.17 (1H, m), 3.87~3.91 (1H, m), 3.60 (3H, s), 3.59 (3H, s), 3.20~3.21 (1H, m), 2.79~2.81 (1H, m), 2.67~2.69 (1H, m), 2.39~2.42 (1H, m), 2.20~2.28 (1H, m), 2.04~2.07 (2H, m), 1.81~1.88 (2H, m), 1.58~1.61 (2H, m), 1.27~1.33 (1H, m), 0.84~0.99 (12H, m).

Example 10

Methyl N-((2S)-1-((2S)-2-(6-(7-(2-((1R,3S,4S)-2-((S)-2-((methoxycarbonyl)amino)-3-methylbutanoyl)-2-azabicyclo[2.2.1]heptan-3-yl)-1H-benzo[d]imidazol-6-yl)-9,9,10,10-tetrafluoro-9,10-dihydrophenanthren-2-yl))-1H-imidazol-2-yl)pyrrolidin-1-yl)-3-methyl-1-oxobutan-2-yl)carbamate

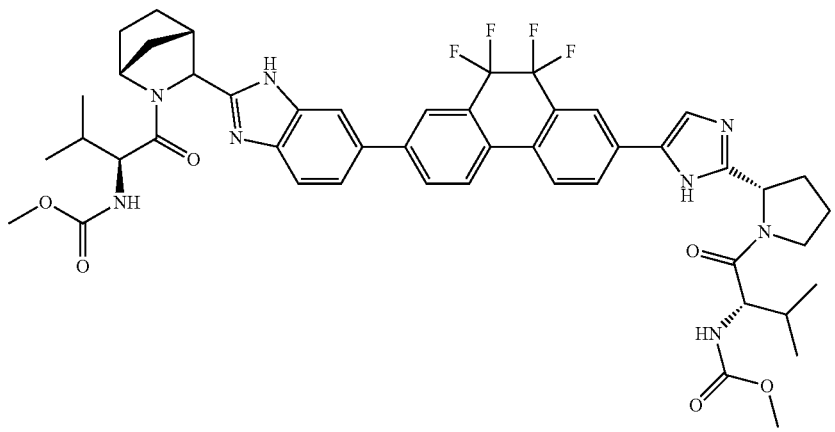 [SMILES: COC(=O)N[C@H](C(=O)N1CCC[C@H]1c1ncc(-c2ccc3c(c2)C(F)(F)C(F)(F)c2cc(-c4ccc5nc(C6[C@H]7CC[C@H](C7)N6C(=O)[C@@H](NC(=O)OC)C(C)C)[nH]c5c4)ccc2-3)[nH]1)C(C)C]

Step 1 (1R,3S,4S)-2-tert-butoxycarbonyl-3-(2-amino-4-bromophenylamino carbonyl)-2-azabicyclo[2.2.1]heptane

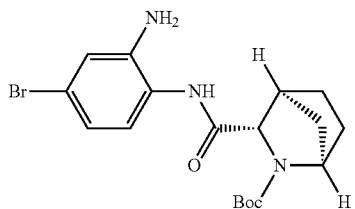 [SMILES: CC(C)(C)OC(=O)N1[C@@H]2CC[C@@H](C2)[C@H]1C(=O)Nc1ccc(Br)cc1N]

The title compound was prepared by using 4-bromo-o-phenylenediamine and (1R,3S,4S)-2-(tert-butoxycarbonyl)-2-azabicyclo[2.2.1]heptan-3-methanoic acid as the starting materials according to the method in step 5 of Example 9.
LC-MS m/z: [M+H]⁺=410, calcd: 410.1.

Step 2 (1R,3S,4S)-2-tert-butoxycarbonyl-3-(6-bromo-1H-benzo[d]imidazol-2-yl)-2-azabicyclo[2.2.1]heptane

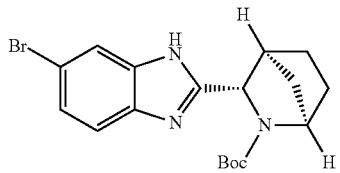 [SMILES: CC(C)(C)OC(=O)N1[C@@H]2CC[C@@H](C2)[C@H]1c1nc2ccc(Br)cc2[nH]1]

The title compound was prepared by using compound (1R,3S,4S)-2-tert-butoxy carbonyl-3-(2-amino-4-bromophenylaminocarbonyl)-2-azabicyclo[2.2.1]heptane prepared in step 1 as the starting material according to the method in step 6 of Example 9.
LC-MS m/z: [M+F]⁺=392.2.

Step 3 (1R,3S,4S)-2-tert-butoxycarbonyl-3-(6-(4,4,5,5-tetramethyl-1,3,2-dioxaborolan-2-yl)-1H-benzo[d]imidazol-2-yl)-2-azabicyclo[2.2.1]heptane

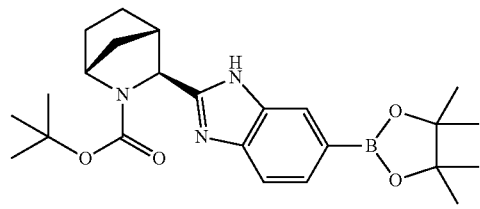 [SMILES: CC(C)(C)OC(=O)N1[C@@H]2CC[C@@H](C2)[C@H]1c1nc2ccc(B3OC(C)(C)C(C)(C)O3)cc2[nH]1]

The title compound was prepared by using compound (1R,3 S,4 S)-2-tert-butoxy carbonyl-3-(6-bromo-1H-benzo[d]imidazol-2-yl)-2-azabicyclo[2.2.1]heptane prepared in step 2 as the starting material according to the method in step 8 of Example 1.
¹HNMR (300 MHz, CDCl₃): δ: 10.65 (1H, br), 8.01 (1H, m), 7.66 (2H, d), 4.55 (1H, s), 4.15 (1H, m), 3.49 (1H, m), 1.9 (2H, m), 1.7 (4H, m), 1.52 (9H, s), 1.35 (12H, s).
LC-MS m/z: [M+H]⁺=440.3.

Step 4 (1R,3S,4S)-2-tert-butoxycarbonyl-3-(6-(7-(2-((S)-1-(tert-butoxycarbonyl)pyrrolidin-2-yl)-1H-imidazol-5-yl)-9,9,10,10-tetrafluoro-9,10-dihydro phenanthren-2-yl)-1H-benzo[d]imidazol-2-yl)-2-azabicyclo[2.2.1]heptane

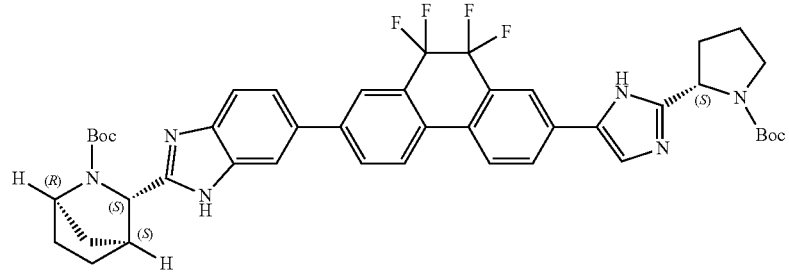

The title compound was prepared by using compound (1R,3S,4S)-2-tert-butoxycarbonyl-3-(6-(4,4,5,5-tetramethyl-1,3,2-dioxaborolan-2-yl)-1H-benzo[d]imidazol-2-yl)-2-azabicyclo[2.2.1]heptane prepared in step 3 and compound (S)-1-tert-butoxy carb onyl-2-(5-(7-bromo-9,9,10,10-tetrafluoro-9,10-dihydrophenanthren-2-yl)-1H-imidazol-2-yl)pyrrolidine prepared in step 4 of Example 9 as the starting materials according to the method in step 8 of Example 9.
LC-MS m/z: [M+H]⁺=799.4.

Step 5 (1R,3S,4S)-3-(6-(7-(2-((S)-pyrrolidin-2-yl)-1H-imidazol-5-yl)-9,9,10,10-tetrafluoro-9,10-dihydrophenanthren-2-yl)-1H-benzo[d]imidazol-2-yl)-2-azabicyclo[2.2.1]heptane

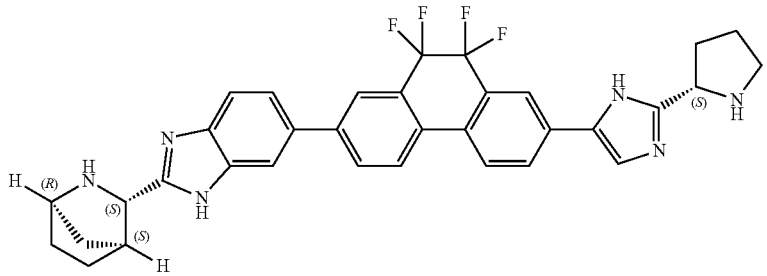

The title compound was prepared by using compound (1R,3S,4S)-2-tert-butoxycarbonyl-3-(6-(7-(2-((S)-1-(tert-butoxycarbonyl)pyrrolidin-2-yl)-1H-imidazol-5-yl)-9,9,10,10-tetrafluoro-9,10-dihydrophenanthren-2-yl)-1H-benzo[d]imidazol-2-yl)-2-azabicyclo[2.2.1]heptane prepared in step 4 as the starting material according to the method in step 5 of Example 1.

LC-MS m/z: [M+H]$^+$=599.3.

Step 6 Methyl N-((2S)-1-((2S)-2-(6-(7-(2-((1R,3S,4S)-2-((S)-2-((methoxycarbonyl)amino)-3-methylbutanoyl)-2-azabicyclo[2.2.1]heptan-3-yl)-1H-benzo[d]imidazol-6-yl)-9,9,10,10-tetrafluoro-9,10-dihydrophenanthren-2-yl))-1H-imidazol-2-yl)pyrrolidin-1-yl)-3-methyl-1-oxobutan-2-yl) carbamate

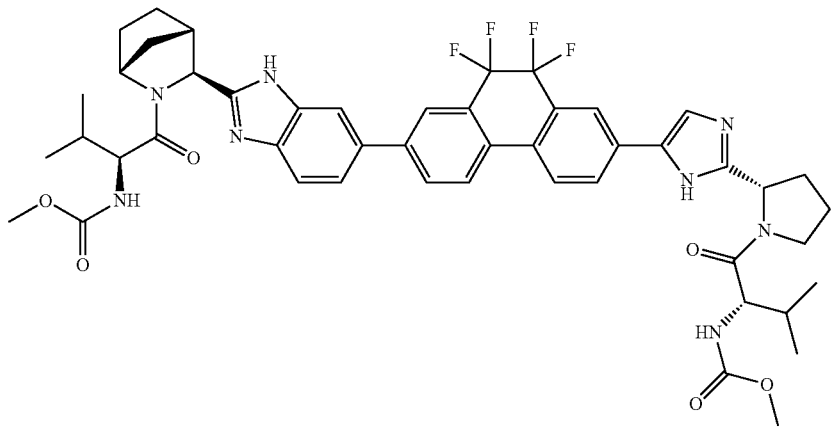 [SMILES: COC(=O)N[C@H](C(=O)N1CCC[C@H]1c1ncc(-c2ccc3c(c2)C(F)(F)C(F)(F)c2cc(-c4ccc5nc([C@@H]6[C@H]7CC[C@H](C7)N6C(=O)[C@@H](NC(=O)OC)C(C)C)[nH]c5c4)ccc2-3)[nH]1)C(C)C]

The title compound was prepared by using compound (1R,3S,4S)-3-(6-(7-(2-((S)-pyrrolidin-2-yl)-1H-imidazol-5-yl)-9,9,10,10-tetrafluoro-9,10-dihydrophenanthren-2-yl)-1H-benzo[d]imidazol-2-yl)-2-azabicyclo[2.2.1]heptane prepared in step 5 and MOC-valine as the starting materials according to the method in step 6 of Example 1.

LC-MS m/z: [M+H]$^+$=913.5.

$^1$HNMR: (500 MHz, DMSO) δ ppm: 8.32~8.35 (2H, m), 8.26~8.28 (1H, m), 8.16~8.19 (4H, m), 8.06 (1H, s), 7.76 (2H, s), 7.27~7.35 (2H, m), 5.18~5.20 (1H, m), 4.79 (1H, s), 4.61 (1H, s), 4.15~4.26 (3H, m), 3.88~3.91 (2H, m), 3.61 (3H, s), 3.60 (3H, s), 2.78 (1H, m), 2.38~2.39 (2H, m), 2.13~2.20 (1H, m), 2.06~2.10 (4H, m), 1.95~1.97 (1H, m), 1.81~1.87 (2H, m), 1.29~1.33 (1H, m), 0.87~1.02 (12H, m).

Example 11

Methyl N-((2S)-1-((S)-2-(6-(7-((S)-2-(7-((S)-2-((methoxycarbonyl)amino)-3-methylbutanoyl)-1,4-dioxa-7-azaspiro[4.4]nonan-8-yl)-1H-imidazol-5-yl)-9,9,10,10-tetrafluoro-9,10-dihydrophenanthren-2-yl)-1H-benzo[d]imidazol-2-yl)pyrrolidin-1-yl)-3-methyl-1-oxo butan-2-yl)carbamate 218 mg product 7-benzyloxycarbonyl-(S)-8-methoxycarbonyl-1,4-dioxa-7-azaspiro[4.4]nonane obtained in step 1 was weighted into a reaction flask and dissolved by adding 5 mL methanol, and 43 mg palladium on carbon was added thereto with stirring at room temperature. The reaction was performed under hydrogen gas at room temperature for 1 hour. The mixture was filtered, and concentrated to give the title compound, which was used directly in the next reaction step.

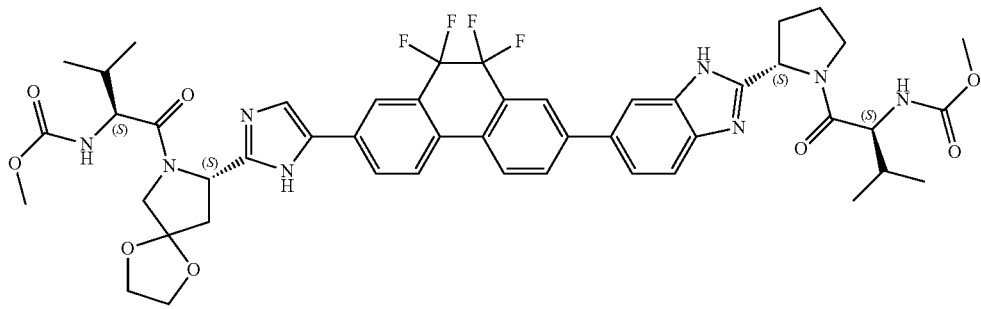

Step 1 Preparation of 7-benzyloxycarbonyl-(S)-8-methoxycarbonyl-1,4-dioxa-7-azaspiro[4.4]nonane

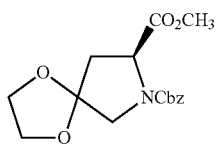 [SMILES: COC(=O)[C@@H]1CC2(CN1C(=O)OCc1ccccc1)OCCO2]

10 g (S)-1-benzyloxycarbonyl-2-methoxycarbonyl-4-oxopyrrole was weighted into a reaction flask and dissolved by adding 100 mL toluene and 100 mL ethylene glycol, and 620 mg p-toluenesulfonic acid was added thereto. The mixture was refluxed with water in Dean-Stark at 165° C. for 5 h. After completion of the reaction, the mixture was concentrated to remove toluene, and extracted by adding ethyl acetate and water. The organic layer was washed with saturated brine, dried and concentrated to give the title compound.

Step 2 Preparation of (S)-8-methoxycarbonyl-1,4-dioxa-7-azaspiro[4.4]nonane

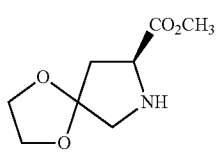 [SMILES: COC(=O)[C@@H]1CC2(CN1)OCCO2]

Step 3 Preparation of (S)-7-((S)-2-(methoxycarbonylamino)-3-methylbutanoyl)-8-methoxycarbonyl-1,4-dioxa-7-azaspiro[4.4]nonane

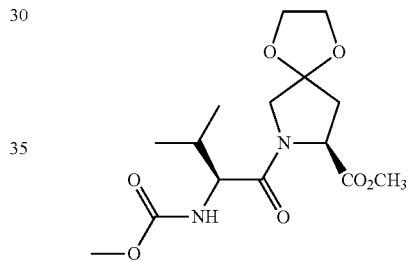

187 mg product (S)-8-methoxycarbonyl-1,4-dioxa-7-azaspiro[4.4]nonane obtained in step 2, 380 mg HATU, 0.5 mL DIEA and 175 mg MOC-valine were placed into a reaction flask, and 20 mL dichloromethane was added thereto. The reaction was performed at room temperature for 2 h. After completion of the reaction, the reaction mixture was extracted by adding dichloromethane and water. The organic layer was dried, filtered and purified by column chromatography to give the title compound.

Step 4 Preparation of (S)-7-((S)-2-(methoxycarbonylamino)-3-methylbutanoyl)-1,4-dioxa-7-azaspiro[4.4]nonan-8-methanoic acid

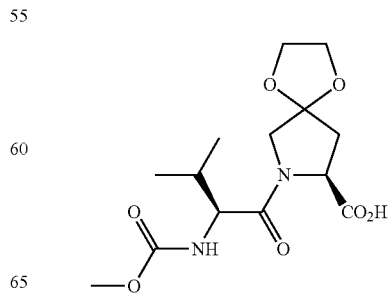

2 g product (S)-7-((S)-2-(methoxycarbonylamino)-3-methylbutanoyl)-8-methoxycarbonyl-1,4-dioxa-7-azaspiro[4.4]nonane obtained in step 3 was weighted into a reaction flask and dissolved by adding 20 mL 1,4-dioxane, and 15 mL 1 N LiOH aqueous solution was added thereto. After reaction at room temperature for 1 h, the pH was adjusted to 4-5. The mixture was extracted with dichloromethane. The organic phase was dried, concentrated, and used directly in the next reaction step.

Step 5 Preparation of (S)-2-(6-(7-bromo-9,9,10,10-tetrafluoro-9,10-dihydro phenanthren-2-yl)-1H-benzo[d]imidazol-2-yl)-1-tert-butoxycarbonylpyrrole

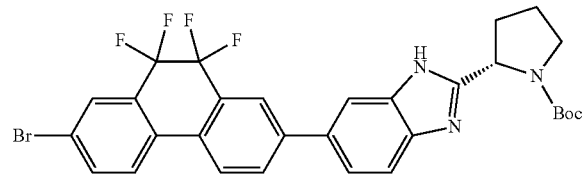 [SMILES: CC(C)(C)OC(=O)N1CCC[C@H]1c1nc2ccc(-c3ccc4c(c3)C(F)(F)C(F)(F)c3cc(Br)ccc3-4)cc2[nH]1]

1 g product 2,7-dibromo-9,9,10,10-tetrafluoro-9,10-dihydrophenanthrene obtained in step 7 of Example 1, 1.2 g compound (S)-1-tert-butoxycarbonyl-2-(6-(4,4,5,5-tetramethyl-1,3,2-dioxaborolan-2-yl)-1H-benzo[d]imidazol-2-yl) pyrrolidine obtained in step 7 of Example 9 and 283 mg Pd(PPh$_3$)$_4$ were weighted into a reaction flask and dissolved by adding 20 ml N,N-dimethylacetamide (DME), and then 4 mL K$_2$CO$_3$ aqueous solution (2 M) was added thereto. The reaction was refluxed under argon gas protection for 4 h. After completion of the reaction, the reaction mixture was extracted with ethyl acetate (3×20 mL), dried, filtered, concentrated and purified by column chromatography to give the title compound.

ESI-MS m/z: [M+H]$^+$=616.

Step 6 Preparation of (S)-2-(6-(7-(2-bromoacetyl)-9,9,10,10-tetrafluoro-9,10-dihydrophenanthren-2-yl)-1H-benzo[d]imidazol-2-yl)-1-tert-butoxycarbonyl pyrrole

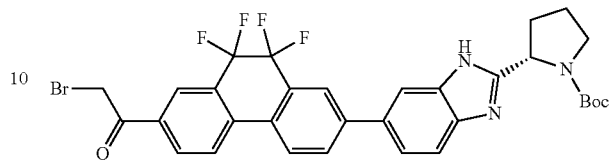

930 mg product (S)-2-(6-(7-bromo-9,9,10,10-tetrafluoro-9,10-dihydro phenanthren-2-yl)-1H-benzo[d]imidazol-2-yl)-1-tert-butoxycarbonylpyrrole obtained in step 5, 653 mg tributyl(1-ethoxyethenyl)stannane and 106 mg Pd (PPh$_3$)$_2$Cl$_2$ were weighted into a reaction flask and dissolved by adding 20 mL dioxane. The reaction was performed under argon gas protection at 80° C. for 3 h. The mixture was cooled to room temperature, 5 mL water and 270 mg NBS were added thereto, and the reaction was performed at room temperature for 2 h. After completion of the reaction, the reaction mixture was extracted with ethyl acetate (3×20 mL), dried, filtered, concentrated and purified by column chromatography to give the title compound.

ESI-MS m/z: [M+H]$^+$=658.

Step 7 Preparation of (S)-2-(6-(7-(2-((S)-7-((S)-2-(methoxycarbonylamino)-3-methylbutanoyl)-1,4-dioxa-7-azaspiro[4.4]nonan-8-yl)-1H-imidazol-5-yl)-9,9,10,10-tetrafluoro-9,10-dihydrophenanthren-2-yl)-1H-benzo[d]imidazol-2-yl)-1-tert-butoxycarbonylpyrrole

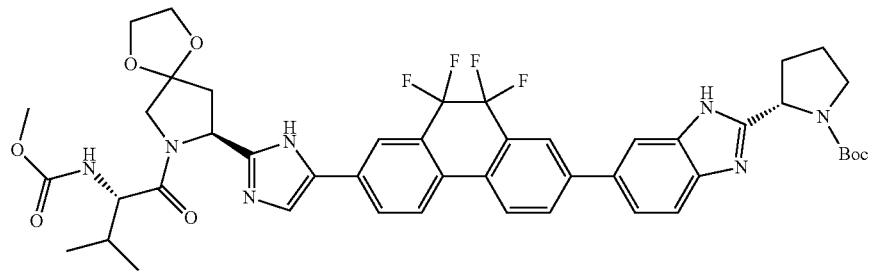 [SMILES: COC(=O)N[C@H](C(=O)N1CC2(C[C@H]1c1ncc(-c3ccc4c(c3)C(F)(F)C(F)(F)c3cc(-c5ccc6nc([C@@H]7CCCN7C(=O)OC(C)(C)C)[nH]c6c5)ccc3-4)[nH]1)OCCO2)C(C)C]

220 mg product (S)-2-(6-(7-(2-bromoacetyl)-9,9,10,10-tetrafluoro-9,10-dihydrophenanthren-2-yl)-1H-benzo[d]imidazol-2-yl)-1-tert-butoxycarbonylpyrrole obtained in step 6 and 100 mg product (S)-7-((S)-2-(methoxycarbonylamino)-3-methylbutanoyl)-1,4-dioxa-7-azaspiro[4.4]nonan-8-methanoic acid obtained in step 4 were weighed into a reaction flask and dissolved by adding 5 mL acetonitrile, and 77 mg DIPEA was added thereto. The reaction was refluxed for 0.5 h. The reaction mixture was concentrated, and 10 mL toluene and 254 mg ammonium acetate were added thereto. The reaction was performed at 130° C. for 2 h. After completion of the reaction, the reaction mixture was concentrated and purified by column chromatography to give the title compound.

ESI-MS m/z: [M+H]$^+$=888.

Step 8 Preparation of methyl N—((S)-3-methyl-1-oxo-1-((S)-8-(5-(7-(2-((S)-pyrrol-2-yl)-1H-benzo[d]imidazol-6-yl)-9,9,10,10-tetrafluoro-9,10-dihydrophenanthren-2-yl)-1H-imidazol-2-yl)-1,4-dioxa-7-azaspiro[4.4]nonan-7-yl)butan-2-yl)carbamate

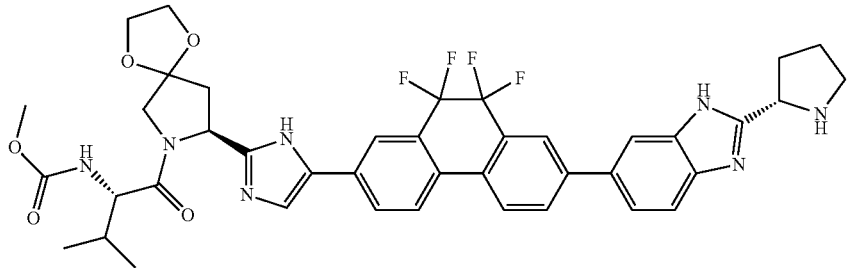 [SMILES: COC(=O)N[C@H](C(=O)N1CC2(C[C@H]1c1ncc(-c3ccc4c(c3)C(F)(F)C(F)(F)c3cc(-c5ccc6nc([C@@H]7CCCN7)[nH]c6c5)ccc3-4)[nH]1)OCCO2)C(C)C]

130 mg product (S)-2-(6-(7-(2-((S)-7-((S)-2-(methoxycarbonylamino)-3-methylbutanoyl)-1,4-dioxa-7-azaspiro[4.4]nonan-8-yl)-1H-imidazol-5-yl)-9,9,10,10-tetrafluoro-9,10-dihydrophenanthren-2-yl)-1H-benzo[d]imidazol-2-yl)-1-tert-butoxycarbonylpyrrole prepared in step 7 was weighted into a reaction flask and dissolved by adding 3 mL dichloromethane, and 1 mL trifluoroacetic acid was added thereto. The reaction was performed at room temperature for 1 h. After completion of the reaction, the reaction mixture was concentrated to dryness, and thereto water was added, as wells as a saturated sodium bicarbonate solution to adjust the pH to 8. The mixture was filtered, washed with water and dried to give the title compound.

ESI-MS m/z: [M+H]$^+$=788.

Step 9 Methyl N-((2S)-1-((S)-2-(5-(7-((S)-2-(7-((S)-2-((methoxycarbonyl)amino)-3-methylbutanoyl)-1,4-dioxa-7-azaspiro[4.4]nonan-8-yl)-1H-imidazol-5-yl)-9,9,10,10-tetrafluoro-9,10-dihydrophenanthren-2-yl)-1H-benzo[d]imidazol-2-yl) pyrrolidin-1-yl)-3-methyl-1-oxobutan-2-yl)carbamate

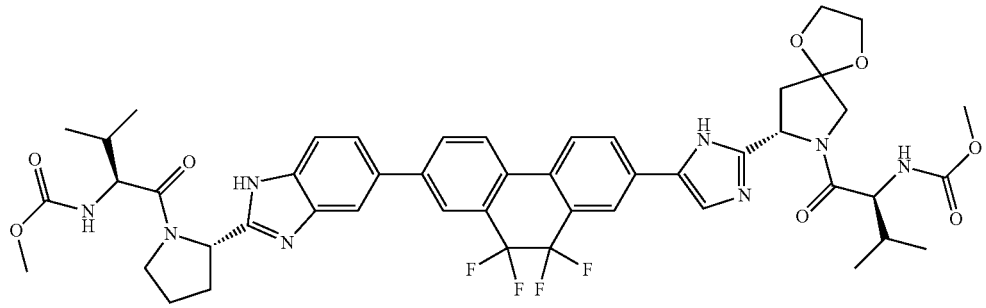 [SMILES: COC(=O)N[C@H](C(=O)N1CC2(C[C@H]1c1ncc(-c3ccc4c(c3)C(F)(F)C(F)(F)c3cc(-c5ccc6[nH]c([C@@H]7CCCN7C(=O)[C@@H](NC(=O)OC)C(C)C)nc6c5)ccc3-4)[nH]1)OCCO2)C(C)C]

115 mg product methyl N—((S)-3-methyl-1-oxo-1-((S)-8-(5-(7-(2-((S)-pyrrol-2-yl)-1H-benzo[d]imidazol-6-yl)-9,9,10,10-tetrafluoro-9,10-dihydrophenanthren-2-yl)-1H-imidazol-2-yl)-1,4-dioxa-7-azaspiro[4.4]nonan-7-yl)butan-2-yl)carbamate obtained in step 8 and 31 mg MOC-valine were weighted into a reaction flask and dissolved by adding 10 mL dichloromethane, and 40 mg DIPEA and 86 mg 2-(7-azabenzotriazol-1-yl)-N,N,N',N'-tetramethyluronium hexafluorophosphate (HATU) were added thereto. The reaction was performed at room temperature for 15 h. The reaction mixture was concentrated and purified by column chromatography to obtain the target compound.

$^1$H NMR (500 MHz, d$_6$-DMSO) δ 12.32 (s, 1H), 12.09 (s, 1H), 8.09-8.20 (m, 6H), 7.91 (s, 1H), 7.74 (s, 1H), 7.63 (s, 2H), 7.27 (s, 2H), 5.21 (s, 1H), 5.10 (s, 1H), 3.68-4.07 (m, 12H), 3.32 (s, 6H), 1.95-2.09 (m, 6H), 0.88 (m, 12H).

ESI-MS m/z: [M+H]$^+$=945.

Example 12

Methyl N-((2S)-1-((S)-2-(6-(7-((S)-2-(5-((S)-2-((methoxycarbonyl)amino)-3-methylbutanoyl)-5-azaspiro[2.4]heptan-6-yl)-1H-imidazol-5-yl)-9,9,10,10-tetrafluoro-dihydrophenanthren-2-yl)-1H-benzo[d]imidazol-2-yl)pyrrolidin-1-yl)-3-methyl-1-oxobutan-2-yl)carbamate

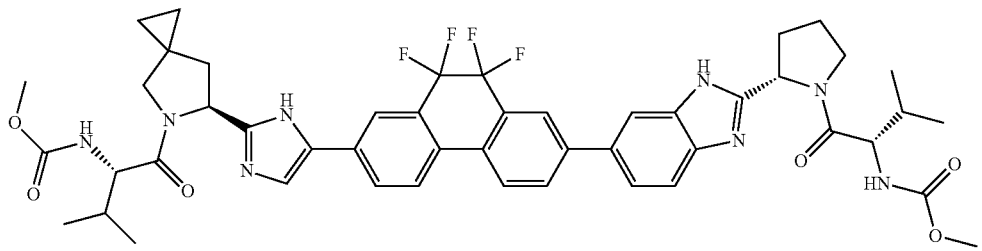 [SMILES: COC(=O)N[C@H](C(=O)N1CC2(CC2)C[C@H]1c1ncc(-c2ccc3c(c2)C(F)(F)C(F)(F)c2cc(-c4ccc5nc([C@@H]6CCCN6C(=O)[C@@H](NC(=O)OC)C(C)C)[nH]c5c4)ccc2-3)[nH]1)C(C)C]

Step 1 Preparation of 5-tert-butoxycarbonyl-(S)-6-(5-(7-(2-((S)-1-(tert-butoxycarbonyl)pyrrol-2-yl)-1H-benzo[d]imidazol-6-yl)-9,9,10,10-tetrafluoro-9,10-dihydrophenanthren-2-yl)-1H-imidazol-2-yl)-5-azaspiro[2.4]heptane

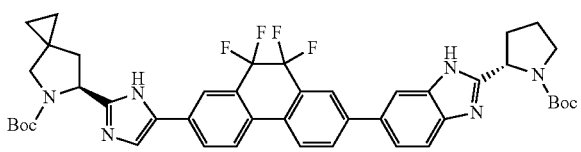 [SMILES: CC(C)(C)OC(=O)N1CC2(CC2)C[C@H]1c1ncc(-c2ccc3c(c2)C(F)(F)C(F)(F)c2cc(-c4ccc5nc([C@@H]6CCCN6C(=O)OC(C)(C)C)[nH]c5c4)ccc2-3)[nH]1]

The title compound was prepared by using product (S)-2-(6-(7-(2-bromoacetyl)-9,9,10,10-tetrafluoro-9,10-dihydrophenanthren-2-yl)-1H-benzo[d]imidazol-2-yl)-1-tert-butoxycarbonylpyrrole obtained in step 6 of Example 11 and potassium (S)-5-(tert-butoxycarbonyl)-5-azaspiro[2.4]heptan-6-formate as the starting materials according to the method in step 7 of Example 11.

ESI-MS m/z: [M+M]$^+$=799.

Step 2 Preparation of 6-(7-(2-((S)-5-azaspiro[2.4]heptan-6-yl)-1H-imidazol-5-yl)-9,9,10,10-tetrafluoro-9,10-dihydrophenanthren-2-yl)-2-((S)-pyrrol-2-yl)-1H-benzo[d]imidazole The title compound was prepared by using product 5-tert-butoxycarbonyl-(S)-6-(5-(7-(2-((S)-1-(tert-butoxycarbonyl)pyrrol-2-yl)-1H-benzo[d]imidazol-6-yl)-9,9,10,10-tetrafluoro-9,10-dihydrophenanthren-2-yl)-1H-imidazol-2-yl)-5-azaspiro[2.4]heptane obtained in step 1 as the starting material according to the method in step 8 of Example 11.

ESI-MS m/z: [M+H]$^+$=599.

Step 3 Preparation of methyl N-((2S)-1-((S)-2-(6-(7-((S)-2-(5-((S)-2-((methoxy carbonyl)amino)-3-methylbutanoyl)-5-azaspiro[2.4]heptan-6-yl)-1H-imidazol-5-yl)-9,9,10,10-tetrafluoro-9,10-dihydrophenanthren-2-yl)-1H-benzo[d]imidazol-2-yl)pyrrolidin-1-yl)-3-methyl-1-oxobutan-2-yl)carbamate

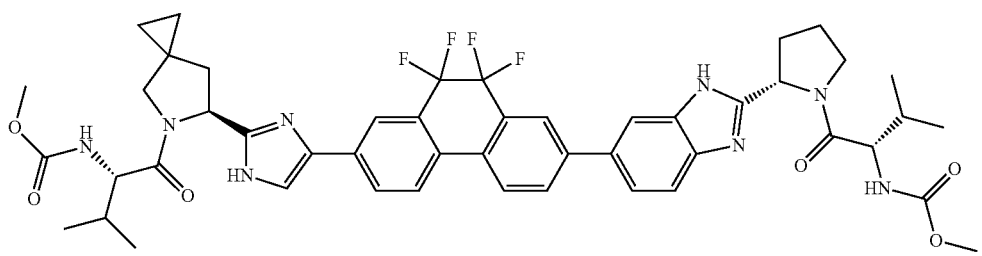 [SMILES: COC(=O)N[C@H](C(=O)N1CC2(CC2)C[C@H]1c1nc(-c2ccc3c(c2)C(F)(F)C(F)(F)c2cc(-c4ccc5nc([C@@H]6CCCN6C(=O)[C@@H](NC(=O)OC)C(C)C)[nH]c5c4)ccc2-3)c[nH]1)C(C)C]

The title compound was prepared by using product 6-(7-(2-((S)-5-azaspiro[2.4]heptan-6-yl)-1H-imidazol-5-yl)-9,9,10,10-tetrafluoro-9,10-dihydrophenanthren-2-yl)-2-((S)-pyrrol-2-yl)-1H-benzo[d]imidazole obtained in step 2 and MOC-valine as the starting materials according to the method in step 9 of Example 11.

$^1$H NMR (500 MHz, d$_6$-DMSO) δ 12.32 (s, 1H), 11.97 (s, 1H), 8.08-8.21 (m, 6H), 7.77-7.90 (m, 2H), 7.59 (s, 2H), 7.32 (m, 2H), 5.21 (m, 2H), 3.99-4.07 (m, 2H), 3.64-3.90 (m, 4H), 3.54-3.57 (m, 6H), 1.91-2.24 (m, 8H), 0.60-0.95 (m, 16H).

ESI-MS m/z: [M+H]$^+$=913.

Example 13

Preparation of dimethyl 42S,2'S,3R,3'R)-((2S,2'S)-2,2'-(4,4'-(9,9,10,10-tetrafluoro-9,10-dihydrophenanthren-2,7-diyl)bis(1H-imidazol-5,2-diyl))bis(pyrrolidin-2,1-diyl))bis(3-methoxy-1-oxobutan-2,1-diyl))dicarbamate

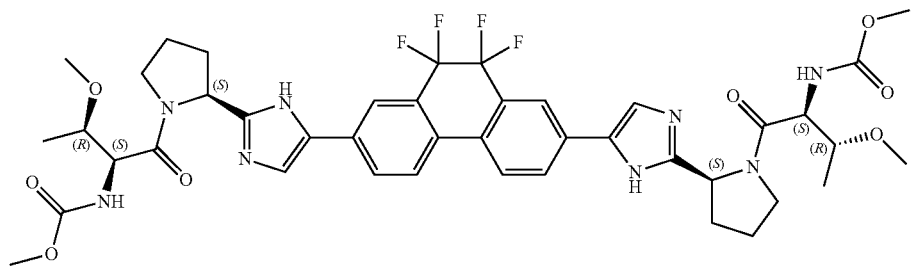

Step 1 Preparation of (2S,3R)-3-methoxy-2-(methoxycarbonylamino)butanoic acid

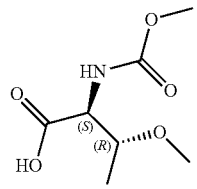

3.0 g O-methyl-L-threonine and 0.902 g sodium hydroxide were weighted into a dried 100 mL one-necked flask, into which 15 mL water was added, and at 0° C., 1.74 mL methyl chloroformate was added. The mixture was stirred under ice bath and naturally warmed to room temperature, and reacted for 12 h. After completion of the reaction, the reaction liquid was adjusted with 1 N HCl to pH 1, extracted with ethyl acetate (5×100 mL). The organic phase was dried, filtered, and concentrated to give the title compound, which was used directly in the next reaction step. MS (ESI): [M+H]$^+$=192.

Step 2 Preparation of dimethyl ((2S,2'S,3R,3'R)-((2S,2'S)-2,2'-(4,4'-(9,9,10,10-tetrafluoro-9,10-dihydrophenanthren-2,7-diyl)bis(1H-imidazol-5,2-diyl))bis(pyrrolidin-2,1-diyl))bis(3-methoxy-1-oxobutan-2,1-diyl))dicarbamate

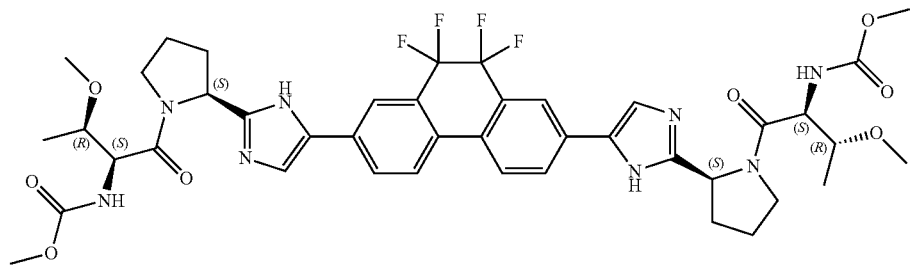

The title compound was prepared by using compound (2S,2'S)-2,2'-(5,5'-(9,9,10,10-tetrafluoro-9,10-dihydrophenanthren-2,7-diyl)bis(1H-imidazol-5,2-diyl))dipyrrolidine obtained in step 3 of Example 7 and product (2S,3R)-3-methoxy-2-(methoxycarbonylamino)butanoic acid obtained in step 1 as the starting materials according to the method in step 7 of Example 3.

$^{1}$H NMR: 300 MHz, DMSO-$d_6$) δ 11.96-12.13 (m, 2H), 7.89-8.32 (m, 6H), 7.75-7.83 (m, 2H), 7.22-7.29 (m, 2H), 5.03-5.09 (m, 2H), 4.25-4.33 (m, 2H), 3.60-3.92 (m, 4H), 3.40-3.59 (m, 8H), 3.18 (s, 6H), 1.89-2.32 (m, 8H), 0.96-1.18 (m, 6H).

MS (ESI): [M+H]$^{+}$=869.

Example 14

Methyl N-((2S)-1-((S)-2-(5-(7-((S)-2-(7-((S)-2-((methoxycarbonyl)amino)-3-methylbutanoyl)-1,4-dioxa-7-azaspiro[4.4]nonan-8-yl)-1H-imidazol-5-yl)-9,9,10,10-tetrafluoro-9,10-dihydrophenanthren-2-yl)-1H-imidazol-2-yl) pyrrolidin-1-yl)-3-methyl-1-oxobutan-2-yl)carbamate

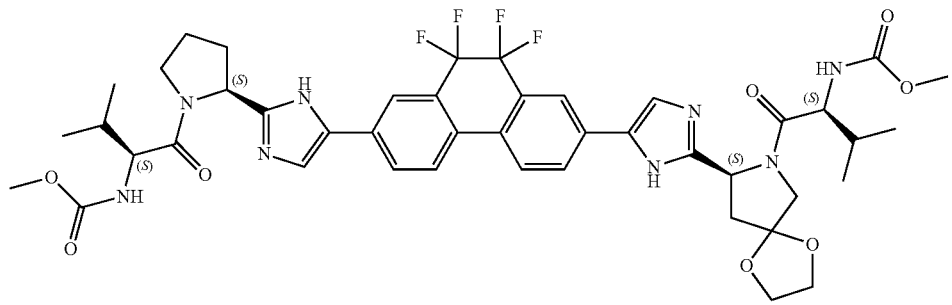

Step 1 Preparation of (S)-2-(2-(7-(4(S)-7-((S)-2-(methoxycarbonylamino)-3-methylbutanoyl)-1,4-dioxa-7-azaspiro[4.4]nonan-8-yl)carbonyloxy)acetyl)-9,9,10,10-tetrafluoro-9,10-dihydrophenanthren-2-yl)-2-oxoethoxycarbonyl)-1-tert-butoxycarbonylpyrrole

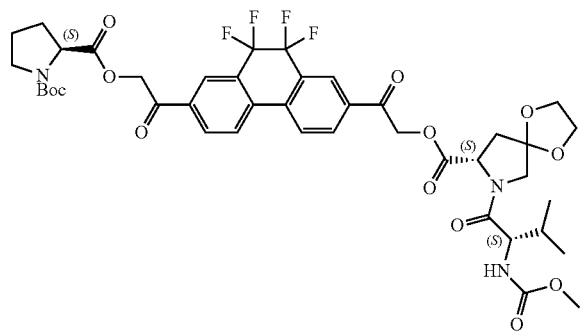

1 g compound 1,1'-(9,9,10,10-tetrafluoro-9,10-dihydrophenanthren-2,7-diyl)bis(2-bromoethanone) prepared in step 3 of Example 3 was weighted into a 50 mL reaction flask, and 25 mL acetonitrile, 650 mg compound (S)-7-((S)-2-(methoxy carbonylamino)-3-methylbutanoyl)-1,4-dioxa-7-azaspiro[4.4]nonan-8-methanoic acid obtained in step 4 of Example 11 and 1 mL N,N-diisopropylethylamine (DIPEA) were added thereto. After reaction at room temperature for 0.5 h, 430 mg (tert-butoxycarbonyl)-L-proline was added. The reaction was performed at room temperature for 0.5 h. After completion of the reaction, the reaction liquid was concentrated to give the title compound.

MS (ESI): [M+H]=878.3.

Step 2 Preparation of (S)-2-(5-(7-(2-((S)-7-((S)-2-(methoxycarbonylamino)-3-methylbutanoyl)-1,4-dioxa-7-azaspiro[4.4]nonan-8-yl)-1H-imidazol-5-yl)-9,9,10,10-tetrafluoro-9,10-dihydrophenanthren-2-yl)-1H-imidazol-2-yl)-1-tert-butoxy carbonylpyrrole

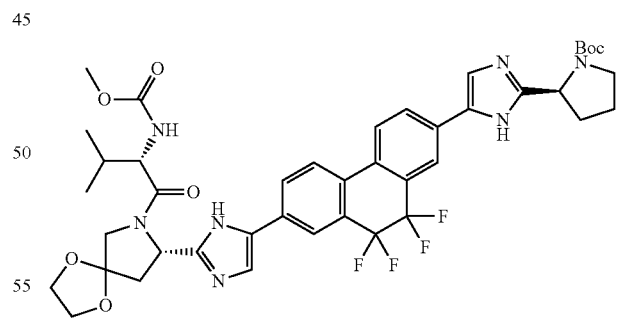

The title compound was prepared by using product (S)-2-(2-(7-(4(S)-7-((S)-2-(methoxy carbonylamino)-3-methylbutanoyl)-1,4-dioxa-7-azaspiro[4.4]nonan-8-yl)carbonyloxy)acetyl)-9,9,10,10-tetrafluoro-9,10-dihydrophenanthren-2-yl)-2-oxoethoxycarbonyl)-1-tert-butoxycarbonylpyrrole obtained in step 1 and ammonium acetate as the starting materials according to the method in step 2 of Example 2.

MS (ESI): [M+H]=838.

Step 3 (S)-2-(5-(7-(2-((S)-7-((S)-2-(methoxycarbonylamino)-3-methylbutanoyl)-1,4-dioxa-7-azaspiro[4.4]nonan-8-yl)-1H-imidazol-5-yl)-9,9,10,10-tetrafluoro-9,10-dihydrophenanthren-2-yl)-1H-imidazol-2-yl)pyrrole

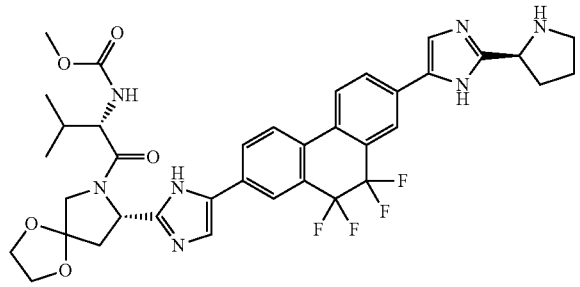 [SMILES: COC(=O)N[C@H](C(=O)N1CC2(C[C@H]1c1ncc(-c3ccc4c(c3)C(F)(F)C(F)(F)c3cc(-c5cnc([C@@H]6CCCN6)[nH]5)ccc3-4)[nH]1)OCCO2)C(C)C]

1 g product (S)-2-(5-(7-(2-((S)-7-((S)-2-(methoxycarbonylamino)-3-methyl butanoyl)-1,4-dioxa-7-azaspiro[4.4]nonan-8-yl)-1H-imidazol-5-yl)-9,9,10,10-tetrafluoro-9,10-dihydrophenanthren-2-yl)-1H-imidazol-2-yl)-1-tert-butoxy carbonyl pyrrole obtained in step 2 was weighted into a reaction flask and dissolved by adding 20 mL dichloromethane, and at 0-4° C., 5 mL trifluoroacetic acid was added thereto. The reaction was performed at room temperature for 2 h. The solvent was removed, and the mixture was drained with oil pump, to give the title compound, which was used directly in the next step.

MS (ESI): [M+H]=738.

Step 4 Preparation of methyl N-((2S)-1-((S)-2-(5-(7-((S)-2-(7-((S)-2-((methoxycarbonyl)amino)-3-methylbutanoyl)-1,4-dioxa-7-azaspiro[4.4]nonan-8-yl)-1H-imidazol-5-yl)-9,9,10,10-tetrafluoro-9,10-dihydrophenanthren-2-yl)-1H-imidazol-2-yl)pyrrolidin-1-yl)-3-methyl-1-oxobutan-2-yl) carbamate

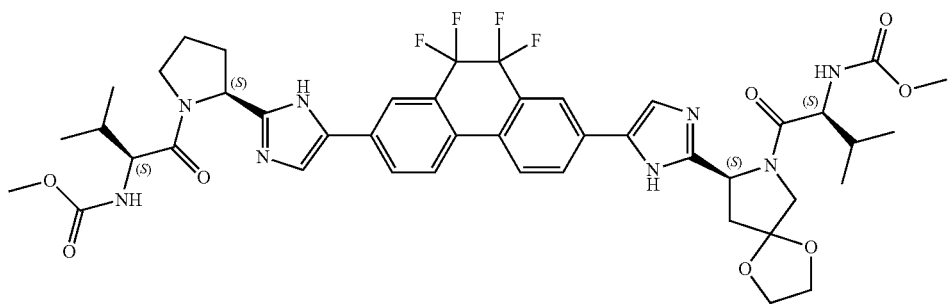

The title compound was prepared by using product (S)-2-(5-(7-(2-((S)-7-((S)-2-(methoxycarbonylamino)-3-methylbutanoyl)-1,4-dioxa-7-azaspiro[4.4]nonan-8-yl)-1H-imidazol-5-yl)-9,9,10,10-tetrafluoro-9,10-dihydrophenanthren-2-yl)-1H-imidazol-2-yl)pyrrole obtained in step 3 as the starting material according to the method in step 9 of Example 11.

$^1$HNMR: (500 MHz, DMSO-d6) δ: 11.97-12.04 (m, 2H), 8.01-8.15 (m, 6H), 7.75 (m, 2H), 7.25 (m, 2H), 5.08 (m, 2H), 3.75-5.09 (m, 10H), 3.55 (m, 6H), 1.96-2.42 (m, 8H), 0.88-0.96 (m, 12H).
ESI-MS m/z: [M+H]=895.

Example 15

2-methoxy-ethyl N-((2S)-1-((S)-2-(5-(7-(2-((S)-1-((S)-2-(methoxycarbonylamino)-3-methylbutanoyl)-pyrrol-2-yl)-1H-imidazol-5-yl)-9,9,10,10-tetrafluoro-9,10-dihydrophenanthren-2-yl)-1H-imidazol-2-yl)-pyrrol-1-yl)-3-methyl-1-oxo butan-2-yl) carbamate

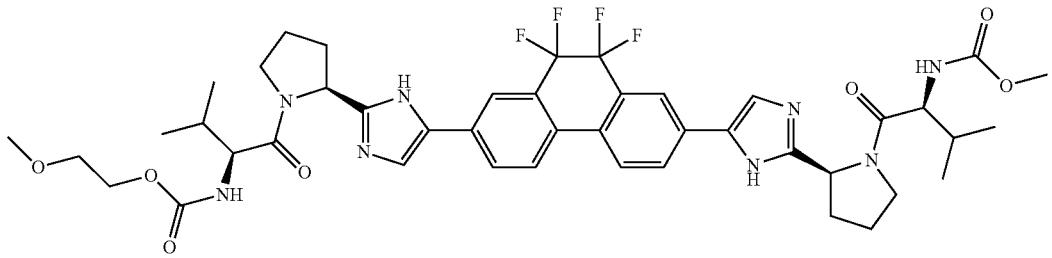

Step 1 Preparation of (S)-2-(((2-methoxyethoxy)carbonyl)amino)-3-methyl-butyric acid

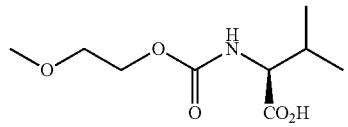

2.52 g triphosgene was weighted into a reaction flask, and at 0-4° C., 50 mL dichloromethane and 2.02 g pyridine were added thereto. 1.6 g ethylene glycol monomethyl ether was weighed and diluted with 5 mL methylene chloride, and added dropwise to the reaction flask. After reaction for 1 h, the reaction liquid was gradually warmed to room temperature and concentrated, and then was dissolved by adding 10 mL 1,4-dioxane and then ready for use.

1.17 g MOC-valine was weighted into another reaction flask, and 10 mL 2 N sodium hydroxide solution was added. The above 1,4-dioxane solution ready for use was added dropwise to the reaction flask with stirring at room temperature. The reaction was performed at room temperature for 12 h. After completion of the reaction, the pH was adjusted to 4-5 and the mixture was extracted with chloroform. The organic phase was concentrated to give the title compound, which was used directly in the next reaction step.

Step 2 preparation of (S)-2-(5-(7-(2-((S)-1-((S)-2-(methoxycarbonylamino)-3-methylbutanoyl)-pyrrol-2-yl)-1H-imidazol-5-yl)-9,9,10,10-tetrafluoro-9,10-dihydrophenanthren-2-yl)-1H-imidazol-2-yl)pyrrole

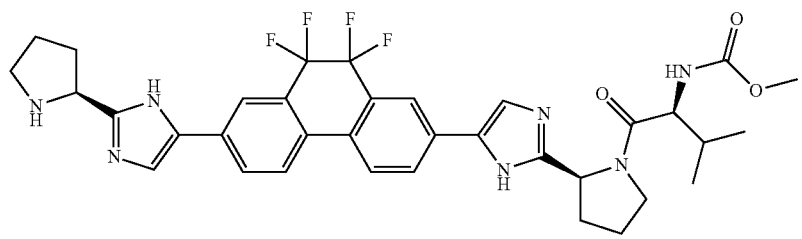 [SMILES: COC(=O)N[C@H](C(=O)N1CCC[C@H]1c1ncc(-c2ccc3c(c2)C(F)(F)C(F)(F)c2cc(-c4cnc([C@@H]5CCCN5)[nH]4)ccc2-3)[nH]1)C(C)C]

The title compound was prepared by using product (2S, 2'S)-2,2'-(5,5'-(9,9,10,10-tetrafluoro-9,10-dihydrophenanthren-2,7-diyl)bis(1H-imidazol-5,2-diyl))dipyrrolidine obtained in step 3 of Example 7 and MOC-valine as the starting materials according to the method in step 9 of Example 11.

Step 3 Preparation of 2-methoxy-ethyl N-((2S)-1-((S)-2-(5-(7-(2-((S)-1-((S)-2-(methoxycarbonylamino)-3-methylbutanoyl)-pyrrol-2-yl)-1H-imidazol-5-yl)-9,9,10,10-tetrafluoro-9,10-dihydrophenanthren-2-yl)-1H-imidazol-2-yl)-pyrrol-1-yl)-3-methyl-1-oxobutan-2-yl)carbamate

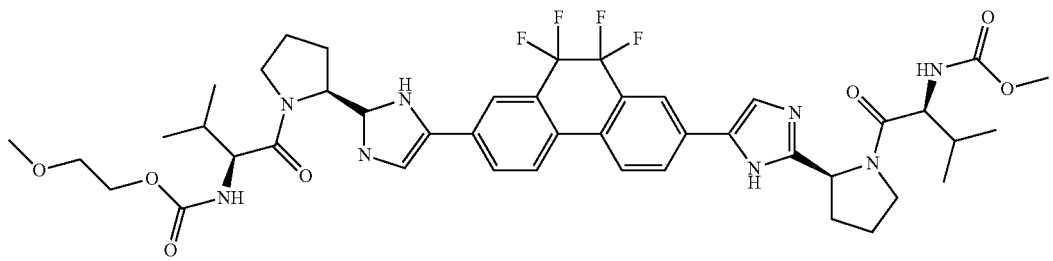

The title compound was prepared by using product (S)-2-(5-(7-(2-((S)-1-((S)-2-(methoxycarbonylamino)-3-methylbutanoyl)-pyrrol-2-yl)-1H-imidazol-5-yl)-9,9,10,10-tetrafluoro-9,10-dihydrophenanthren-2-yl)-1H-imidazol-2-yl)pyrrole obtained in step 2 and product (S)-2-(((2-methoxyethoxy)carbonyl)amino)-3-methyl-butyric acid obtained in step 1 as the starting materials according to the method in step 9 of Example 11.

¹HNMR: (500 MHz, DMSO-d6) δ: 11.98 (m, 2H), 7.24-8.41 (m, 10H), 5.09 (m, 2H), 3.25-4.06 (m, 16H), 1.98-2.14 (m, 10H), 0.87-0.96 (m, 12H).

ESI-MS m/z: [M+H]=881.

Example 16

Dimethyl 42S,2'S)-((2S,2'S)-2,2'-(6,6'-(9,9,10,10-tetrafluoro-9,10-dihydrophenanthren-2,7-diyl)bis(1H-benzo[d]imidazol-6,2-diyl))bis(pyrrolidin-2,1-diyl))bis(3-methyl-1-oxobutan-2,1-diyl))dicarbamate

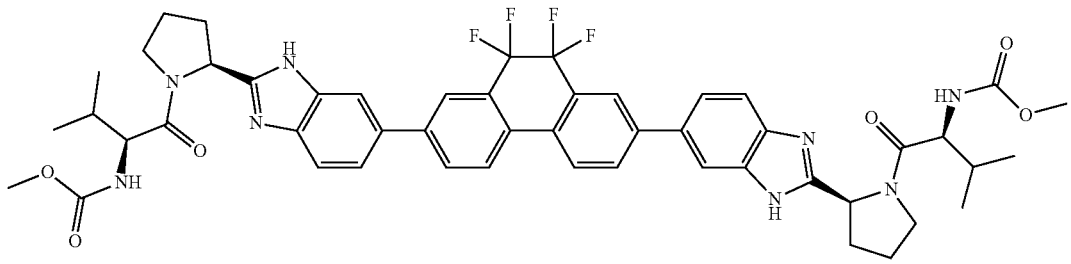

Step 1 Preparation of (2S,2'S)-2,2'-(6,6'-(9,9,10,10-tetrafluoro-9,10-dihydro phenanthren-2,7-diyl)bis(1H-benzo[d]imidazol-6,2-diyl)bis(1-tert-butoxycarbonylpyrrole)

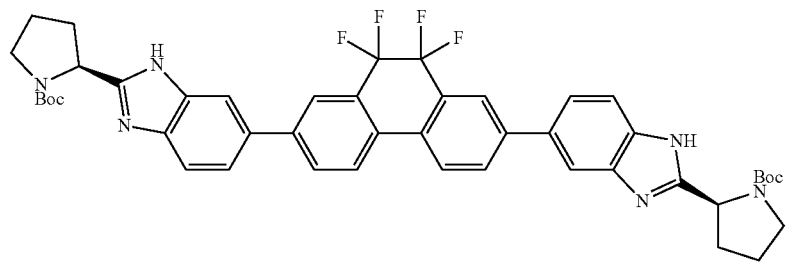 [SMILES: CC(C)(C)OC(=O)N1CCC[C@H]1c1nc2cc(-c3ccc4c(c3)C(F)(F)C(F)(F)c3cc(-c5ccc6nc([C@@H]7CCCN7C(=O)OC(C)(C)C)[nH]c6c5)ccc3-4)ccc2[nH]1]

The title compound was prepared by using product (S)-1-tert-butoxycarbonyl-2-(6-(4,4,5,5-tetramethyl-1,3,2-dioxaborolan-2-yl)-1H-benzo[d]imidazol-2-yl) pyrrolidine obtained in step 7 of Example 9 and product 2,7-dibromo-9,9,10,10-tetrafluoro-9,10-dihydrophenanthrene obtained in step 7 of Example 1 as the starting materials according to the method in step 8 of Example 9.

Step 2 Preparation of (2S,2'S)-2,2'-(6,6'-(9,9,10,10-tetrafluoro-9,10-dihydro phenanthren-2,7-diyl)bis(1H-benzo[d]imidazol-6,2-diyl))dipyrrole

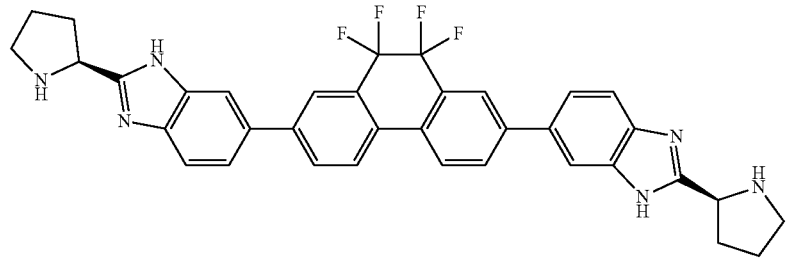 [SMILES: FC1(F)c2cc(-c3ccc4nc([C@@H]5CCCN5)[nH]c4c3)ccc2-c2ccc(-c3ccc4nc([C@@H]5CCCN5)[nH]c4c3)cc2C1(F)F]

The title compound was prepared by using product (2S,2'S)-2,2'-(6,6'-(9,9,10,10-tetrafluoro-9,10-dihydrophenanthren-2,7-diyl)bis(1H-benzo[d]imidazol-6,2-diyl)bis(1-tert-butoxycarbonylpyrrole) obtained in step 1 as the starting material according to the method in step 8 of Example 11.

Step 3 Methyl N—((S)-3-methyl-1-oxo-1-((S)-2-(5-(9,9,10,10-tetrafluoro-7-(2-((S)-1-(3-methyl-2-(methoxycarbonylamino)butanoyl)pyrrol-2-yl)-1H-benzo[d]imidazol-5-yl)-9,10-dihydrophenanthren-2-yl)-1H-benzo[d]imidazol-2-yl)pyrrol-1-yl) butanoyl-2-yl)carbamate methylbutanoyl)-1,4-dioxa-7-azaspiro[4.4]nonan-8-methanoic acid obtained in step 4 of Example 11 as the starting materials according to the method in step 7 of Example 11.

$^1$H NMR (300 MHz, CDCl$_3$) δ: 8.16 (d, 2H), 7.74-7.64 (m, 3H), 7.33 (s, 1H), 5.60-5.57 (d, 2H), 5.38-5.33 (1, 2H), 4.32 (m, 2H), 4.06-4.05 (d, 6H), 3.96-3.92 (m, 2H), 3.70 (s, 6H), 3.25 (m, 2H), 2.48 (m, 2H), 1.98-1.96 (d, 6H), 1.26 (d, 2H), 1.8 (m, 2H), 0.92-0.82 (dd, 8H).

ESI-MS m/z: [M+H]$^+$=953.

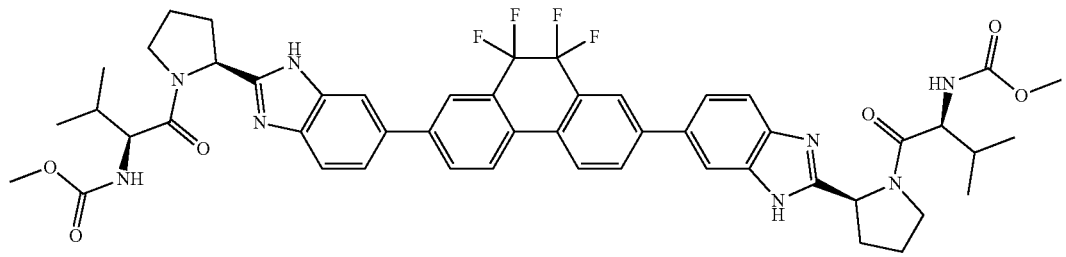

The title compound was prepared by using product (2S,2'S)-2,2'-(6,6'-(9,9,10,10-tetrafluoro-9,10-dihydrophenanthren-2,7-diyl)bis(1H-benzo[d]imidazol-6,2-diyl))dipyrrole obtained in step 2 and MOC-valine as the starting materials according to the method in step 9 of Example 11.

$^1$HNMR: (500 MHz, DMSO-d6) δ: 12.29 (m, 2H), 7.28-8.28 (m, 14H), 5.22 (m, 2H), 4.08-4.11 (m, 2H), 3.85-3.87 (m, 4H), 3.30 (m, 6H), 1.93-2.25 (m, 10H), 0.83-0.91 (m, 12H).

ESI-MS m/z: [M+H]=938.

Example 17

Dimethyl ((2S,2'S)-((2S,2'S)-2,2'-(5,5'-(9,9,10,10-tetrafluoro-9,10-dihydrophenanthren-2,7-diyl)bis(1H-imidazol-5,2-diyl))bis(1,4-dioxa-7-azaspiro[4.4]nonan-7,8-diyl))bis(3-methyl-1-oxobutan-2,1-diyl)) dicarbamate

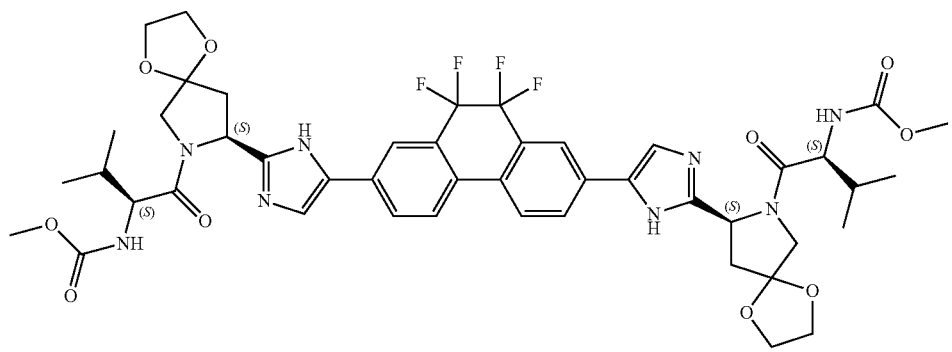

The title compound was prepared by using product 1,1'-(9, 9, 10, 10-tetrafluoro-9,10-dihydrophenanthren-2,7-diyl)bis(2-bromoethanone) obtained step 3 of Example 3 and product (S)-7-((S)-2-(methoxycarbonylamino)-3-

Experimental Example 1

Detection of the Anti-HCV-1b Replicon Activity of the Compound of the Present Invention 1 Materials 1.1 Compounds Each of the compounds prepared in the above examples of the present invention was dissolved at 10 mM in DMSO, then diluted to 50 μM with DMEM complete medium, then diluted to 20 nM with complete medium containing 0.5% DMSO, and then serially diluted by 3-fold, to obtain a total of 10 concentrations.

1.2 Cells

HCV 1b replicon cells, i.e., Huh7 cell line stably transfected with HCV genotype 1b replicon, were provided by WuXi AppTec (Shanghai) Co., Ltd. Specific preparation methods of Huh7 1b replicon cell system can be found in Lohmann V, Korner F, Koch J, Herian U, Theilmann L, Bartenschlager R., Replication of subgenomic hepatitis C virus RNAs in a hepatoma cell line, Science 285 (5424): 110-113 (1999).

1.3 Reagents
DMEM cell culture medium (DMEM medium) was purchased from Invitrogen, USA;
Fetal bovine serum (FBS) was purchased from Sigma, USA;
L (+)-Glutamine was purchased from Invitrogen, USA;
Penicillin-Streptomycin (Pen-Strep) was purchased from Invitrogen, USA;
Phosphate buffered saline (PBS) was purchased from Hyclone, USA;
Trypsin was purchased from Invitrogen, USA;
Dimethyl sulfoxide (DMSO) was purchased from Sigma, USA;
Bright-Glo detection reagent was purchased from Promega, USA;
Detection reagent for fluorescence assay of cell growth (CellTiter-Fluor) was purchased from Promega, USA.

1.4 Instrument
Automatic focusing fluorescence multimode microplate reader (PHERAstar Plus) was purchased from BMG Labtech, German.

2 Experimental Methods
1) Preparation of compounds: adding 75 μl of the compounds of the present invention at the above concentration gradient to a 96-well plate using POD810 system, with each concentration for each compound in duplicate;
2) Preparation of cells: collecting HCV 1b replicon cells in logarithmic phase and resuspending them in DMEM complete medium, and then adding 75 μl of the cell suspension to each well of the above 96-well plate ($8\times10^3$ cells/well); at the same time, establishing zero percent effect (ZPE) control group and hundred percent effect (HPE) control group, with ZPE group using complete culture medium containing 0.5% DMSO instead of the compound, and the HPE group merely containing DMEM medium in the wells.
3) Cell culture: placing the 96-well plate in a 37° C., 5% $CO_2$ incubator and culturing for 3 days.
4) Cell viability test: after adding detection reagent for fluorescence assay of cell growth to each well and culturing the cells in a 37° C., 5% $CO_2$ incubator for one hour, detecting the fluorescence signal values using the multimode microplate reader, with the raw data (RFU) being used for calculation of the cytotoxicity of the compounds;
5) Anti-HCV replicon activity assay: adding luciferase luminescence substrate Bright-Glo to each well, and detecting luminescence signal values using the multimode microplate reader within 5 min, with the raw data (RLU) being used for calculation of the anti-HCV activities of the compounds;
6) Data processing: processing the raw data using the following formula into the inhibition percentage of the compound against HCV replicon (Inhibition %) and the percentage of cell viability (Viability %):

Inhibition %=$(RLU_{ZPE}-RLU_{CPD})/(RLU_{ZPE}-RLU_{HPE})\times100$

Viability %=$(RFU_{CPD}-RFU_{HPE})/(RFU_{ZPE}-RFU_{HPE})\times100$ wherein CPD: the fluorescence signal value of the well of the compound; ZPE (zero percent effect): the fluorescence signal value of the zero percent effect control; HPE (hundred percent effect): the fluorescence signal value of the hundred percent effect control.

The Inhibition % and Viability % were introduced into GraphPad Prism software for data processing, respectively, to obtain the half effective concentration $EC_{50}$ of the compound against HCV replicon and the half cytotoxic concentration $CC_{50}$. Experimental results show that the compounds of the present invention have $EC_{50}$ against HCV-1b replicon which are much smaller than 0.1 nm, and $CC_{50}$ which are much larger than 10 nm. Results of some compounds are shown in Table 1.

TABLE 1

| Test compound | $EC_{50}$ (nm) | $CC_{50}$ (nm) | Test compound | $EC_{50}$ (nm) | $CC_{50}$ (nm) |
|---|---|---|---|---|---|
| Example 1 | 0.0046 | >10 | Example 2 | 0.017 | >10 |
| Example 3 | 0.017 | >10 | Example 4 | 0.047 | >10 |
| Example 5 | 0.041 | >10 | Example 6 | 0.014 | >10 |
| Example 7 | 0.0063 | >10 | Example 8 | 0.058 | >10 |
| Example 11 | 0.006 | >10 | Example 12 | 0.008 | >10 |
| Example 13 | 0.056 | >10 | Example 14 | 0.006 | >10 |
| Example 17 | 0.007 | >10 | | | |

As can be seen from the above experiments, the compounds of the present invention have good inhibitory activity for hepatitis C virus and, at the same time, have low toxicity for the host cells, and are of high efficacy and good safety, and thus are very promising to be medicaments for the treatment and/or prevention of HCV infection related diseases.

Experimental Example 2

Detection of the Anti-HCV-1a Replicon Activity of the Compound of the Present Invention HCV 1a replicon cells, i.e., Huh7 cell line stably transfected with HCV genotype 1a replicon (provided by WuXi AppTec (Shanghai) Co., Ltd.) were used as the experimental cells. As described above for the HCV 1b replicon cell system, the HCV genotype 1a replicon cell systems were similarly prepared.

The anti-HCV-1a activities of the compounds of the present invention were tested according to the method for testing the anti-HCV-1b replicon activity in Experimental Example 1. The results indicate that the compounds of the present invention have $EC_{50}$ against HCV-1a replicon which are smaller than 0.2 nm, and $CC_{50}$ which are much larger than 10 nm. Results of some compounds are shown in Table 2.

TABLE 2

| Test compound | $EC_{50}$ (nm) | $CC_{50}$ (nm) | Test compound | $EC_{50}$ (nm) | $CC_{50}$ (nm) |
|---|---|---|---|---|---|
| Example 1 | 0.19 | >10 | Example 11 | 0.079 | >10 |
| Example 12 | 0.061 | >10 | Example 14 | 0.15 | >10 |
| Example 17 | 0.175 | >10 | | | >10 |

The compounds of the present invention also have good inhibitory activities for hepatitis C virus subtype 1a and meantime have low toxicity for the host cells, and are of high efficacy and good safety, and thus are very promising to be medicaments for the treatment and/or prevention of HCV infection related diseases. Although the present invention has been described above in detail, those skilled in the art should understand that various modifications and changes can be made to the present invention without departing from the spirit and scope of the present invention. The scope of

The invention claimed is:

1. A compound of general formula I

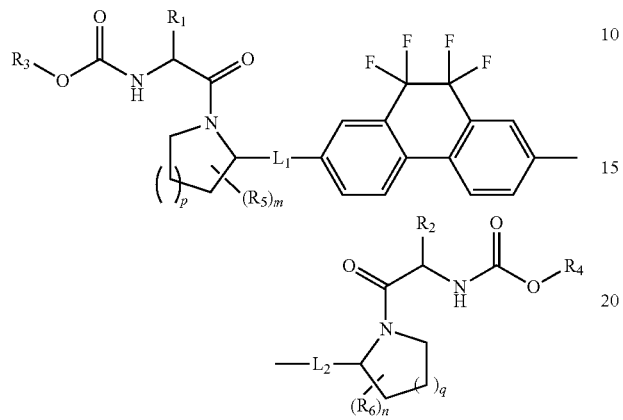

wherein:
each of $L_1$ and $L_2$ is independently selected from the group consisting of aryl, heteroaryl, -aryl-aryl-, -aryl-heteroaryl- and -heteroaryl-heteroaryl-, wherein the aryl or heteroaryl can be substituted with one or more of halogen, hydroxyl, amino, carboxyl, cyano, nitro, alkyl, cycloalkyl, heterocycloalkyl, alkoxy, haloalkyl, hydroxyalkyl, aminoalkyl, carboxyalkyl, cyanoalkyl, nitroalkyl, cycloalkylalkyl, heterocycloalkylalkyl, alkoxyalkyl, monoalkylamino, monoalkylaminoalkyl, dialkylamino, dialkylaminoalkyl, alkylacyl, alkyl acyl alkyl, alkoxyacyl, alkoxyacylalkyl, alkylacyloxy, alkylacyloxyalkyl, aminoacyl, aminoacyl alkyl, monoalkylaminoacyl, monoalkylaminoacylalkyl, dialkylaminoacyl, dialkylaminoacylalkyl, alkylacylamino and alkyl acylaminoalkyl;

each of p and q is independently selected from the group consisting of 1, 2 and 3;

each of $R_1$ and $R_2$ is independently selected from the group consisting of hydrogen, alkyl, cycloalkyl, heterocycloalkyl, aryl and heteroaryl, wherein the alkyl, cycloalkyl, heterocycloalkyl, aryl or heteroaryl can be substituted with one or more of halogen, hydroxyl, amino, carboxyl, cyano, nitro, alkyl, cycloalkyl, heterocycloalkyl, alkoxy, haloalkyl, hydroxyalkyl, carboxyalkyl, monoalkylamino, dialkylamino, alkylacyl, alkoxyacyl, alkylacyloxy, aminoacyl, monoalkylaminoacyl, di alkylaminoacyl and alkylacylamino;

each of $R_3$ and $R_4$ is independently selected from the group consisting of hydrogen, alkyl, cycloalkyl and heterocycloalkyl, wherein the alkyl, cycloalkyl or heterocycloalkyl can be substituted with one or more of halogen, hydroxyl, amino, carboxyl, cyano, nitro, alkyl, cycloalkyl, heterocycloalkyl, alkoxy, aryl and heteroaryl; and each of $R_5$ and $R_6$ is independently selected from the group consisting of hydrogen, halogen, hydroxyl, amino, carboxyl, cyano, nitro, alkyl, cycloalkyl, heterocycloalkyl, alkoxy, alkoxyalkyl, aryl and heteroaryl, wherein each of m and n is independently selected from the group consisting of 1, 2 and 3, and when m or n is 2, each $R_5$ or $R_6$ together with the C atom to which they are attached can form a cycloalkyl or heterocycloalkyl; wherein the hydroxyl, amino, carboxyl, alkyl, cycloalkyl, heterocycloalkyl, alkoxy, alkoxyalkyl, aryl and heteroaryl can be substituted with one or more of halogen, hydroxyl, amino, carboxyl, cyano, nitro, alkyl, cycloalkyl, heterocycloalkyl, alkoxy, hydroxyalkyl, carboxyalkyl, monoalkylamino, dialkylamino, alkylacyl, alkoxyacyl, alkylacyloxy, aminoacyl, monoalkylaminoacyl, dialkylaminoacyl and alkylacylamino, or a pharmaceutically acceptable salt or isomer thereof.

2. The compound according to claim 1, wherein the compound is the compound of formula Ia,

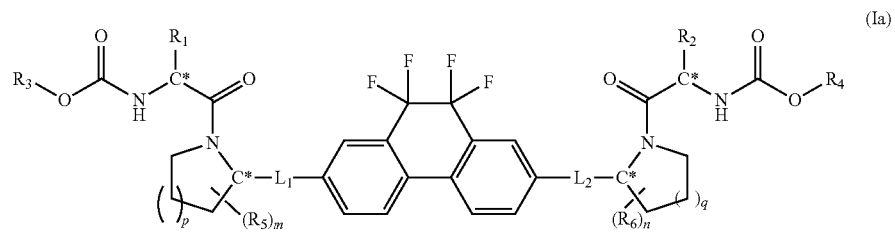

wherein C* is in S configuration,
or the pharmaceutically acceptable salt or isomer thereof.

3. The compound according to claim 1, wherein:
each of $L_1$ and $L_2$ is independently selected from the group consisting of phenyl, naphthyl, imidazolyl, benzimidazolyl, -phenyl-imidazolyl-, imidazopyridyl, quinazolinonyl, pyrrolyl, imidazolonyl, furanyl, thienyl, pyrazolyl, oxazolyl, thiazolyl, isoxazolyl, isothiazolyl, oxadiazolyl and triazolyl, wherein the phenyl, naphthyl, imidazolyl, benzimidazolyl, -phenyl-imidazolyl-, imidazopyridyl, quinazolinonyl, pyrrolyl, imidazolonyl, furanyl, thienyl, pyrazolyl, oxazolyl, thiazolyl, isoxazolyl, isothiazolyl, oxadiazolyl and triazolyl can be substituted with one or more of halogen, hydroxyl, amino, carboxyl, cyano, nitro, $C_{1-10}$ alkyl, $C_{3-10}$ cycloalkyl, $C_{3-10}$ heterocycloalkyl, $C_{1-10}$ alkoxy, $C_{1-10}$ haloalkyl, hydroxy-$C_{1-10}$ alkyl, amino-$C_{1-10}$ alkyl, carboxy-$C_{1-10}$ alkyl, cyano-$C_{1-10}$ alkyl, nitro-$C_{1-10}$ alkyl, $C_{3-10}$ cycloalkyl-$C_{1-6}$ alkyl, $C_{3-10}$ heterocycloalkyl-$C_{1-6}$ alkyl, $C_{1-10}$ alkoxy-$C_{1-6}$ alkyl, mono$C_{1-10}$ alkylamino, mono$C_{1-10}$ alkylamino-$C_{1-6}$ alkyl, di$C_{1-10}$ alkylamino, di$C_{1-10}$ alkylamino-$C_{1-6}$ alkyl, $C_{1-10}$ alkylacyl, $C_{1-10}$ alkylacyl-$C_{1-6}$ alkyl, $C_{1-10}$ alkoxyacyl, $C_{1-10}$ alkoxyacyl-$C_{1-6}$ alkyl, $C_{1-10}$ alkylacyloxy, $C_{1-10}$ alkylacyloxy-$C_{1-6}$ alkyl, aminoacyl, aminoacyl-$C_{1-6}$ alkyl, mono $C_{1-10}$ alkylaminoacyl, mono$C_{1-10}$ alkylaminoacyl-$C_{1-6}$ alkyl, di$C_{1-10}$ alkylaminoacyl, di$C_{1-10}$ alkylaminoacyl-$C_{1-6}$ alkyl, $C_{1-10}$ alkylacylamino and $C_{1-10}$ alkylacylamino-$C_{1-6}$ alkyl;

each of R₁ and R₂ is independently selected from the group consisting of hydrogen, $C_{1-6}$ alkyl, $C_{3-8}$ cycloalkyl, $C_{3-8}$ heterocycloalkyl, aryl or heteroaryl, wherein the $C_{1-6}$ alkyl, $C_{3-8}$ cycloalkyl, $C_{3-8}$ heterocycloalkyl, aryl or heteroaryl can be substituted with one or more of halogen, hydroxyl, amino, carboxyl, cyano, nitro, $C_{1-6}$ alkyl, $C_{3-8}$ cycloalkyl, $C_{3-8}$ heterocycloalkyl, $C_{1-6}$ alkoxy, hydroxy-$C_{1-6}$ alkyl, carboxy-$C_{1-6}$ alkyl, mono$C_{1-6}$ alkylamino, di$C_{1-6}$ alkylamino, $C_{1-6}$ alkylacyl, $C_{1-6}$ alkoxyacyl, $C_{1-6}$ alkylacyloxy, aminoacyl, mono$C_{1-6}$ alkylaminoacyl, di$C_{1-6}$ alkylaminoacyl and $C_{1-6}$ alkylacylamino;

each of R₃ and R₄ is independently selected from the group consisting of hydrogen, $C_{1-6}$ alkyl, $C_{3-8}$ cycloalkyl and $C_{3-8}$ heterocycloalkyl, wherein the $C_{1-6}$ alkyl, $C_{3-8}$ cycloalkyl or $C_{3-8}$ heterocycloalkyl can be substituted with one or more of halogen, hydroxyl, amino, carboxyl, cyano, nitro, $C_{1-6}$ alkyl, $C_{3-8}$ cycloalkyl, $C_{3-8}$ heterocycloalkyl, $C_{1-6}$ alkoxy, aryl and heteroaryl; and each of R₅ and R₆ is independently selected from the group consisting of hydrogen, cyano, hydroxyl, amino, $C_{1-6}$ alkyl, $C_{3-8}$ cycloalkyl, $C_{3-8}$ heterocycloalkyl, halogen, $C_{1-6}$ alkoxy-$C_{1-6}$ alkyl, aryl and heteroaryl, wherein each of m and n is independently selected from the group consisting of 1, 2 and 3, and when m or n is 2, each R₅ or R₆ together with the C atom to which they are attached can form a $C_{3-8}$ cycloalkyl or $C_{3-8}$ heterocycloalkyl; wherein the hydroxyl, amino, $C_{1-6}$ alkyl, $C_{3-8}$ cycloalkyl, $C_{3-8}$ heterocycloalkyl, halogen, $C_{1-6}$ alkoxy-$C_{1-6}$ alkyl, aryl and heteroaryl can be substituted with one or more of halogen, hydroxyl, amino, carboxyl, cyano, nitro, $C_{1-6}$ alkyl, $C_{3-8}$ cycloalkyl, $C_{3-8}$ heterocycloalkyl, $C_{1-6}$ alkoxy, hydroxy-$C_{1-6}$ alkyl, carboxy-$C_{1-6}$ alkyl, mono$C_{1-6}$ alkylamino, di$C_{1-6}$ alkylamino, $C_{1-6}$ alkylacyl, $C_{1-6}$ alkoxyacyl, $C_{1-6}$ alkylacyloxy, aminoacyl, mono$C_{1-6}$ alkylaminoacyl, di$C_{1-6}$ alkylaminoacyl and $C_{1-6}$ alkylacylamino, or the pharmaceutically acceptable salt or isomer thereof.

4. The compound according to claim 1, wherein:

each of L₁ and L₂ is independently selected from the group consisting of the following groups:

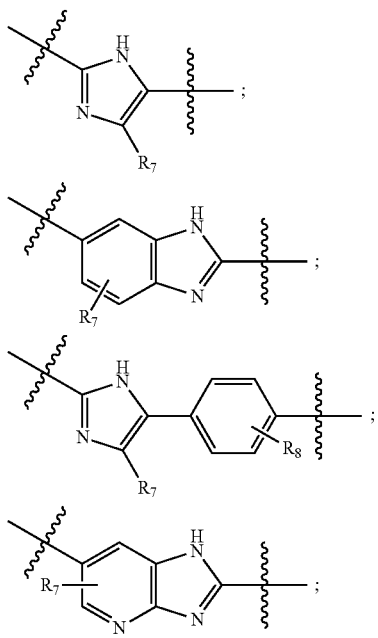

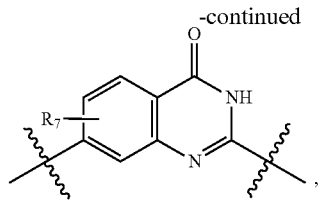

wherein each of R₇ and R₈ is independently selected from the group consisting of hydrogen, halogen, hydroxyl, amino, carboxyl, cyano, nitro, alkyl, cycloalkyl, heterocycloalkyl, alkoxy, haloalkyl, hydroxyalkyl, aminoalkyl, carboxyalkyl, cyanoalkyl, nitroalkyl, cycloalkylalkyl, heterocycloalkylalkyl, alkoxyalkyl, monoalkyl amino, monoalkylaminoalkyl, di alkyl amino, dialkylaminoalkyl, alkylacyl, alkylacylalkyl, alkoxyacyl, alkoxyacyl alkyl, alkylacyloxy, alkylacyloxyalkyl, aminoacyl, aminoacylalkyl, monoalkylaminoacyl, monoalkylaminoacylalkyl, dialkylaminoacyl, dialkylaminoacylalkyl, alkylacylamino and alkylacylaminoalkyl, or the pharmaceutically acceptable salt or isomer thereof.

5. The compound according to claim 1, wherein each of R₁ and R₂ is independently selected from the group consisting of hydrogen, methyl, ethyl, propyl, isopropyl, butyl, isobutyl, tert-butyl, cyclopropyl, cyclobutyl, cyclopentyl, cyclohexyl, tetrahydropyrrolyl, tetrahydrofuranyl, tetrahydrothienyl, tetrahydrothiazolyl, tetrahydrooxazolyl, piperidinyl, piperazinyl, N-alkylpiperazinyl, phenyl, naphthyl, pyrrolyl, thienyl, thiazolyl, oxazolyl and pyridyl, wherein the methyl, ethyl, propyl, isopropyl, butyl, isobutyl, tert-butyl, cyclopropyl, cyclobutyl, cyclopentyl, cyclohexyl, cycloheptyl, tetrahydropyrrolyl, tetrahydrofuranyl, tetrahydrothienyl, tetrahydrothiazolyl, tetrahydrooxazolyl, piperidinyl, piperazinyl, N-alkylpiperazinyl, phenyl, naphthyl, pyrrolyl, thienyl, thiazolyl, oxazolyl and pyridyl can be substituted with one or more of halogen, hydroxyl, amino, carboxyl, cyano, nitro, $C_{1-6}$ alkyl, $C_{1-6}$ alkoxy, hydroxy-$C_{1-6}$ alkyl, carboxy-$C_{1-6}$ alkyl, mono$C_{1-6}$ alkylamino and di$C_{1-6}$ alkylamino, or the pharmaceutically acceptable salt or isomer thereof.

6. The compound according to claim 1, wherein each of R₃ and R₄ is independently selected from the group consisting of hydrogen, methyl, ethyl, propyl, isopropyl, butyl, isobutyl, tert-butyl, cyclopropyl, cyclobutyl, cyclopentyl, cyclohexyl, tetrahydropyrrolyl, tetrahydrofuranyl, tetrahydrothienyl, tetrahydrothiazolyl, tetrahydrooxazolyl, piperidinyl and piperazinyl, wherein the methyl, ethyl, propyl, isopropyl, butyl, isobutyl, tert-butyl, cyclopropyl, cyclobutyl, cyclopentyl, cyclohexyl, cycloheptyl, tetrahydropyrrolyl, tetrahydrofuranyl, tetrahydrothienyl, tetrahydrothiazolyl, tetrahydrooxazolyl, piperidinyl and piperazinyl can be substituted with one or more of halogen, hydroxyl, amino, carboxyl, cyano, nitro, $C_{1-6}$ alkyl, cyclopropyl, cyclobutyl, cyclopentyl, cyclohexyl, tetrahydropyrrolyl, tetrahydrofuranyl, tetrahydrothienyl, tetrahydrothiazolyl, tetrahydrooxazolyl, piperidinyl, piperazinyl, N-alkylpiperazinyl, $C_{1-6}$ alkyl, phenyl and heteroaryl, or the pharmaceutically acceptable salt or isomer thereof.

7. The compound according to claim 1, wherein each of R₅ and R₆ is independently selected from the group consisting of hydrogen, halogen, cyano, hydroxyl, amino, carboxyl, nitro, $C_{1-6}$ alkyl, $C_{3-6}$ cycloalkyl, $C_{3-6}$ heterocycloalkyl, $C_{1-6}$ alkoxyhaloalkyl, cyano$C_{1-6}$ alkyl, hydroxy$C_{1-6}$ alkyl, amino$C_{1-6}$ alkyl, carboxy$C_{1-6}$ alkyl, nitro$C_{1-6}$ alkyl, $C_{3-6}$ cycloalkyl-$C_{1-6}$ alkyl, $C_{3-6}$ heterocycloalkyl-$C_{1-6}$ alkyl, or when m or n is 2,

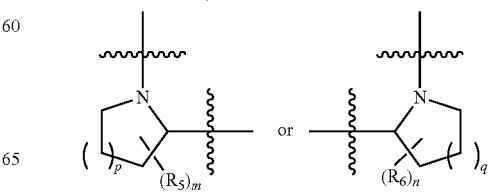

is each independently selected from the group consisting of azaspiroalkyl, oxaazaspiroalkyl and azabicycloalkyl,
or the pharmaceutically acceptable salt or isomer thereof.
8. The compound according to claim 1, wherein the compound is selected from the group consisting of the follow compounds:
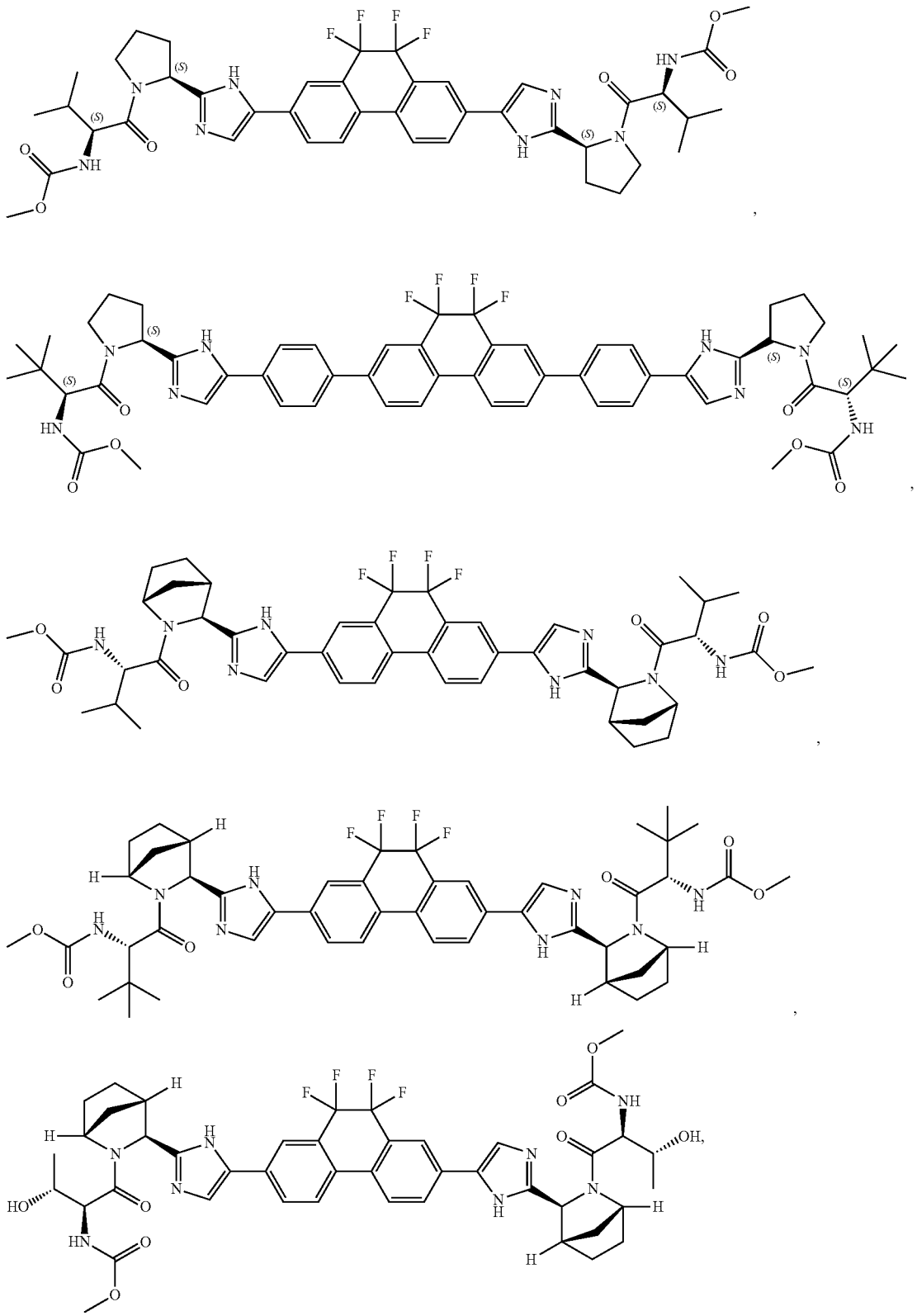

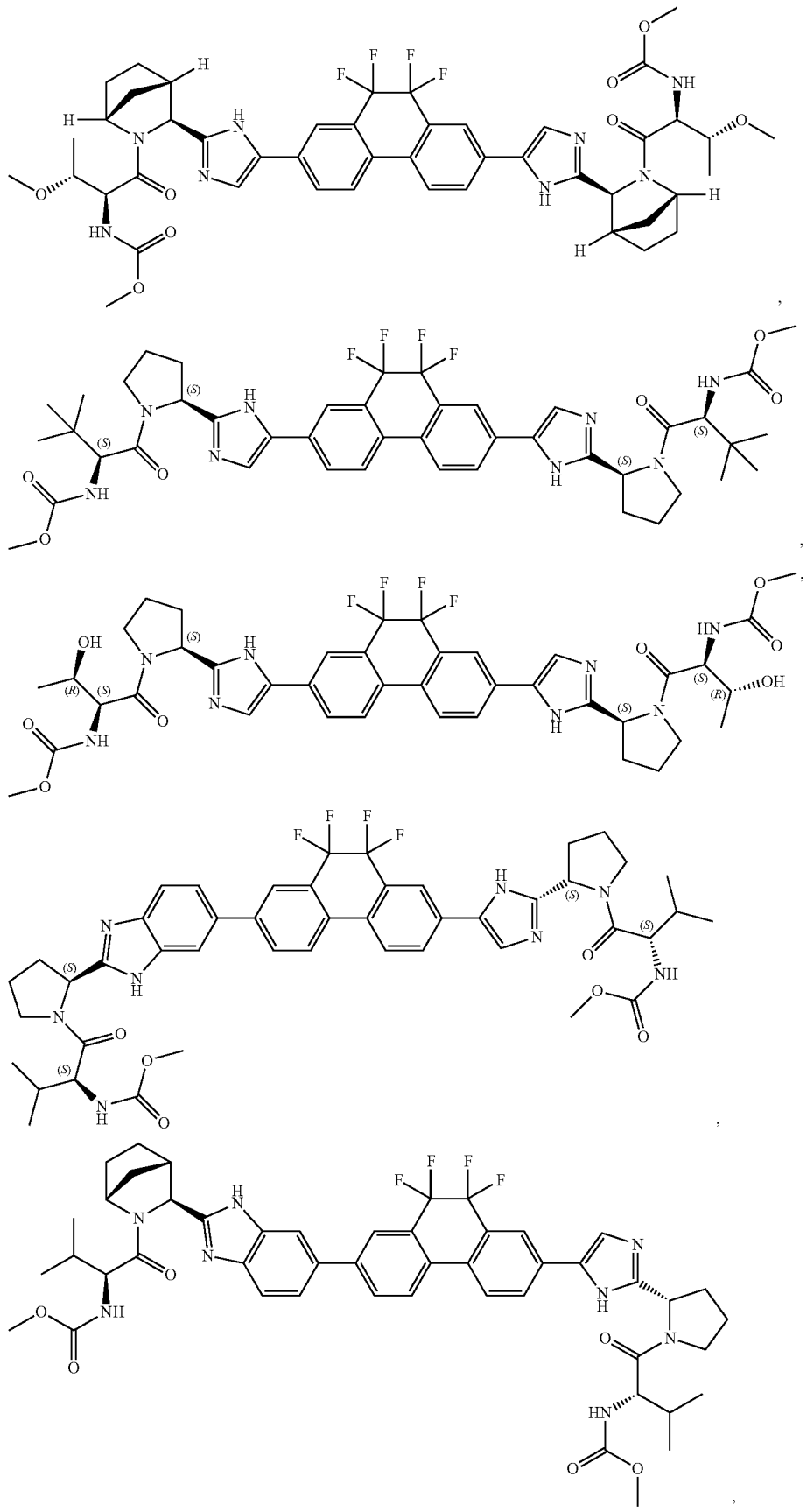

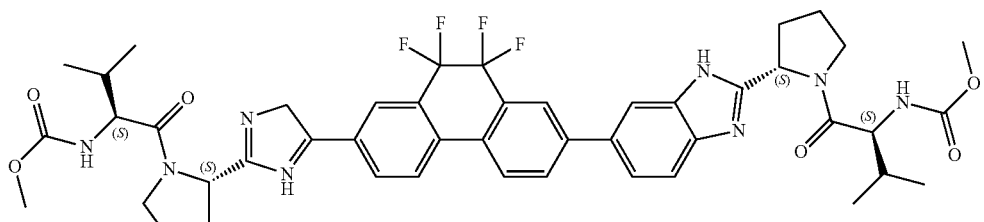
,
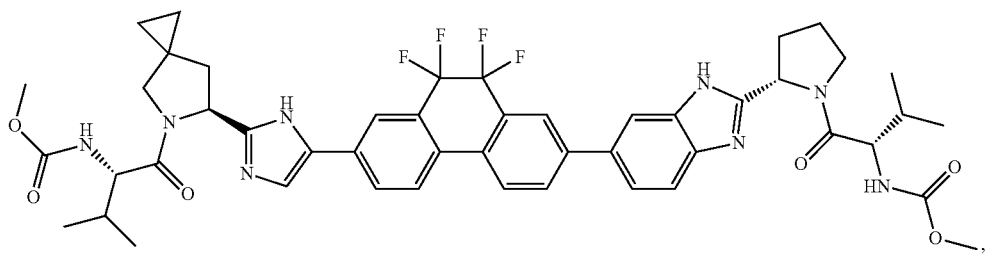
,
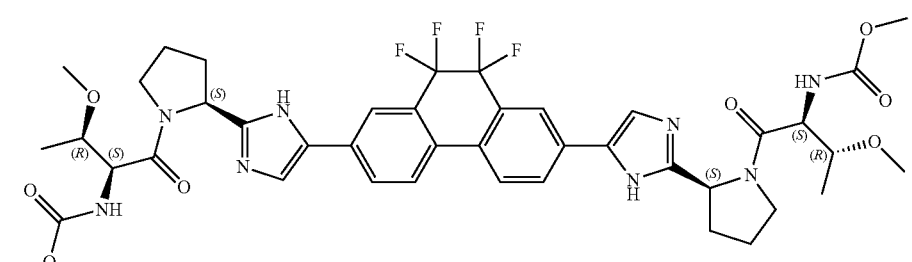
,
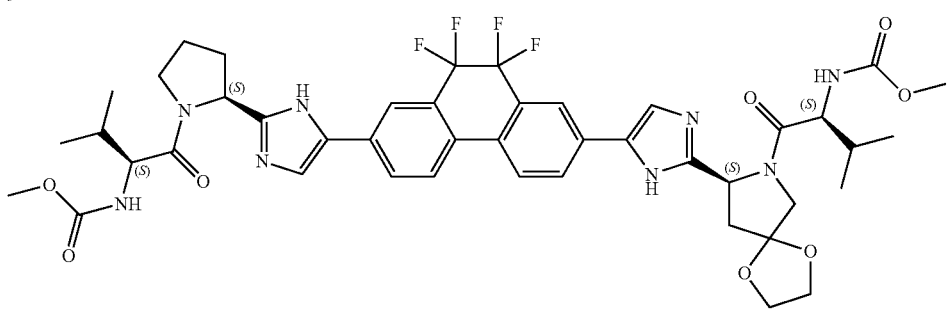
,
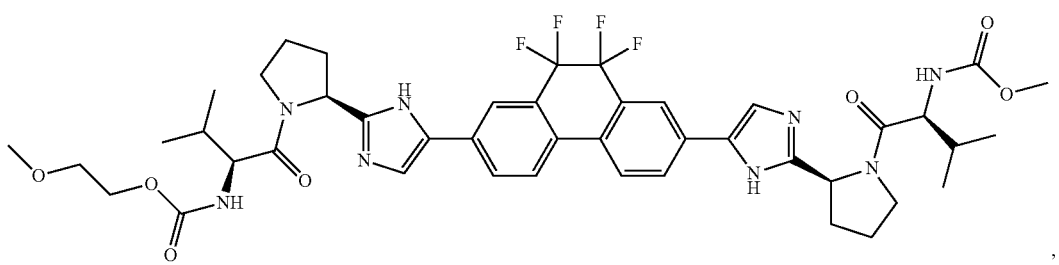
,
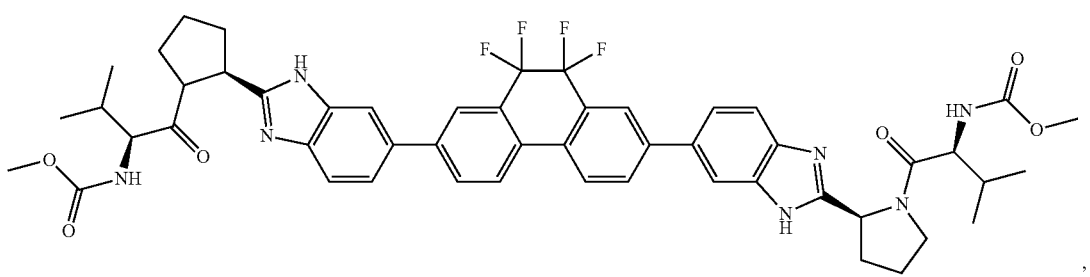
, and

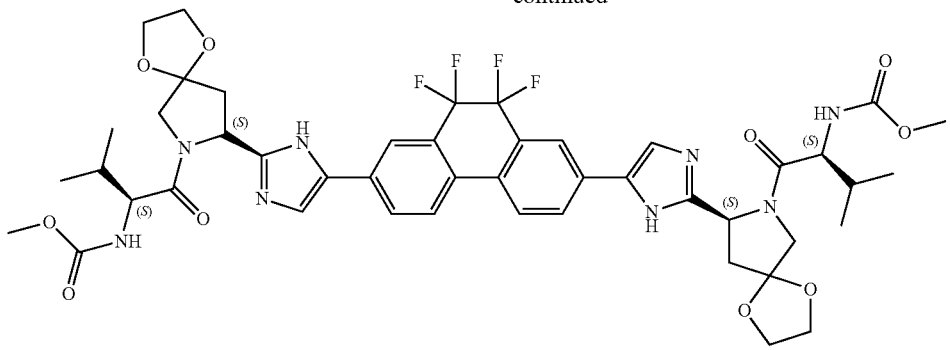

or the pharmaceutically acceptable salt or isomer thereof.

9. A pharmaceutical composition comprising the compound according to claim 1, or the pharmaceutically acceptable salt or isomer thereof and a pharmaceutically acceptable carrier.

10. A method for treating and/or preventing HCV infection, comprising administering to an individual in need thereof a therapeutically and/or prophylactically effective amount of the compound according to claim 1, or the pharmaceutically acceptable salt or isomer thereof.

11. The compound according to claim 3, wherein each of $L_1$ and $L_2$ is independently selected from the group consisting of the following groups:

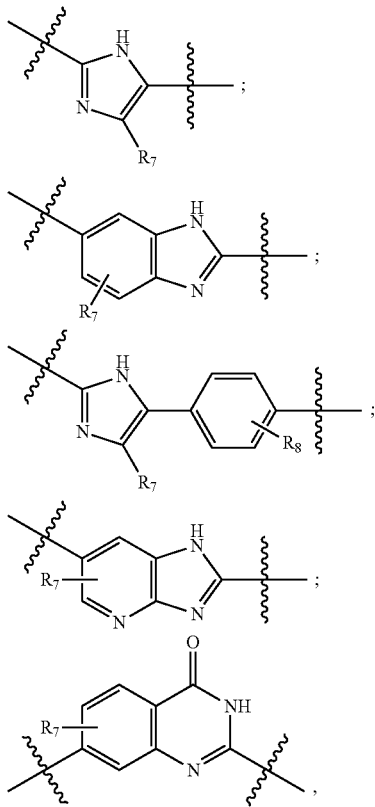

wherein each of $R_7$ and $R_8$ is independently selected from the group consisting of hydrogen, halogen, hydroxyl, amino, carboxyl, cyano, nitro, alkyl, cycloalkyl, heterocycloalkyl, alkoxy, haloalkyl, hydroxyalkyl, aminoalkyl, carboxyalkyl, cyanoalkyl, nitroalkyl, cycloalkylalkyl, heterocycloalkylalkyl, alkoxyalkyl, monoalkylamino, monoalkylaminoalkyl, dialkylamino, dialkylaminoalkyl, alkylacyl, alkylacylalkyl, alkoxyacyl, alkoxyacylalkyl, alkylacyloxy, alkylacyloxyalkyl, aminoacyl, aminoacylalkyl, monoalkylaminoacyl, monoalkylaminoacylalkyl, dialkylaminoacyl, dialkylaminoacylalkyl, alkylacylamino and alkylacylaminoalkyl, or the pharmaceutically acceptable salt or isomer thereof.

12. The compound according to claim 5, wherein each of $R_3$ and $R_4$ is independently selected from the group consisting of hydrogen, methyl, ethyl, propyl, isopropyl, butyl, isobutyl, tert-butyl, cyclopropyl, cyclobutyl, cyclopentyl, cyclohexyl, tetrahydropyrrolyl, tetrahydrofuranyl, tetrahydrothienyl, tetrahydrothiazolyl, tetrahydrooxazolyl, piperidinyl and piperazinyl, wherein the methyl, ethyl, propyl, isopropyl, butyl, isobutyl, tert-butyl, cyclopropyl, cyclobutyl, cyclopentyl, cyclohexyl, cycloheptyl, tetrahydropyrrolyl, tetrahydrofuranyl, tetrahydrothienyl, tetrahydrothiazolyl, tetrahydrooxazolyl, piperidinyl and piperazinyl can be substituted with one or more of halogen, hydroxyl, amino, carboxyl, cyano, nitro, $C_{1-6}$ alkyl, cyclopropyl, cyclobutyl, cyclopentyl, cyclohexyl, tetrahydropyrrolyl, tetrahydrofuranyl, tetrahydrothienyl, tetrahydrothiazolyl, tetrahydrooxazolyl, piperidinyl, piperazinyl, N-alkylpiperazinyl, $C_{1-6}$ alkyl, phenyl and heteroaryl, or the pharmaceutically acceptable salt or isomer thereof.

13. The compound according to claim 6, wherein each of $R_5$ and $R_6$ is independently selected from the group consisting of hydrogen, halogen, cyano, hydroxyl, amino, carboxyl, nitro, $C_{1-6}$ alkyl, $C_{3-6}$ cycloalkyl, $C_{3-6}$ heterocycloalkyl, $C_{1-6}$ alkoxyhaloalkyl, cyano$C_{1-6}$ alkyl, hydroxy$C_{1-6}$ alkyl, amino$C_{1-6}$ alkyl, carboxy$C_{1-6}$ alkyl, nitro$C_{1-6}$ alkyl, $C_{3-6}$ cycloalkyl-$C_{1-6}$ alkyl, $C_{3-6}$ heterocycloalkyl-$C_{1-6}$ alkyl, or when m or n is 2,

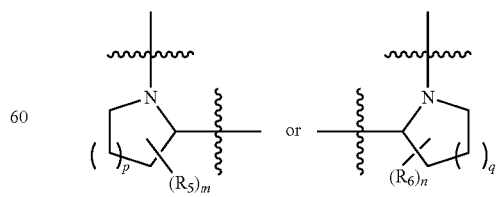

is each independently selected from the group consisting of azaspiroalkyl, oxaazaspiroalkyl and azabicycloalkyl, or the pharmaceutically acceptable salt or isomer thereof.

14. The compound according to claim 7, wherein the azaspiroalkyl is azaspiro[2.4]heptyl, azaspiro[3.4]octyl, azaspiro[4.4]nonyl, azaspiro[2.5]octyl, azaspiro[3.5]nonyl, azaspiro[4.5]decyl, azaspiro[2.6]nonyl or azaspiro[3.6]decyl, the oxaazaspiroalkyl is oxa-azaspiro[2.4]heptyl, oxa-azaspiro[3.4]octyl, oxa-azaspiro[4.4]nonyl, dioxa-azaspiro[4.4]nonyl, oxa-azaspiro[4.5]decyl, dioxa-azaspiro[4.5]decyl or trioxa-azaspiro[4.5]decyl, and the azabicycloalkyl is azabicyclo[3.1.0]hexane, azabicyclo[3.2.0]heptyl, octahydrocyclopentapyrrolyl, octahydro-1H-isoindolyl, octahydro-1H-indolyl or azabicyclo[2.2.1]heptyl, or the pharmaceutically acceptable salt or isomer thereof.

15. The compound according to claim 11, wherein each of $R_3$ and $R_4$ is independently selected from the group consisting of hydrogen, methyl, ethyl, propyl, isopropyl, butyl, isobutyl, tert-butyl, cyclopropyl, cyclobutyl, cyclopentyl, cyclohexyl, tetrahydropyrrolyl, tetrahydrofuranyl, tetrahydrothienyl, tetrahydrothiazolyl, tetrahydrooxazolyl, piperidinyl and piperazinyl, wherein the methyl, ethyl, propyl, isopropyl, butyl, isobutyl, tert-butyl, cyclopropyl, cyclobutyl, cyclopentyl, cyclohexyl, cycloheptyl, tetrahydropyrrolyl, tetrahydrofuranyl, tetrahydrothienyl, tetrahydrothiazolyl, tetrahydrooxazolyl, piperidinyl and piperazinyl can be substituted with one or more of halogen, hydroxyl, amino, carboxyl, cyano, nitro, $C_{1-6}$ alkyl, cyclopropyl, cyclobutyl, cyclopentyl, cyclohexyl, tetrahydropyrrolyl, tetrahydrofuranyl, tetrahydrothienyl, tetrahydrothiazolyl, tetrahydrooxazolyl, piperidinyl, piperazinyl, N-alkylpiperazinyl, $C_{1-6}$ alkyl, phenyl and heteroaryl, or the pharmaceutically acceptable salt or isomer thereof.

16. The compound according to claim 15, wherein each of $R_5$ and $R_6$ is independently selected from the group consisting of hydrogen, halogen, cyano, hydroxyl, amino, carboxyl, nitro, $C_{1-6}$ alkyl, $C_{3-6}$ cycloalkyl, $C_{3-6}$ heterocycloalkyl, $C_{1-6}$ alkoxyhaloalkyl, cyano$C_{1-6}$ alkyl, hydroxy$C_{1-6}$ alkyl, amino$C_{1-6}$ alkyl, carboxy$C_{1-6}$ alkyl, nitro$C_{1-6}$ alkyl, $C_{3-6}$ cycloalkyl-$C_{1-6}$ alkyl, $C_{3-6}$ heterocycloalkyl-$C_{1-6}$ alkyl, or when m or n is 2,

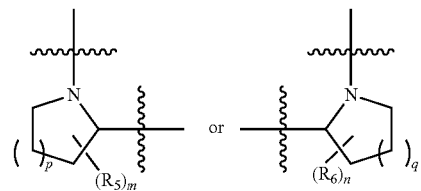

is each independently selected from the group consisting of azaspiroalkyl, oxaazaspiroalkyl and azabicycloalkyl, or the pharmaceutically acceptable salt or isomer thereof.

17. The compound according to claim 16, wherein the azaspiroalkyl is azaspiro[2.4]heptyl, azaspiro[3.4]octyl, azaspiro[4.4]nonyl, azaspiro[2.5]octyl, azaspiro[3.5]nonyl, azaspiro[4.5]decyl, azaspiro[2.6]nonyl or azaspiro[3.6]decyl, the oxaazaspiroalkyl is oxa-azaspiro[2.4]heptyl, oxa-azaspiro[3.4]octyl, oxa-azaspiro[4.4]nonyl, dioxa-azaspiro[4.4]nonyl, oxa-azaspiro[4.5]decyl, dioxa-azaspiro[4.5]decyl or trioxa-azaspiro[4.5]decyl, and the azabicycloalkyl is azabicyclo[3.1.0]hexane, azabicyclo[3.2.0]heptyl, octahydrocyclopentapyrrolyl, octahydro-1H-isoindolyl, octahydro-1H-indolyl or azabicyclo[2.2.1]heptyl, or the pharmaceutically acceptable salt or isomer thereof.

18. A method for treating and/or preventing HCV infection, comprising administering to an individual in need thereof a therapeutically and/or prophylactically effective amount of the compound according to claim 8, or the pharmaceutically acceptable salt or isomer thereof.

19. A method for treating and/or preventing HCV infection, comprising administering to an individual in need thereof a therapeutically and/or prophylactically effective amount of the pharmaceutical composition according to claim 9.

* * * * *

UNITED STATES PATENT AND TRADEMARK OFFICE
CERTIFICATE OF CORRECTION

| | | |
|---|---|---|
| PATENT NO. | : 9,512,108 B2 | Page 1 of 1 |
| APPLICATION NO. | : 15/030990 | |
| DATED | : December 6, 2016 | |
| INVENTOR(S) | : Yong Wang et al. | |

It is certified that error appears in the above-identified patent and that said Letters Patent is hereby corrected as shown below:

In the Claims

In Claim 1, Column 83, Line 7-25, delete the entire contents of lines 7-25 and insert

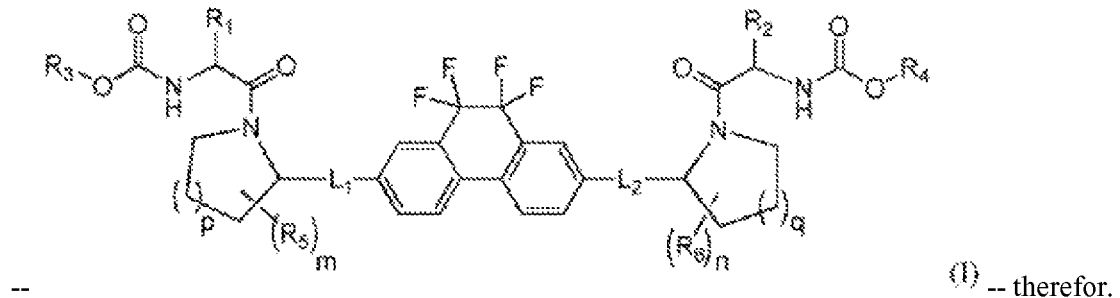

-- therefor.

In Claim 8, Columns 91-92, delete the last structure on the page and insert

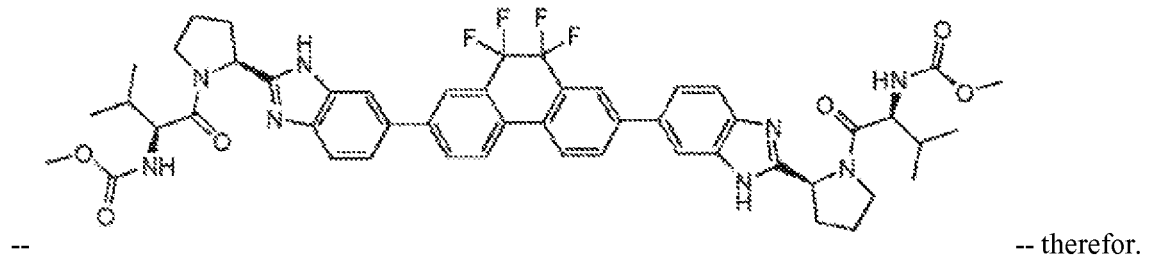

-- therefor.

Signed and Sealed this
Seventh Day of March, 2017

Michelle K. Lee
*Director of the United States Patent and Trademark Office*